(12) United States Patent
Gerlach

(10) Patent No.: US 11,198,696 B2
(45) Date of Patent: Dec. 14, 2021

(54) SUBSTITUTED XANTHINES AS INHIBITORS OF TRANSIENT RECEPTOR POTENTIAL CATION CHANNEL SUBFAMILY C, MEMBER 5 ACTIVITY

(71) Applicants: Boehringer Ingelheim International GmbH, Ingelheim am Rhein (DE); Hydra Biosciences, LLC, Belmont, MA (US)

(72) Inventor: Kai Gerlach, Ingelheim am Rhein (DE)

(73) Assignees: Boehringer Ingelheim International GmbH, Ingelheim am Rhein (DE); Hydra Biosciences, LLC, Belmont, MA (US)

( * ) Notice: Subject to any disclaimer, the term of this patent is extended or adjusted under 35 U.S.C. 154(b) by 29 days.

(21) Appl. No.: 16/710,887

(22) Filed: Dec. 11, 2019

(65) Prior Publication Data
US 2020/0190093 A1   Jun. 18, 2020

(30) Foreign Application Priority Data

Dec. 12, 2018   (EP) .................................... 18212060

(51) Int. Cl.
*A61K 31/519* (2006.01)
*C07D 487/04* (2006.01)
(52) U.S. Cl.
CPC ................. *C07D 487/04* (2013.01)
(58) Field of Classification Search
CPC .......................... A61K 31/519; C07D 487/04

USPC .......................................... 514/262.1; 544/262
See application file for complete search history.

(56) References Cited

FOREIGN PATENT DOCUMENTS

WO   WO-2020120450 A1 * 6/2020   ........... C07D 473/06

OTHER PUBLICATIONS

Jordan, V. C. Nature Reviews: Drug Discovery, 2, 2003, 205.*
Hackam, et al. JAMA, 296(14), 2006, 1731-1732.*

* cited by examiner

*Primary Examiner* — Douglas M Willis
(74) *Attorney, Agent, or Firm* — Jeffrey D. Hsi

(57) ABSTRACT

The present invention relates to compounds of formula I

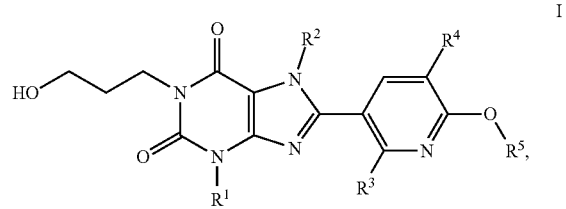

a process for their manufacture, pharmaceutical compositions containing them and their use in therapy, particularly in the treatment of conditions having an association with TRPC5 containing ion channels. $R^1$, $R^2$, $R^3$, $R^4$ and $R^5$ have meanings given in the description.

48 Claims, No Drawings

SUBSTITUTED XANTHINES AS INHIBITORS OF TRANSIENT RECEPTOR POTENTIAL CATION CHANNEL SUBFAMILY C, MEMBER 5 ACTIVITY

CROSS-REFERENCE TO RELATED APPLICATIONS

This application claims priority to European Application No. EP 18 212 060.0, filed Dec. 12, 2018, the entire contents of the aforementioned application is hereby incorporated herein by reference.

FIELD OF THE INVENTION

The present invention relates to substituted xanthine derivatives, pharmaceutical compositions containing them and their use in therapy, particularly in the treatment or prevention of conditions having an association with TRPC5 containing ion channels.

BACKGROUND OF THE INVENTION

A variety of ion channel proteins exist to mediate ion flux across cellular membranes. The proper expression and function of ion channel proteins is essential for the maintenance of cell function, and the intracellular communication. Numerous diseases are the result of mis-regulation of membrane potential or aberrant calcium handling. Given the central importance of ion channels in modulating membrane potential and ion flux in cells, identification of agents that can promote or inhibit particular ion channels are of great interest as research tools and as possible therapeutic agents.

Cation channels such as the transient receptor potential (TRP) cation channel subfamily C, member 5 (TRPC5) modulate the flux of calcium and sodium ions across cellular membranes. Sodium and calcium influx leads to a depolarization of the cell. This increases the probability that voltage-gated ion channels will reach the threshold required for activation. As a result, activation of non-selective cation channels can increase electrical excitability and increase the frequency of voltage-dependent events. Voltage-dependent events include, but are not limited to, neuronal action potentials, cardiac action potentials, smooth muscle contraction, cardiac muscle contraction, and skeletal muscle contraction.

Calcium influx caused by the activation of non-selective cation channels such as TRPC5 also alters the intracellular free calcium concentration. Calcium is a ubiquitous second messenger molecule within the cell and the alterations in intracellular calcium levels have profound effects on signal transduction and gene expression. Thus, activation of non-selective cation channels such as TRPC5 can lead to changes in gene expression and cellular phenotype. Gene expression events include, but are not limited to, production of mRNAs encoding cell surface receptors, ion channels, and kinases. These changes in gene expression can lead to hyperexcitability in that cell.

Homomeric TRPC5 ion channels are signal transduction gated, Ca2+-permeable channels predominantly expressed in neurons. TRPC5 forms homomultimeric structures such as tetramers (i.e., TRPC5 homomultimers) and heteromultimeric structures such as tetramers (i.e., TRPC5-TRPC1 heteromultimers). Unless expressly stated otherwise, when the term TRPC5 is used herein, for example, when identifying a modulator of TRPC5 such as a TRPC5 antagonist, the term TRPC5 is used generically so as to include either or both of a TRPC5 homomultimer or a heteromultimer (e.g. TRPC5-TPRC1 or TRPC5-TRPC4 heteromultimer). Examples of TRPC5 in the literature include the following: Nature 2008 Jan. 3; 451 (7174):69-72; Mol Pharmacol. 2008 January; 73 (1):42-9; J Biol Chem. 2007 Nov. 16; 282 (46):33868-78; Biochem Biophys Res Commun. 2008 Jan. 11; 365 (2):239-45; J Biol Chem. 2006 Nov. 3; 281 (44): 33487-96; Eur J Pharmacol. 2005 Mar. 14; 510 (3):217-22; J Biol Chem. 2006 Feb. 24; 281 (8):4977-82; Biochem Soc Trans. 2007 February; 35 (Pt.1):101-4; Handb Exp Pharmacol. 2007; (179):109-23; J Biol Chem. 2005 Mar. 25; 280 (12):10997-1006; J Physiol. 2006 Jan. 15; 570 (Pt 2):219-35; and Nat Neurosci. (2003) 6: 837-45.

Modulating the function of TRPC5 proteins provides a means of modulating calcium homeostasis, sodium homeostasis, membrane polarization, and/or intracellular calcium levels, and compounds that can modulate TRPC5 function are useful in many aspects, including, but not limited to, maintaining calcium homeostasis, modulating intracellular calcium levels, modulating membrane polarization, and treating or preventing diseases, disorders, or conditions associated with calcium and/or sodium homeostasis or dyshomeostasis.

Compounds inhibiting TRPC5 containing ion channels are for example useful for treating conditions such as a neuropsychiatric disorder, a neurodegenerative disorder, nephropathy, and seizure disorder by modulating the activity of the transient receptor potential cation channel subfamily C, member 5 (TRPC5), which can exist in homomultimeric form as well as heteromultimeric form with other ion channels such as TRPC1 or TRPC3 (i.e. TRPC5-TRPC1 and TRPC1-TRPC3-TRPC5). WO 2014/143799 discloses xanthine derivatives that inhibit TRPC5. They modulate the function of TRPC5 by inhibiting a TRPC5-mediated ion flux or by inhibiting the inward current, the outward current, or both currents mediated by TRPC5.

DETAILED DESCRIPTION OF THE INVENTION

The present invention provides novel substituted xanthine derivatives of formula I

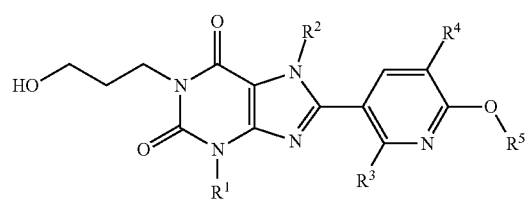

in which
$R^1$ represents ethyl, isopropyl, isobutyl, cyclobutyl;
$R^2$ represents

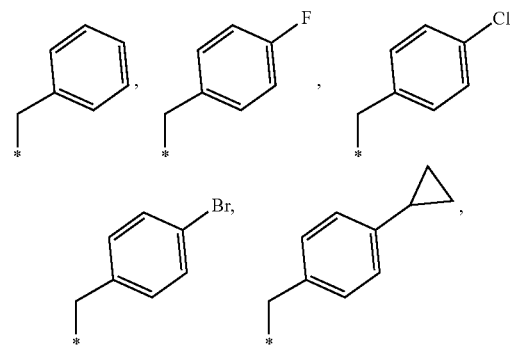

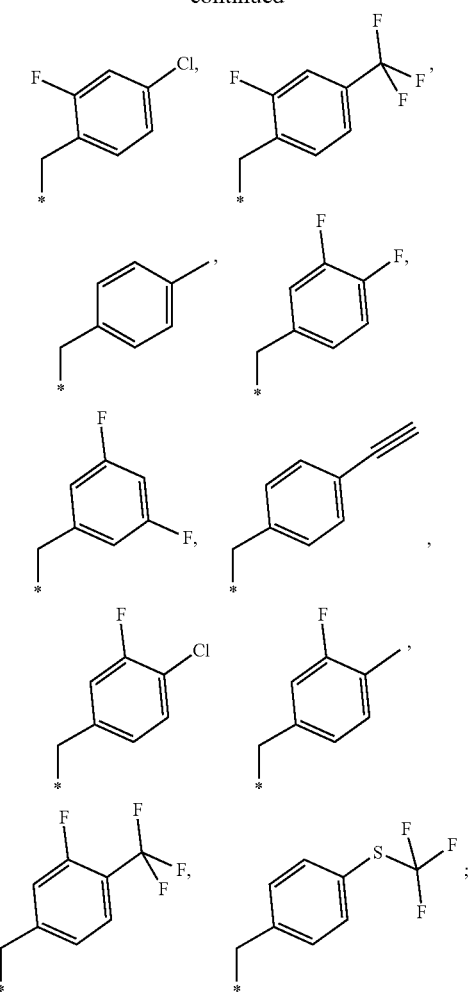

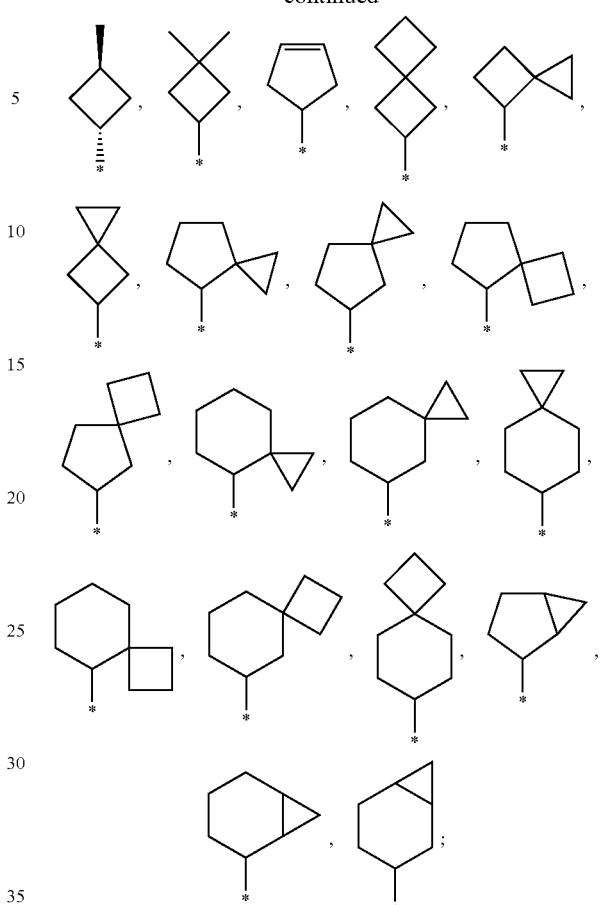

$R^3$ represents hydrogen, fluoro, $C_1$-$C_3$-alkyl optionally substituted with one or more fluorine atoms;

$R^4$ represents hydrogen or fluoro;

$R^5$ represents which groups are optionally substituted with one or more fluorine atoms and/or one or more $C_1$-$C_3$-alkyl fluorinated with one or more fluorine atoms;

or a physiologically acceptable salt thereof.

In another embodiment, in the general formula I, $R^1$ represents ethyl, isopropyl, isobutyl, cyclobutyl;

$R^2$ represents

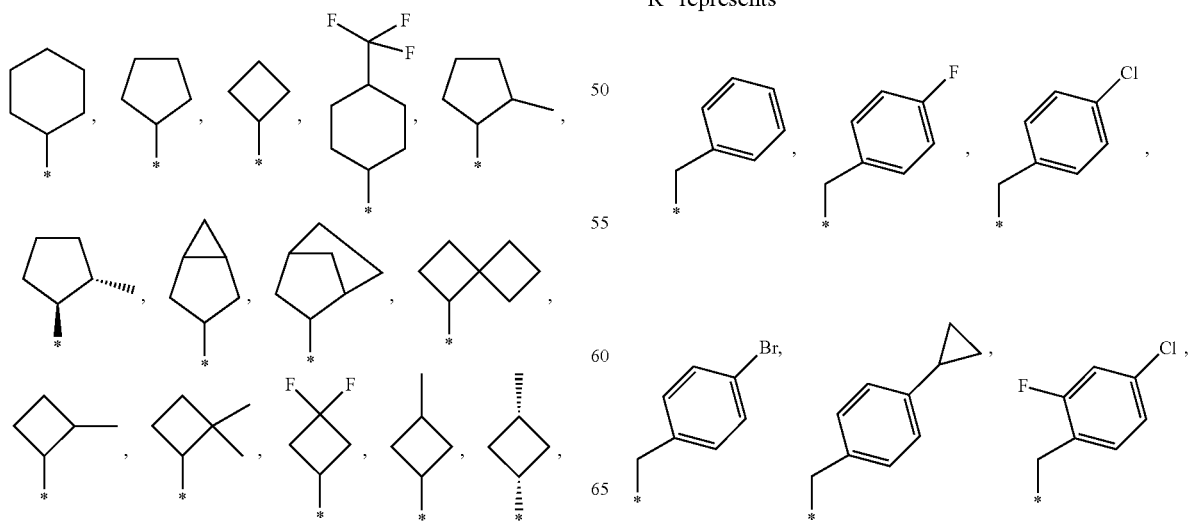

-continued

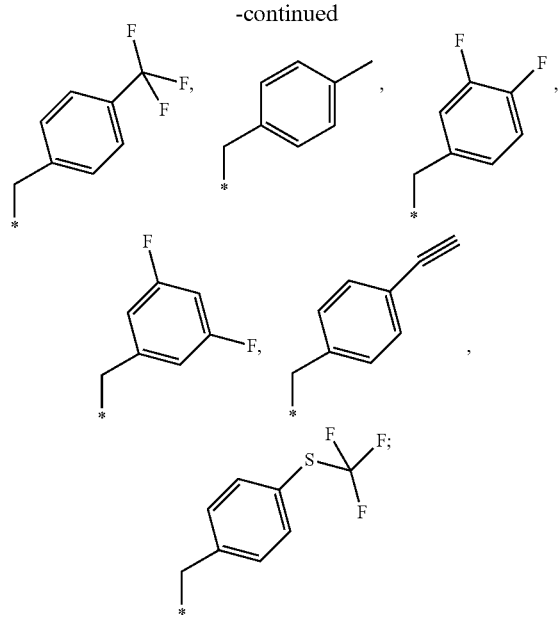

$R^3$ represents hydrogen, fluoro, methyl, ethyl, —CF$_3$;
$R^4$ represents hydrogen or fluoro;
$R^5$ represents

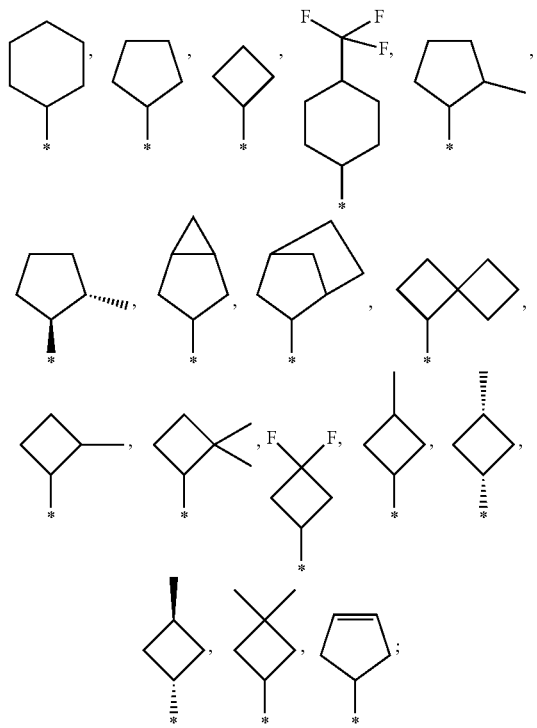

or a physiologically acceptable salt thereof.

Compounds of the present invention are potent TRPC5-inhibitors. They differ from the structurally closest compounds disclosed in WO 2014/143799 in that the C8-position of the xanthine in the compounds of the present invention is substituted with a 3-pyridyl group rather than with a phenyl group.

The compounds of the present invention modulate the function of TRPC5 by inhibiting a TRPC5-mediated ion flux or by inhibiting the inward current, the outward current, or both currents mediated by TRPC5. They are characterized by a higher potency for inhibition of TRPC5, when compared to the closest prior art compounds in WO 2014/143799.

The present invention thus provides compounds for use in the treatment of a TRPC5 mediated disorder.

The present invention further provides methods of treating a TRPC5 mediated disorder in a human subject comprising administering to the subject a compound or composition of a compound of the present invention or a pharmaceutically acceptable salt thereof.

In one aspect, the invention relates to a method for treating a condition for which reduced TRPC5 activity can reduce the severity of the condition, by administering a TRPC5 antagonist, such as a compound as described herein that inhibits a TRPC5-mediated current and/or a TRPC5-mediated ion flux. Described herein are compounds, which are TRPC5 antagonists that have a measured IC50 for inhibition of TRPC5 of 5 nanomolar or less. In certain embodiments, the compounds described herein, which are TRPC5 antagonists inhibit one or both of inward and outward TRPC5-mediated currents with an IC50 of 5 nanomolar or less. In certain embodiments, the compounds described herein inhibit at least 95% of a TRPC5-mediated current or a TRPC5-mediated ion flux when administered at 1 micromolar or less.

In another aspect, the compounds described herein, which are TRPC5 antagonists can be used to inhibit a function of TRPC5, for example a TRPC5-mediated current and/or a TRPC5-mediated ion flux. In some embodiments, the compounds described herein can be used to inhibit a TRPC5 mediated current in vitro, for example in cells in culture. In other embodiments, the compounds described herein can be used to inhibit a TRPC5 mediated current in vivo. In certain embodiments, the compounds described herein inhibit both an inward and an outward TRPC5-mediated current.

DEFINITIONS

Terms not specifically defined herein should be given the meanings that would be given to them by one skilled in the art in light of the disclosure and the context.

The terms "antagonist" and "inhibitor" are used interchangeably to refer to an agent that decreases or suppresses a biological activity, such as to repress an activity of an ion channel, such as TRPC5. TRPC5 ion channels as described herein include homomultimeric and heteromultimeric structures (e.g. homomultimeric TRPC5 and heteromeric TRPC5-TRPC1 or TRPC5-TRPC4). TRPC5 antagonists include inhibitors having any combination of the structural and/or functional properties disclosed herein.

An "effective amount" of, e.g. a TRPC5 antagonist, with respect to the subject methods of inhibition or treatment, refers to an amount of the antagonist in a preparation which, when applied as part of a desired dosage regimen brings about a desired clinical or functional result. Without being bound by theory, an effective amount of a TRPC5 antagonist for use in the methods of the present invention includes an amount of a TRPC5 antagonist effective to decrease one or more in vitro or in vivo function of a TRPC5 channel. Exemplary functions include, but are not limited to, membrane polarization (e.g. an antagonist may promote hyperpolarization of a cell), ion flux, ion concentration in a cell, outward current, and inward current. Compounds that antagonize TRPC5 function include compounds that antagonize an in vitro or in vivo functional activity of TRPC5. When a particular functional activity is only readily observable in an in vitro assay, the ability of a compound to inhibit TRPC5 function in that in vitro assay serves as a reasonable proxy for the activity of that compound. In certain embodiments, an effective amount is an amount sufficient to inhibit a TRPC5-mediated current and/or an amount sufficient to inhibit TRPC5 mediated ion flux.

The TRPC5 antagonists for use in the methods of the present invention may be characterized according to their activity, or lack of activity, against one or more other ion channels. When other ion channels are referred to, inhibition of a function of such other ion channels is defined similarly. For example, inhibition of an ion channel or an activity of an ion channel means the antagonist inhibits one or more functional activities of the other ion channel. Such functions include the current mediated by the particular ion channel, ion flux, or membrane polarization.

The terms "compound" and "agent" are used interchangeably to refer to the inhibitors/antagonists of the invention.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as 3-camphorsulfonic acid. Other resolving agents suitable for fractional crystallization methods include stereoisomerically pure forms of α-methylbenzylamine (e.g., S- and R-forms, or diastereomerically pure forms), 2-phenylglycinol, norephedrine, ephedrine, N-methylephedrine, cyclohexylethylamine, and 1,2-diaminocyclohexane.

Resolution of racemic mixtures can also be carried out by elution on a column packed with an optically active resolving agent (e.g., dinitrobenzoylphenylglycine). Suitable elution solvent composition can be determined by one skilled in the art. Compounds of the invention also include tautomeric forms, such as keto-enol tautomers.

Unless specifically indicated, throughout the specification and the appended claims, a given chemical formula or name shall encompass tautomers and all stereo, optical and geometrical isomers (e.g. enantiomers, diastereoisomers, E/Z isomers) and racemates thereof, as well as mixtures in different proportions of the separate enantiomers, mixtures of diastereoisomers, or mixtures of any of the foregoing forms where such isomers and enantiomers exist.

Compounds of the invention can also include all isotopes of atoms occurring in the intermediates or final compounds. For example, the compound of the invention may be radiolabeled with radioactive isotopes, such as for example tritium ($^3H$) or carbon-14 ($^{14}C$). All isotopic variations, whether radioactive or not, are intended to be encompassed within the scope of the present invention.

As used herein, "pharmaceutically acceptable salts" refer to derivatives of the disclosed compounds wherein the parent compound forms a salt with an acid or a base.

Examples for acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid or tartaric acid. Also included are the salts of amino acids such as arginate, and salts of organic acids like glucuronic or galactunoric acids (see, for example, Berge et al., "Pharmaceutical Salts", Journal of Pharmaceutical Science, 1977, 66, 1-19).

Examples for cations and bases forming a pharmaceutically acceptable salt with a parent compound containing an acidic moiety include $Na^+$, $K^+$, $Ca^{2+}$, $Mg^{2+}$, $NH_4^+$, L-arginine, 2,2'-iminobisethanol, L-lysine, N-methyl-D-glucamine or tris(hydroxymethyl)-aminomethane.

The neutral form of the compounds of the invention is preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The terms "TRPC5", "TRPC5 protein", and "TRPC5 channel" are used interchangeably throughout the application. Unless expressly stated, the term TRPC5 includes homomultimeric structures (e.g. homomultimeric TRPC5) and heteromultimeric structures (e.g. heteromultimeric TRPC5-TRPC1).

Biological Assays

The biological activity of compounds is determined by the following methods:

Assay A: Determination of TRPC5-Inhibition

Patch clamp experiments permit the detection of currents through the TRPC5 channel in a cell line. In normal whole-cell patch clamp recordings, a glass electrode is brought into contact with a single cell and a high-resistance (gigaohm) seal is established with the cell membrane. The membrane is then ruptured to achieve the whole-cell configuration, permitting control of the voltage of the cell membrane and measurement of currents flowing across the membrane using the amplifier attached to the electrode and resulting in the replacement of cytoplasm with the pipette solution. A perfusion system permits control of the extracellular solution, including the addition of blockers and activators of the current. The current can be activated by including 1.4 μM free Ca2+ in the pipette (intracellular) solution, and 80 μM $LaCl_3$ in the extracellular solution.

TRPC5 cells were induced 20-48 hours, removed from growth plates, and replated at low density (to attain good single-cell physical separation) on glass coverslips for measurement. In some cases, cells were grown in low density overnight on glass coverslips. Patch clamp recordings were made in the whole-cell mode with a holding potential of −40 mV. Every 5 seconds, a voltage ramp was applied from −120 to +100 mV, 400 ms in duration. Currents elicited were quantified at −80 mV and +80 mV. The internal solution consisted of 140 mM cesium aspartate, 10 mM HEDTA, 2 mM $CaCl_2$, 2.27 mM $MgCl_2$ and 10 mM HEPES, pH 7.2, with 1,400 nM calculated free Ca2+. The external solution consisted of 150 mM NaCl, 4.5 mM 15 KCl, 1 mM $MgCl_2$, 2 mM $CaCl_2$, 10 mM HEPES, 10 mM glucose, 1 mM EGTA, pH 7.4. Upon addition of $LaCl_3$, TRPC5 current was induced only in TRPC5-expressing cells and not in parental HEK293 TREx cells. Removal of the LaCh stimulus causes most of the current to go away. Potential blockers were tested for ability to block both inward and outward currents in the continued presence of $LaCl_3$.

IC50 of a compound of the invention was estimated by testing the compound 500 nM. When 500 nM of a compound showed no block, IC50 was estimated as >1 μM. Compounds blocking 50% or more at 500 nM are retested at multiple concentrations, and the % block is fitted by standard equations to determine IC50 accurately, using a 5/6 point concentration-response experiment.

Biological Data

TABLE 1

In vitro potencies of the closest prior art compounds of WO2014/143799 determined in the Assay A (described above)

| Example | Structure | Assay A TRPC5 inhibition |
|---|---|---|
| Example 441 in WO2014/143799 | *(structure)* | 324 nM |
| Example 465 in WO2014/143799 | *(structure)* | 52 nM |

Compounds of the present invention surprisingly show a much higher potency in TRPC5-inhibition when measured in the same assay (Assay A) than the closest prior art compounds (examples #441 and #465 in WO2014/143799).

The compounds of the present invention differ structurally from Examples 441 and 465 in WO 2014/143799, i.e. the closest prior art compounds, in that the C8-position of the xanthine in the presently claimed compounds is substituted with a 3-pyridyl rather than with a phenyl group as in Examples 441 and 465 of WO 2014/143799. Furthermore, the heteroaryl group in the presently claimed compounds is substituted with a cycloalkyl-O— group rather than with a methoxy-group, as in Examples 441 and 465 of WO 2014/143799. These structural differences unexpectedly result in a markedly increased potency in TRPC5-inhibition. (Tables 1 and 2).

These results demonstrate that compounds of the present invention unexpectedly are superior to the structurally most similar example disclosed in WO2014/143799 (closest prior art compounds) in TRPC5 inhibition. Consequently, compounds of the present invention are more viable for human use.

TABLE 2

In vitro potencies of compounds of the present invention determined in Assay A (described above)

| Example | Structure | Assay A TRPC5 inhibition |
|---|---|---|
| 1 | *(structure)* | <0.032 nM |

TABLE 2-continued
In vitro potencies of compounds of the present invention determined in Assay A
(described above)
| Example | Structure | Assay A TRPC5 inhibition |
|---|---|---|
| 2 | 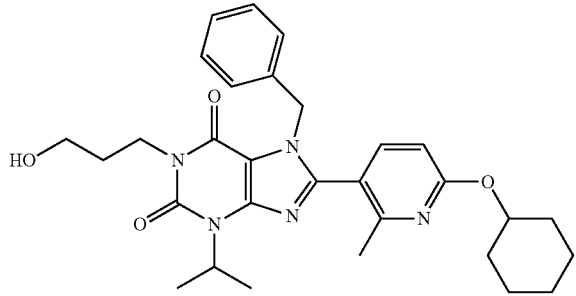 [SMILES: Cc1nc(OC2CCCCC2)ccc1-c1nc2c(c(=O)n(CCCO)c(=O)n2C(C)C)n1Cc1ccccc1] | 0.095 nM |
| 3 | 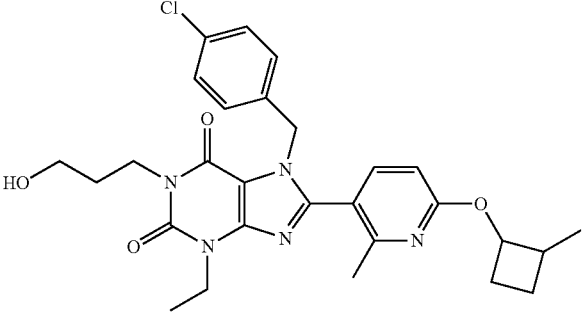 [SMILES: CCn1c(=O)n(CCCO)c(=O)c2c1nc(-c1ccc(OC3CCC3C)nc1C)n2Cc1ccc(Cl)cc1] | 0.099 nM |
| 4 | 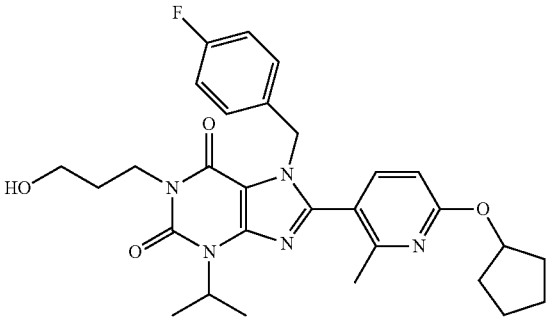 [SMILES: Cc1nc(OC2CCCC2)ccc1-c1nc2c(c(=O)n(CCCO)c(=O)n2C(C)C)n1Cc1ccc(F)cc1] | <0.1 nM |
| 5 | 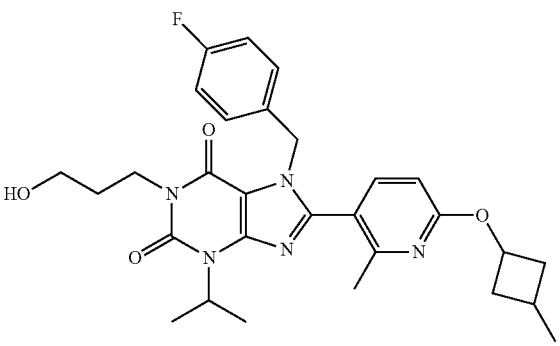 [SMILES: Cc1nc(OC2CC(C)C2)ccc1-c1nc2c(c(=O)n(CCCO)c(=O)n2C(C)C)n1Cc1ccc(F)cc1] | <0.1 nM |

TABLE 2-continued

In vitro potencies of compounds of the present invention determined in Assay A
(described above)

| Example | Structure | Assay A TRPC5 inhibition |
|---------|-----------|--------------------------|
| 6 | 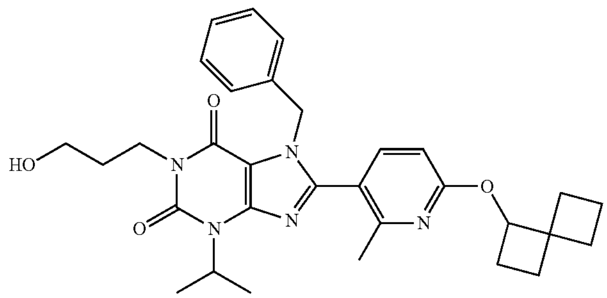 [SMILES: Cc1nc(OC2CCC23CCC3)ccc1-c1nc2c(c(=O)n(CCCO)c(=O)n2C(C)C)n1Cc1ccccc1] | <0.1 nM |
| 7 | 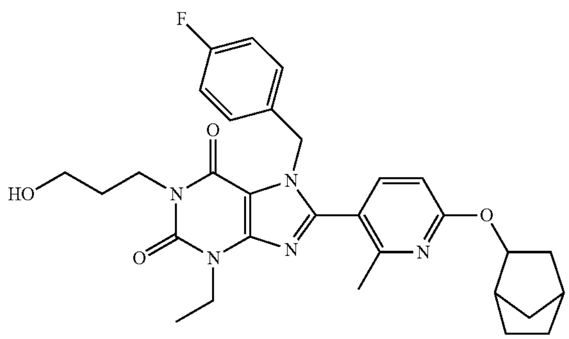 [SMILES: CCn1c(=O)n(CCCO)c(=O)c2c1nc(-c1ccc(OC3CC4CCC3C4)nc1C)n2Cc1ccc(F)cc1] | 0.104 nM |
| 8 | 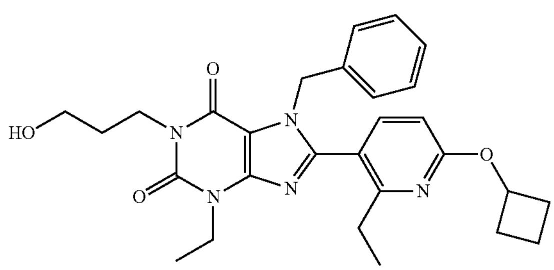 [SMILES: CCc1nc(OC2CCC2)ccc1-c1nc2c(c(=O)n(CCCO)c(=O)n2CC)n1Cc1ccccc1] | 0.106 nM |
| 9 | 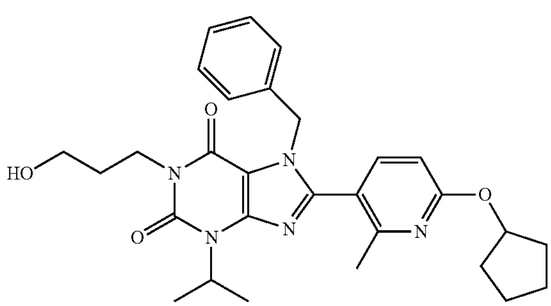 [SMILES: Cc1nc(OC2CCCC2)ccc1-c1nc2c(c(=O)n(CCCO)c(=O)n2C(C)C)n1Cc1ccccc1] | 0.130 nM |

TABLE 2-continued

In vitro potencies of compounds of the present invention determined in Assay A
(described above)

| Example | Structure | Assay A TRPC5 inhibition |
|---|---|---|
| 10 | 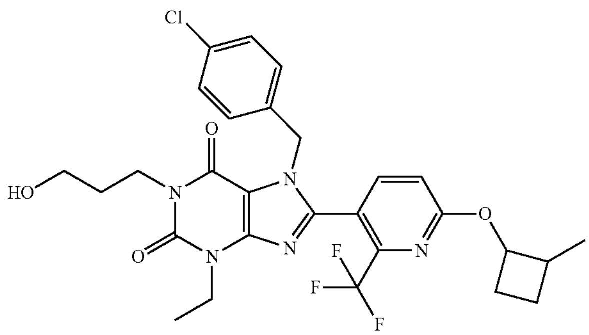 [SMILES: CCn1c(=O)n(CCCO)c(=O)c2c1nc(-c1ccc(OC3CCC3C)nc1C(F)(F)F)n2Cc1ccc(Cl)cc1] | 0.150 nM |
| 11 | 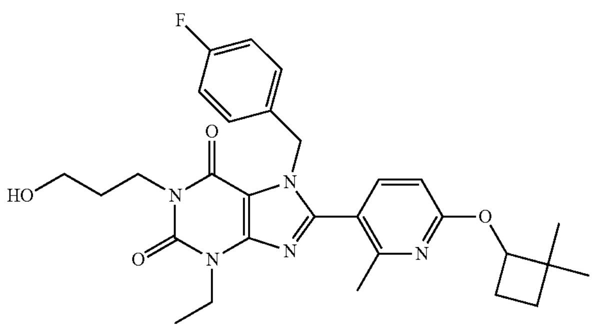 [SMILES: CCn1c(=O)n(CCCO)c(=O)c2c1nc(-c1ccc(OC3CCC3(C)C)nc1C)n2Cc1ccc(F)cc1] | 0.163 nM |
| 12 | 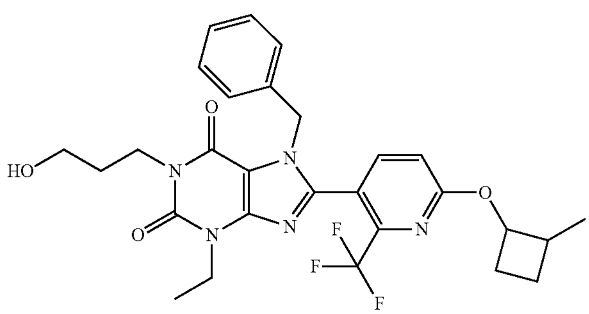 [SMILES: CCn1c(=O)n(CCCO)c(=O)c2c1nc(-c1ccc(OC3CCC3C)nc1C(F)(F)F)n2Cc1ccccc1] | 0.171 nM |
| 13 | 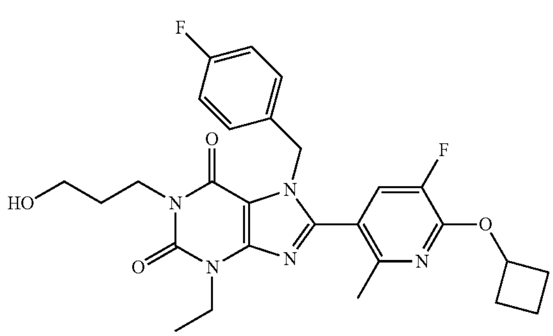 [SMILES: CCn1c(=O)n(CCCO)c(=O)c2c1nc(-c1cc(F)c(OC3CCC3)nc1C)n2Cc1ccc(F)cc1] | 0.174 nM |

TABLE 2-continued

In vitro potencies of compounds of the present invention determined in Assay A
(described above)

| Example | Structure | Assay A TRPC5 inhibition |
|---------|-----------|--------------------------|
| 14 | 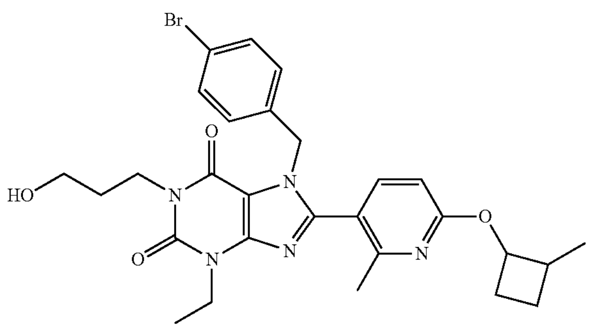 | 0.178 nM |
| 15 | 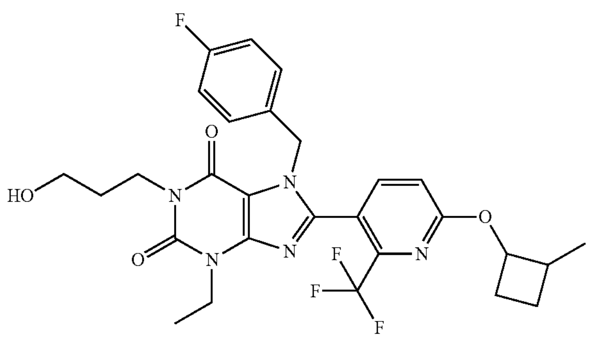 | 0.184 nM |
| 16 | 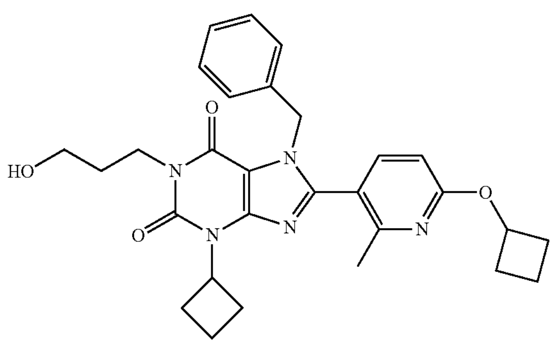 [SMILES: Cc1nc(OC2CCC2)ccc1-c1nc2c(c(=O)n(CCCO)c(=O)n2C2CCC2)n1Cc1ccccc1] | 0.190 nM |
| 17 | 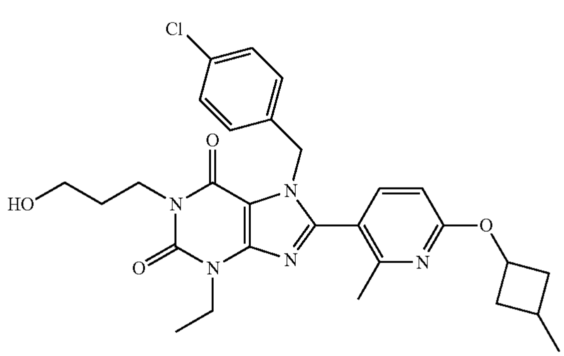 [SMILES: CCn1c(=O)n(CCCO)c(=O)c2c1nc(-c1ccc(OC3CC(C)C3)nc1C)n2Cc1ccc(Cl)cc1] | 0.199 nM |

TABLE 2-continued

In vitro potencies of compounds of the present invention determined in Assay A
(described above)

| Example | Structure | Assay A TRPC5 inhibition |
|---|---|---|
| 18 | 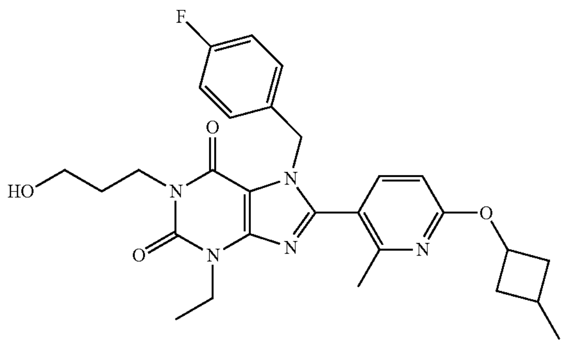 [SMILES: CCn1c(=O)n(CCCO)c(=O)c2c1nc(-c1ccc(OC3CC(C)C3)nc1C)n2Cc1ccc(F)cc1] | 0.207 nM |
| 19 | 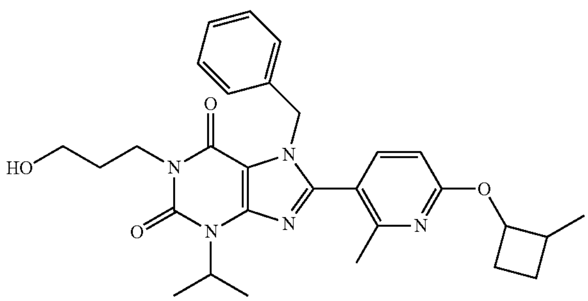 [SMILES: Cc1nc(OC2CCC2C)ccc1-c1nc2c(c(=O)n(CCCO)c(=O)n2C(C)C)n1Cc1ccccc1] | 0.236 nM |
| 20 | 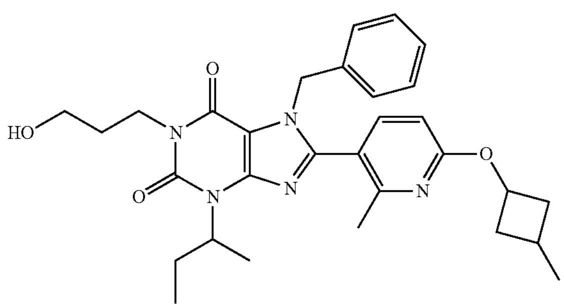 [SMILES: CCC(C)n1c(=O)n(CCCO)c(=O)c2c1nc(-c1ccc(OC3CC(C)C3)nc1C)n2Cc1ccccc1] | 0.246 nM |
| 21 | | 0.249 nM | racemic trans-mixture

TABLE 2-continued

In vitro potencies of compounds of the present invention determined in Assay A
(described above)

| Example | Structure | Assay A TRPC5 inhibition |
| --- | --- | --- |
| 22 | 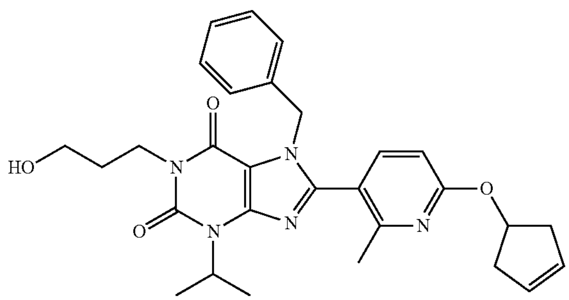 [SMILES: Cc1nc(OC2CC=CC2)ccc1-c1nc2c(c(=O)n(CCCO)c(=O)n2C(C)C)n1Cc1ccccc1] | 0.265 nM |
| 23 | 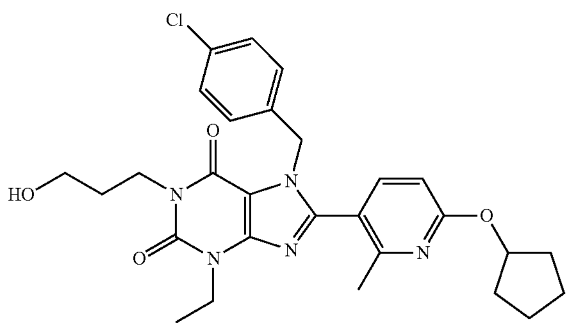 [SMILES: CCn1c(=O)n(CCCO)c(=O)c2c1nc(-c1ccc(OC3CCCC3)nc1C)n2Cc1ccc(Cl)cc1] | 0.275 nM |
| 24 | 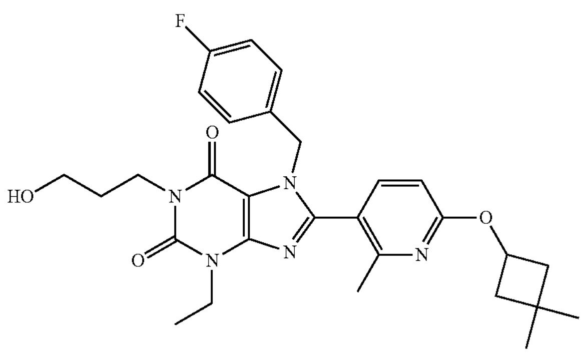 [SMILES: CCn1c(=O)n(CCCO)c(=O)c2c1nc(-c1ccc(OC3CC(C)(C)C3)nc1C)n2Cc1ccc(F)cc1] | 0.281 nM |
| 25 | 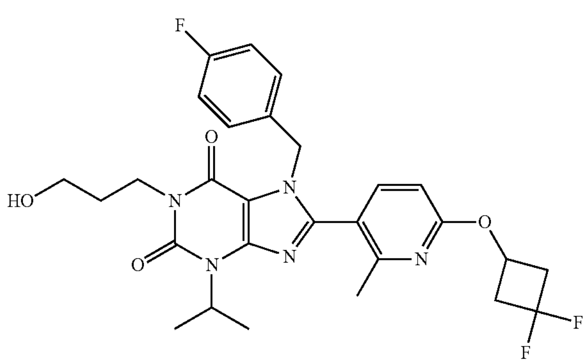 [SMILES: Cc1nc(OC2CC(F)(F)C2)ccc1-c1nc2c(c(=O)n(CCCO)c(=O)n2C(C)C)n1Cc1ccc(F)cc1] | 0.312 nM |

TABLE 2-continued

In vitro potencies of compounds of the present invention determined in Assay A
(described above)

| Example | Structure | Assay A TRPC5 inhibition |
|---------|-----------|--------------------------|
| 26 | 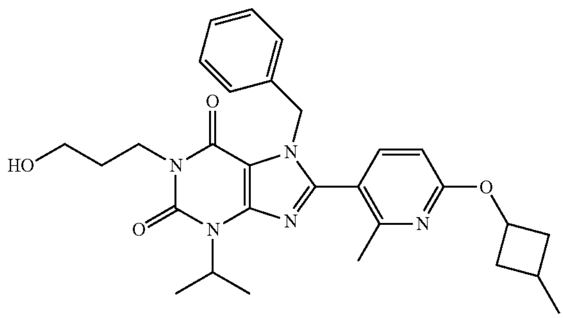 [SMILES: Cc1nc(OC2CC(C)C2)ccc1-c1nc2c(c(=O)n(CCCO)c(=O)n2C(C)C)n1Cc1ccccc1] | <0.32 nM |
| 27 | 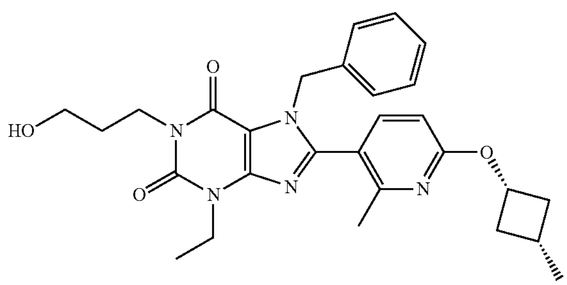 [SMILES: CCn1c(=O)n(CCCO)c(=O)c2c1nc(-c1ccc(O[C@H]3C[C@@H](C)C3)nc1C)n2Cc1ccccc1] | 0.402 nM |
| 28 | 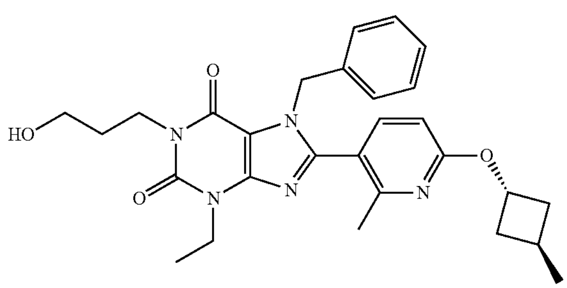 [SMILES: CCn1c(=O)n(CCCO)c(=O)c2c1nc(-c1ccc(O[C@H]3C[C@H](C)C3)nc1C)n2Cc1ccccc1] | 0.917 nM |
| 29 | 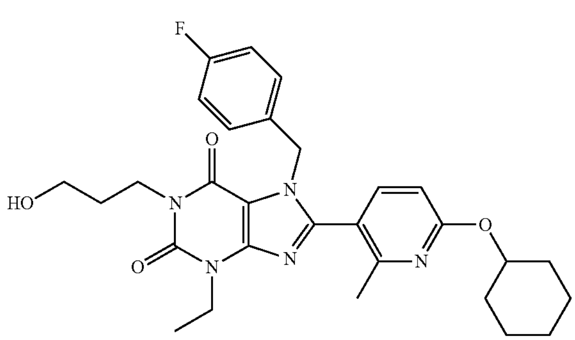 [SMILES: CCn1c(=O)n(CCCO)c(=O)c2c1nc(-c1ccc(OC3CCCCC3)nc1C)n2Cc1ccc(F)cc1] | 0.403 nM |

TABLE 2-continued

In vitro potencies of compounds of the present invention determined in Assay A
(described above)

| Example | Structure | Assay A TRPC5 inhibition |
|---|---|---|
| 30 | 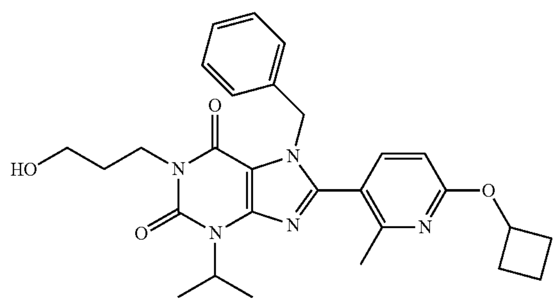 [SMILES: Cc1nc(OC2CCC2)ccc1-c1nc2c(c(=O)n(CCCO)c(=O)n2C(C)C)n1Cc1ccccc1] | 0.426 nM |
| 31 | 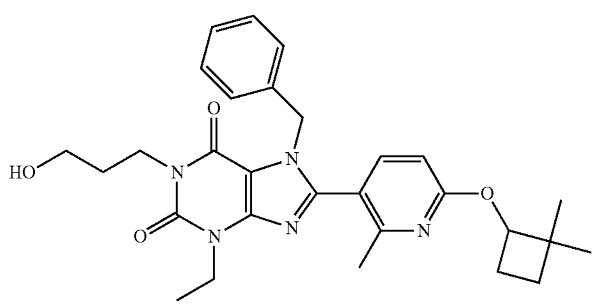 [SMILES: CCn1c(=O)n(CCCO)c(=O)c2c1nc(-c1ccc(OC3CCC3(C)C)nc1C)n2Cc1ccccc1] | 0.431 nM |
| 32 | 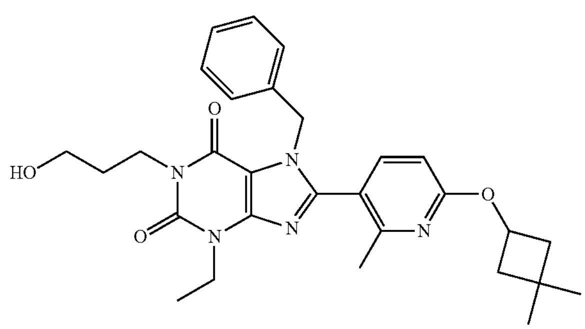 [SMILES: CCn1c(=O)n(CCCO)c(=O)c2c1nc(-c1ccc(OC3CC(C)(C)C3)nc1C)n2Cc1ccccc1] | 0.460 nM |
| 33 | 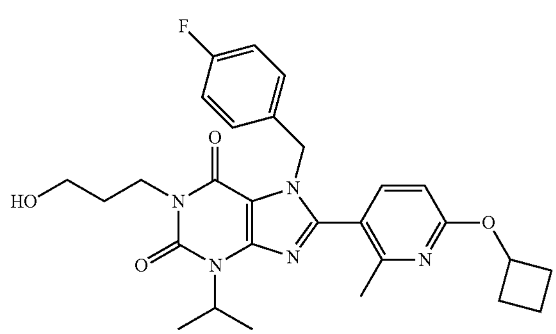 [SMILES: Cc1nc(OC2CCC2)ccc1-c1nc2c(c(=O)n(CCCO)c(=O)n2C(C)C)n1Cc1ccc(F)cc1] | 0.477 nM |

TABLE 2-continued
In vitro potencies of compounds of the present invention determined in Assay A
(described above)
| Example | Structure | Assay A TRPC5 inhibition |
|---|---|---|
| 34 | 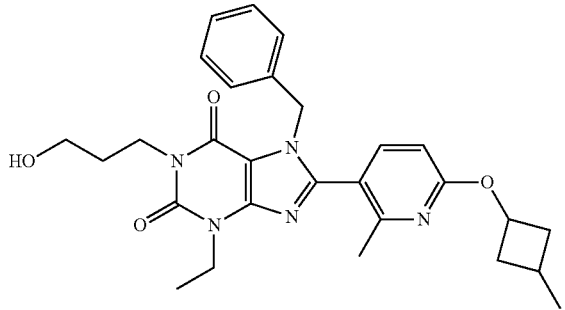 [SMILES: CCn1c(=O)n(CCCO)c(=O)c2c1nc(-c1ccc(OC3CC(C)C3)nc1C)n2Cc1ccccc1] | 0.485 nM |
| 35 | 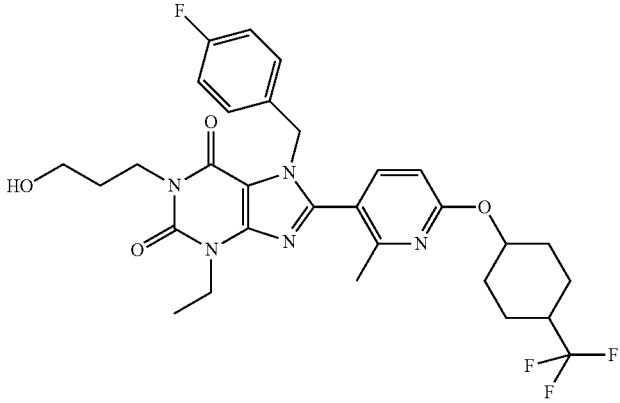 [SMILES: CCn1c(=O)n(CCCO)c(=O)c2c1nc(-c1ccc(OC3CCC(C(F)(F)F)CC3)nc1C)n2Cc1ccc(F)cc1] | 0.531 nM |
| 36 | 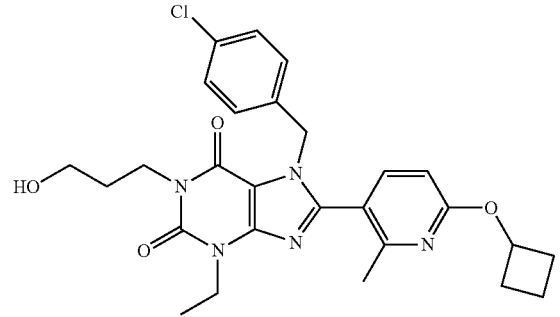 [SMILES: CCn1c(=O)n(CCCO)c(=O)c2c1nc(-c1ccc(OC3CCC3)nc1C)n2Cc1ccc(Cl)cc1] | 0.551 nM |
| 37 | 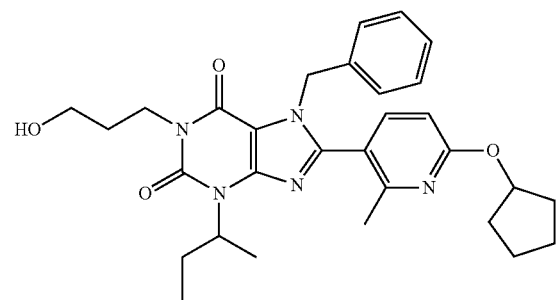 [SMILES: CCC(C)n1c(=O)n(CCCO)c(=O)c2c1nc(-c1ccc(OC3CCCC3)nc1C)n2Cc1ccccc1] | 0.603 nM |

TABLE 2-continued

In vitro potencies of compounds of the present invention determined in Assay A
(described above)

| Example | Structure | Assay A TRPC5 inhibition |
|---|---|---|
| 38 | 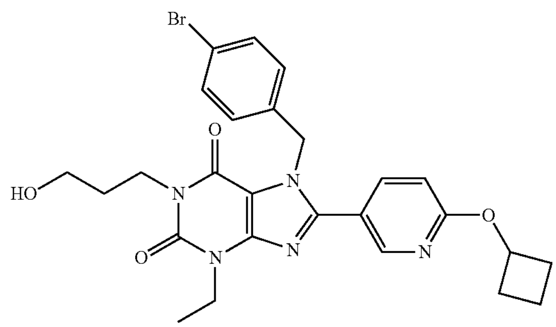 [SMILES: CCn1c(=O)n(CCCO)c(=O)c2c1nc(-c1ccc(OC3CCC3)nc1)n2Cc1ccc(Br)cc1] | 0.613 nM |
| 39 | 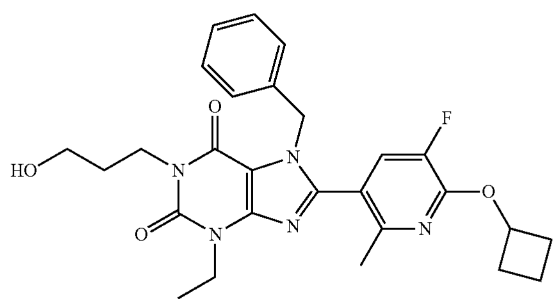 [SMILES: CCn1c(=O)n(CCCO)c(=O)c2c1nc(-c1cc(F)c(OC3CCC3)nc1C)n2Cc1ccccc1] | 0.628 nM |
| 40 | 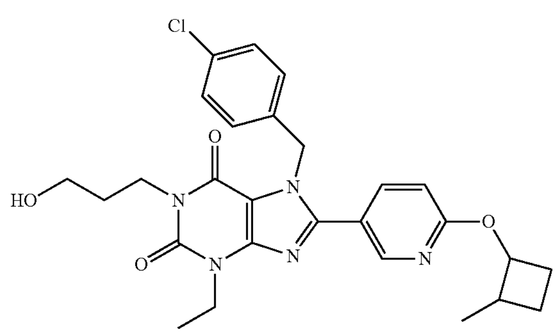 [SMILES: CCn1c(=O)n(CCCO)c(=O)c2c1nc(-c1ccc(OC3CCC3C)nc1)n2Cc1ccc(Cl)cc1] | 0.643 nM |
| 41 | 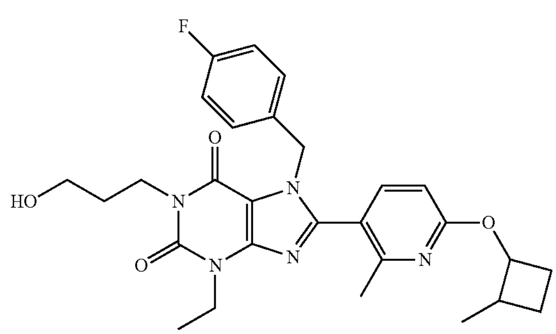 [SMILES: CCn1c(=O)n(CCCO)c(=O)c2c1nc(-c1ccc(OC3CCC3C)nc1C)n2Cc1ccc(F)cc1] | 0.688 nM |

TABLE 2-continued
*In vitro potencies of compounds of the present invention determined in Assay A (described above)*
| Example | Structure | Assay A TRPC5 inhibition |
|---|---|---|
| 42 | 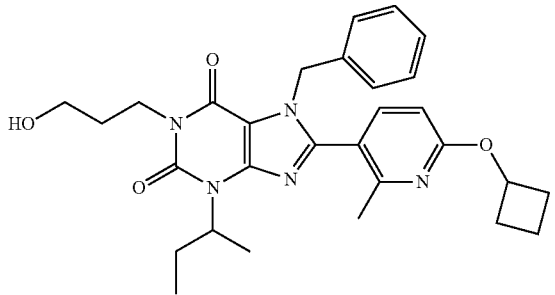 [SMILES: CCC(C)n1c(=O)n(CCCO)c(=O)c2c1nc(-c1ccc(OC3CCC3)nc1C)n2Cc1ccccc1] | 0.713 nM |
| 43 | 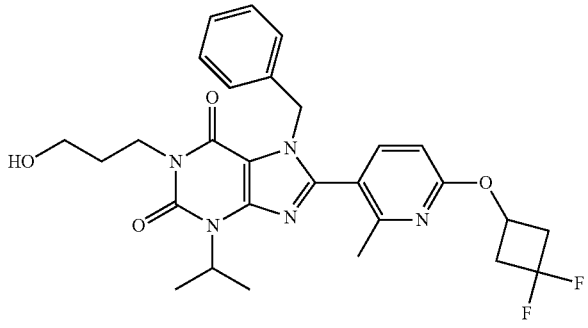 [SMILES: Cc1nc(OC2CC(F)(F)C2)ccc1-c1nc2c(c(=O)n(CCCO)c(=O)n2C(C)C)n1Cc1ccccc1] | 0.732 nM |
| 44 | 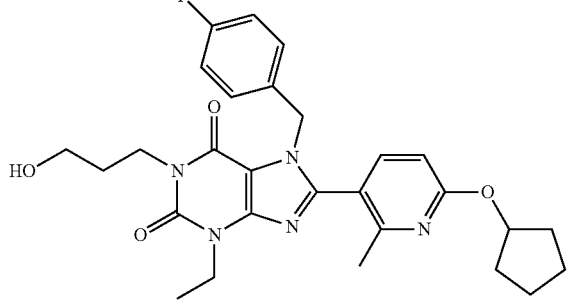 | 0.743 nM |
| 45 | 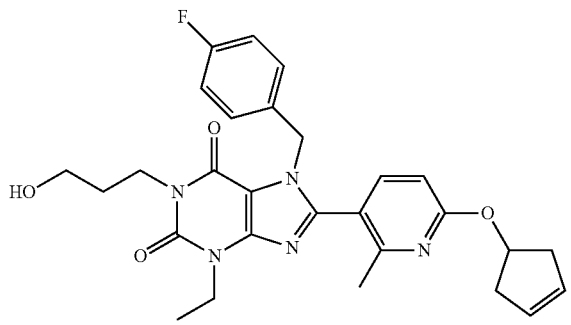 [SMILES: CCn1c(=O)n(CCCO)c(=O)c2c1nc(-c1ccc(OC3CC=CC3)nc1C)n2Cc1ccc(F)cc1] | 0.750 nM |

TABLE 2-continued

In vitro potencies of compounds of the present invention determined in Assay A
(described above)

| Example | Structure | Assay A TRPC5 inhibition |
|---------|-----------|--------------------------|
| 46 | 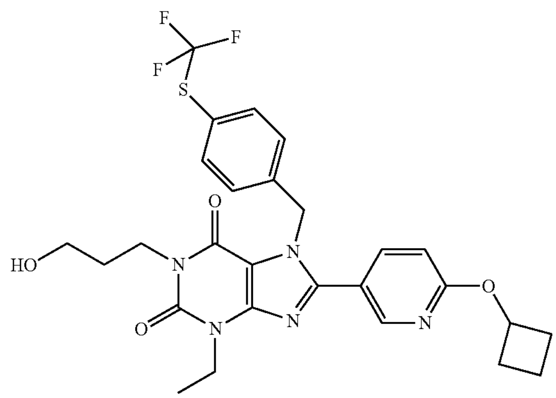 [SMILES: CCn1c(=O)n(CCCO)c(=O)c2c1nc(-c1ccc(OC3CCC3)nc1)n2Cc1ccc(SC(F)(F)F)cc1] | 0.812 nM |
| 47 | 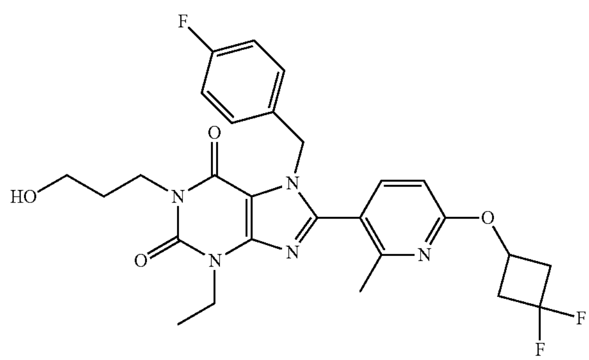 [SMILES: CCn1c(=O)n(CCCO)c(=O)c2c1nc(-c1ccc(OC3CC(F)(F)C3)nc1C)n2Cc1ccc(F)cc1] | 0.859 nM |
| 48 | 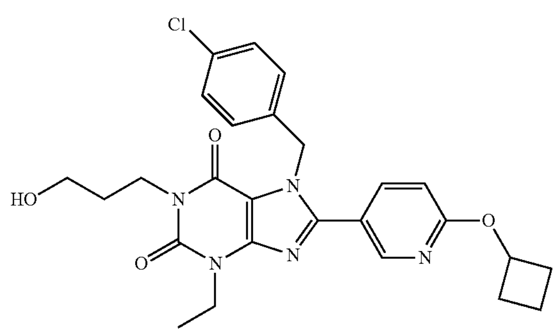 [SMILES: CCn1c(=O)n(CCCO)c(=O)c2c1nc(-c1ccc(OC3CCC3)nc1)n2Cc1ccc(Cl)cc1] | 0.873 nM |
| 49 | 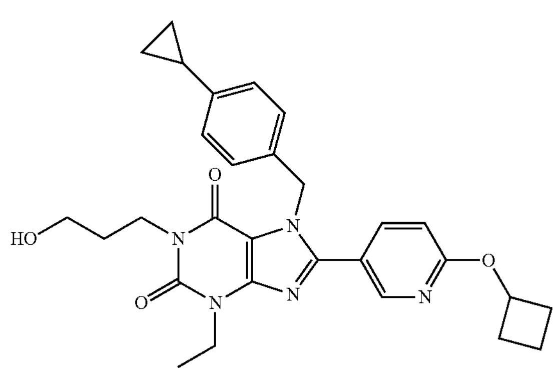 [SMILES: CCn1c(=O)n(CCCO)c(=O)c2c1nc(-c1ccc(OC3CCC3)nc1)n2Cc1ccc(C2CC2)cc1] | 1.007 nM |

TABLE 2-continued
In vitro potencies of compounds of the present invention determined in Assay A
(described above)
| Example | Structure | Assay A TRPC5 inhibition |
|---------|-----------|--------------------------|
| 50 | 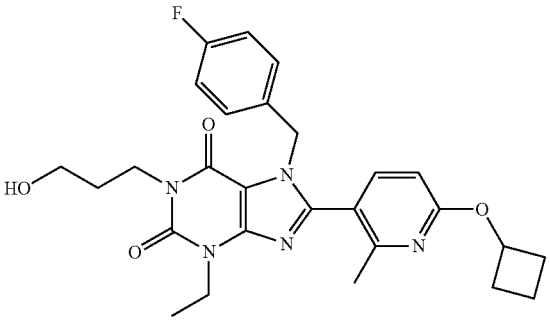 [SMILES: CCn1c(=O)n(CCCO)c(=O)c2c1nc(-c1ccc(OC3CCC3)nc1C)n2Cc1ccc(F)cc1] | 1.163 nM |
| 51 | 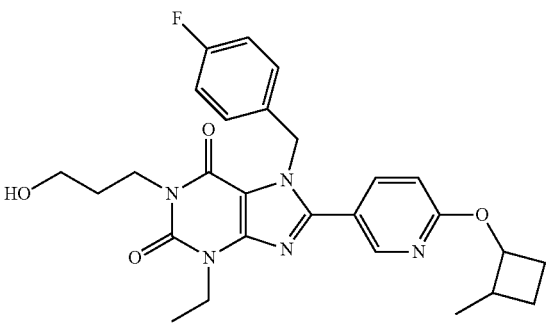 [SMILES: CCn1c(=O)n(CCCO)c(=O)c2c1nc(-c1ccc(OC3CCC3C)nc1)n2Cc1ccc(F)cc1] | 1.360 nM |
| 52 | 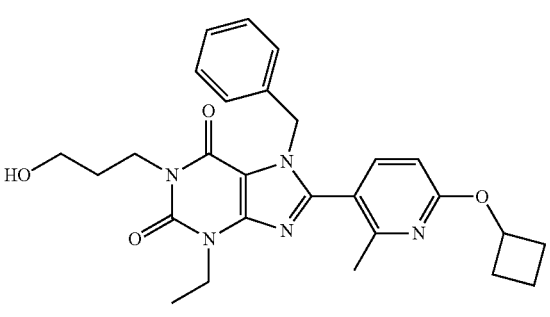 [SMILES: CCn1c(=O)n(CCCO)c(=O)c2c1nc(-c1ccc(OC3CCC3)nc1C)n2Cc1ccccc1] | 1.582 nM |
| 53 | 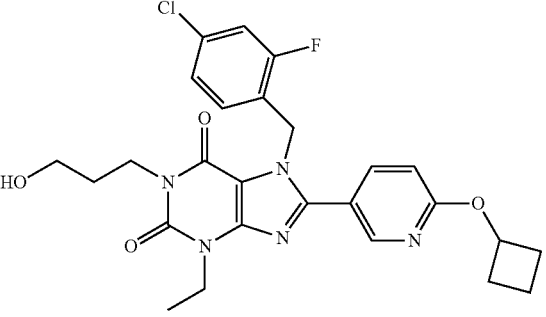 [SMILES: CCn1c(=O)n(CCCO)c(=O)c2c1nc(-c1ccc(OC3CCC3)nc1)n2Cc1ccc(Cl)cc1F] | 1.587 nM |

TABLE 2-continued
In vitro potencies of compounds of the present invention determined in Assay A
(described above)
| Example | Structure | Assay A TRPC5 inhibition |
|---|---|---|
| 54 | 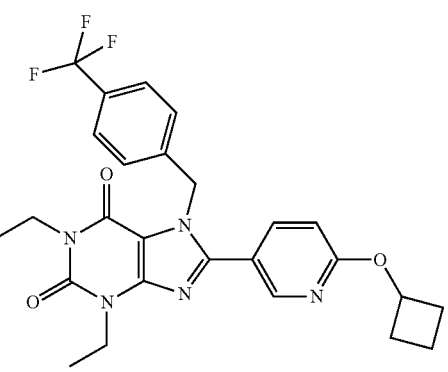 | 1.601 nM |
| 55 | 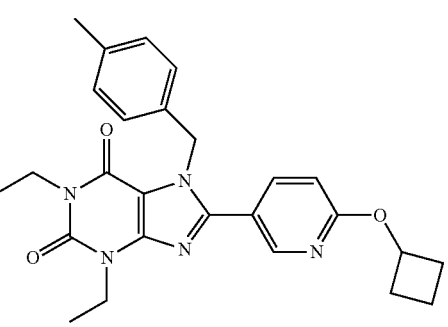 | 2.162 nM |
| 56 | 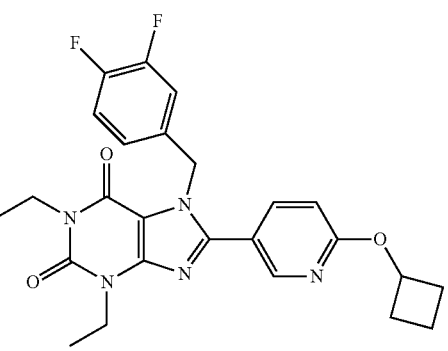 | 2.643 nM |
| 57 | 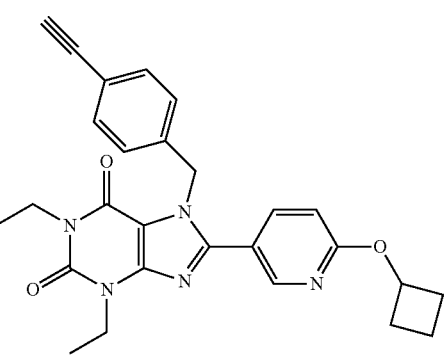 | 2.663 nM |

TABLE 2-continued

In vitro potencies of compounds of the present invention determined in Assay A
(described above)

| Example | Structure | Assay A TRPC5 inhibition |
|---------|-----------|--------------------------|
| 58 | 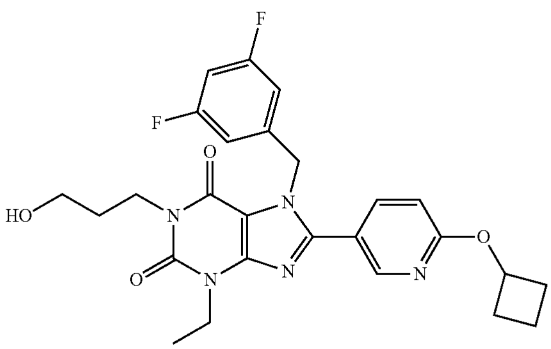 [SMILES: CCn1c(=O)n(CCCO)c(=O)c2c1nc(-c1ccc(OC3CCC3)nc1)n2Cc1cc(F)cc(F)c1] | 3.668 nM |
| 59 | 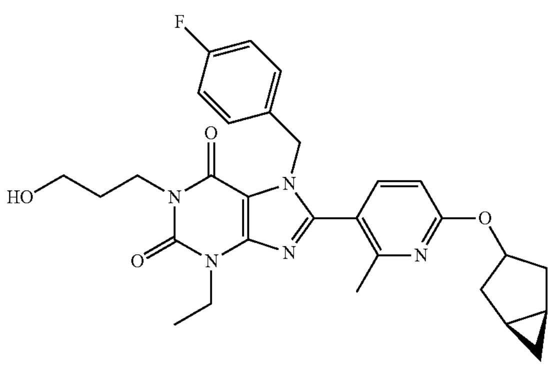 [SMILES: CCn1c(=O)n(CCCO)c(=O)c2c1nc(-c1ccc(OC3C[C@@H]4C[C@@H]4C3)nc1C)n2Cc1ccc(F)cc1] | 1.727 nM |
| 60 | 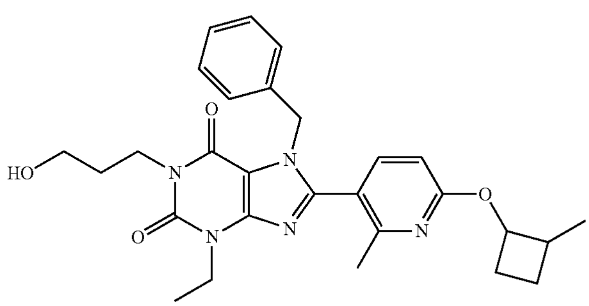 [SMILES: CCn1c(=O)n(CCCO)c(=O)c2c1nc(-c1ccc(OC3CCC3C)nc1C)n2Cc1ccccc1] | 2.094 nM |
| 61 | 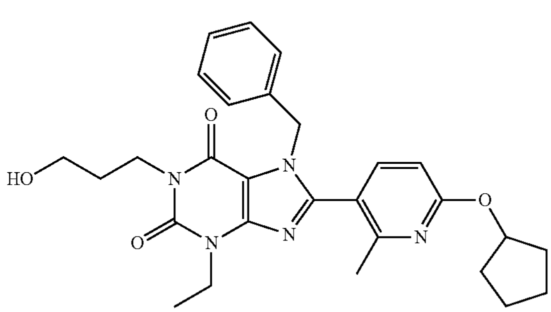 [SMILES: CCn1c(=O)n(CCCO)c(=O)c2c1nc(-c1ccc(OC3CCCC3)nc1C)n2Cc1ccccc1] | 2.426 nM |

TABLE 2-continued

In vitro potencies of compounds of the present invention determined in Assay A
(described above)

| Example | Structure | Assay A TRPC5 inhibition |
|---|---|---|
| 62 | 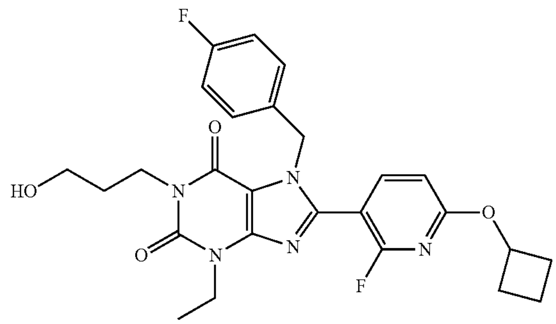 [SMILES: CCn1c(=O)n(CCCO)c(=O)c2c1nc(-c1ccc(OC3CCC3)nc1F)n2Cc1ccc(F)cc1] | 3.369 nM |
| 63 | 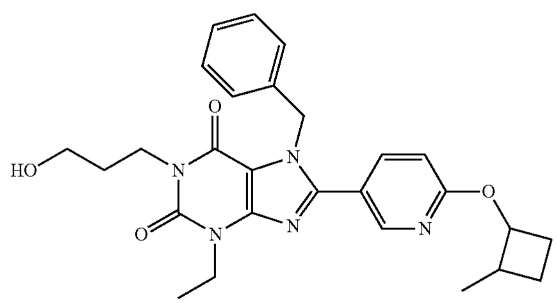 [SMILES: CCn1c(=O)n(CCCO)c(=O)c2c1nc(-c1ccc(OC3CCC3C)nc1)n2Cc1ccccc1] | 3.155 nM |
| 64 | 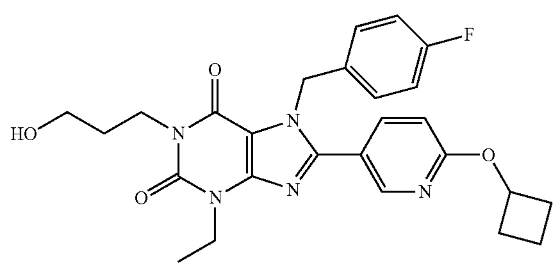 [SMILES: CCn1c(=O)n(CCCO)c(=O)c2c1nc(-c1ccc(OC3CCC3)nc1)n2Cc1ccc(F)cc1] | 2.715 nM |

Use in Treatment Method of Use

The present invention is directed to compounds which are useful in the treatment of a disease, disorder and condition wherein the inhibition of the activity of the transient receptor potential cation channel TRPC5 is of therapeutic benefit. This includes but is not limited to the treatment and/or prevention of psychiatric, neurological or neurodegenerative conditions, pain, seizure, non-neuronal conditions, and cancer.

Psychiatric conditions include diseases associated with dysregulated emotional processing (e.g. borderline personality disorder or depressive disorders like major depression, major depressive disorder, psychiatric depression, dysthymia, and postpartum depression, and bipolar disorders), anxiety and fear-related disorders (e.g. post-traumatic stress disorder, panic disorder, agoraphobia, social phobias, generalized anxiety disorder, panic disorder, social anxiety disorder, obsessive compulsive disorder, and separation anxiety), memory disorders (e.g. Alzheimer's disease, amnesia, aphasia, brain injury, brain tumor, chronic fatigue syndrome, Creutzfeldt-Jakob disease, dissociative amnesia, fugue amnesia, Huntington's disease, learning disorders, sleeping disorders, multiple personality disorder, pain, post-traumatic stress disorder, schizophrenia, sports injuries, stroke, and Wernicke-Korsakoff syndrome), disorders associated with impaired impulse control and addiction.

Neurological or neurodegenerative conditions include e.g. Alzheimer's disease (AD), Parkinson's disease, Huntington's disease, amyotrophic lateral sclerosis (ALS), and other brain disorders caused by trauma or other insults including aging.

Pain disorders include nociceptive pain, inflammatory pain, cancer pain, and neuropathic pain (e.g. cancer pain, osteoarthritic pain, rheumatoid arthritis pain, post-herpetic neuralgia, pain due to burns, and other indications). The pain can be chronic or acute.

Seizures may be induced by excitotoxicity of a variety of origins. Commonly excess neuronal firing can drive seizure activity. Compounds that reduce the hyperexcitability of relevant neuronal populations have significant potential in reducing seizure activity. Compounds of the invention that inhibit TRPC5 may reduce hyperexcitability and thus reduce seizure activity.

Non-neuronal conditions include nephropathy, proteinuric kidney disease, liver diseases such as hepatic dyslipidemia associated with cholestasis, non-alcoholic steatohepatitis (NASH), non-alcoholic fatty liver disease (NAFLD) [WO2018/146485], itch, disorders associated with malfunction of the cardiovascular-vascular system or vascular permeability (e.g. pulmonary arterial hypertension, acute respiratory distress syndrome (ARDS), maladaptive cardiac remodeling, disorders associated with maladaptive blood pressure control like hypertension or hypotension, and other medical conditions such as diabetes, insulin resistance, metabolic syndrome and obesity. It is envisaged that the use for treatment of non-neuronal conditions may also extend to the use for cosmetic weight loss (WO02018/146485).

Another aspect of the invention relates to pharmaceutical compositions for use in a human patient, comprising an effective amount of a compound described herein (or a pharmaceutically acceptable salt thereof), and one or more pharmaceutically acceptable excipient(s). The invention further contemplates the use of the compounds described herein in the manufacture of a medicament or a pharmaceutical composition to treat or reduce the symptoms of any of the diseases or conditions provided in the specification. The compounds described herein can be used for treating a particular disease or condition and can be formulated for administration via a route appropriate for the particular disease or condition.

The applicable daily dose of compounds of the present invention may vary from 0.1 to 2000 mg. The actual pharmaceutically effective amount or therapeutic dose will depend on factors known by those skilled in the art such as age and weight of the patient, route of administration and severity of disease. In any case, the drug substance is to be administered at a dose and in a manner which allows a pharmaceutically effective amount to be delivered that is appropriate to the patient's condition.

Pharmaceutical Compositions

Suitable compositions for administering the compounds of the present invention will be apparent to those with ordinary skill in the art and include for example tablets, pills, capsules, suppositories, lozenges, troches, solutions, syrups, elixirs, sachets, injectables, inhalatives, and powders. The content of the pharmaceutically active compound(s) may vary in the range from 0.1 to 95 wt.-%, preferably 5.0 to 90 wt.-% of the composition as a whole.

Suitable tablets may be obtained, for example, by mixing a compound of the present invention with known excipients, for example inert diluents, carriers, disintegrants, adjuvants, surfactants, binders and/or lubricants and compressing the resulting mixture to tablets.

Combination Therapy

The compounds of the present invention can be used alone or in combination with other active pharmaceutical ingredients. In particular, compounds according to the present invention can be combined with other treatment options known to be used in the art in connection with a treatment of any of the indications the treatment of which is in the focus of the present invention.

Among such active pharmaceutical ingredients or treatment options that are considered suitable for combination with the compounds and the treatment according to the present invention are antidepressants, mood stabilizers, typical and atypical antipsychotics, anxiolytics, antiepileptic drugs, sleeping agents, cognitive enhancers, stimulants, additional psychoactive drugs, anti-inflammatory drugs, analgesic drugs, chemotherapeutic drugs as well as active pharmaceutical ingredients used or potentially useful in the treatment of metabolic disorders, liver diseases and kidney diseases, the latter active pharmaceutical ingredients also including potential inhibitors of TRPC3 and/or TRPC6.

EXPERIMENTAL SECTION

List of Abbreviations

ACN acetonitrile
conc concentrated
d day(s)
DCM dichloromethane
DIPEA N-ethyl-diisopropylamine
DMAP 4-dimethylaminopyridine
DMF N,N-dimethylformamide
DMSO dimethylsulfoxide
EtOAc ethyl acetate
g gram
h hour(s)
HOAc acetic acid
HPLC high performance liquid chromatography
MeOH Methanol
min minute(s)
mg milligram
mL milliliter
N normal
rt room temperature
RT retention time
SFC supercritical fluid chromatography
THF tetrahydrofuran
TFA trifluoroacetic acid
µL microliter
HPLC-Methods:
Method Name: A
Column: XBridge BEH C18_2.1×30 mm, 1.7 µm
Column Supplier: Waters

| Gradient/Solvent Time [min] | % Sol [H$_2$O, 0.1% TFA] | % Sol [ACN] | Flow [mL/min] | Temp [° C.] |
|---|---|---|---|---|
| 0.00 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

Method Name: B
Column: XBridge BEH Phenyl, 2.1×30 mm, 1.7 µm
Column Supplier: Waters

| Gradient/Solvent Time [min] | % Sol [H$_2$O, 0.1% NH$_3$] | % Sol [Acetonitril] | Flow [mL/min] | Temp [° C.] |
|---|---|---|---|---|
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

Method Name: C
Column: XBridge C18, 4.6×30 mm, 3.5 µm
Column Supplier: Waters

| Gradient/Solvent Time [min] | % Sol [H$_2$O, 0.1% NH$_3$] | % Sol [ACN] | Flow [mL/min] | Temp [° C.] |
|---|---|---|---|---|
| 0.00 | 97 | 3 | 5 | 60 |
| 0.02 | 97 | 3 | 5 | 60 |
| 1.60 | 0 | 100 | 5 | 60 |
| 1.70 | 0 | 100 | 5 | 60 |

Method Name: D
Column: XBridge BEH C18, 2.1×30 mm, 1.7 μm
Column Supplier: Waters

| Gradient/Solvent Time [min] | % Sol [H₂O, 0.1% NH₃] | % Sol [ACN] | Flow [mL/min] | Temp [° C.] |
|---|---|---|---|---|
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

Method Name: E
Column: XBridge BEH C18_2.1×30 mm_2.5 μm
Column Supplier: Waters

| Gradient/Solvent Time [min] | % Sol [H₂O, 0.1% NH₃] | % Sol [ACN] | Flow [mL/min] | Temp [° C.] |
|---|---|---|---|---|
| 0.00 | 50 | 50 | 1.3 | 60 |
| 0.02 | 50 | 50 | 1.3 | 60 |
| 1.00 | 0 | 100 | 1.3 | 60 |
| 1.10 | 0 | 100 | 1.3 | 60 |

Method Name: F
Column: Sunfire C18_3.0×30 mm_2.5 μm
Column Supplier: Waters

| Gradient/Solvent Time [min] | % Sol [H₂O, 0.1% TFA (v/v)] | % Sol [ACN] | Flow [mL/min] | Temp [° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |

Method Name: G
Column: XBridge BEH C18_2.1×30 mm_2.5 μm
Column Supplier: Waters

| Gradient/Solvent Time [min] | % Sol [H₂O, 0.1% NH₃] | % Sol [ACN] | Flow [mL/min] | Temp [° C.] |
|---|---|---|---|---|
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

Method Name: H
Column: XBridge BEH C18_2.1×30 mm_1.7 μm
Column Supplier: Waters

| Gradient/Solvent Time [min] | % Sol [H₂O, 0.1% NH₃] | % Sol [ACN] | Flow [mL/min] | Temp [° C.] |
|---|---|---|---|---|
| 0.00 | 50 | 50 | 1.3 | 60 |
| 0.02 | 50 | 50 | 1.3 | 60 |
| 1.00 | 0 | 100 | 1.3 | 60 |
| 1.10 | 0 | 100 | 1.3 | 60 |

Method Name: I
Column: Lux® Cellulose_3 4.6×250 mm_5 μm
Column Supplier: Phenomenex

| Gradient/Solvent Time [min] | % Sol [scCO₂] | % Sol [MEOH 20 mM NH₃] | Flow [mL/min] | Temp [° C.] | Back pressure (PSI) |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

Method Name: J
Column: Chiralpak® IA_4.6×250 mm_5 μm
Column Supplier: Daicel

| Gradient/Solvent Time [min] | % Sol [scCO₂] | % Sol [MEOH 20 mM NH₃] | Flow [mL/min] | Temp [° C.] | Back pressure (PSI) |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Method Name: K
Column: Lux® Amylose-2_4.6×250 mm_5 μm
Column Supplier: Phenomenex

| Gradient/Solvent Time [min] | % Sol [scCO₂] | % Sol [MEOH 20 mM NH₃] | Flow [mL/min] | Temp [° C.] | Back pressure (PSI) |
|---|---|---|---|---|---|
| 0.0 | 95.0 | 5.0 | 4.0 | 40.0 | 2175.0 |
| 10.0 | 95.0 | 5.0 | 4.0 | 40.0 | 2175.0 |

NMR method: NMR spectra were recorded on a Bruker AVANCE IIIHD 400 MHz instrument using TopSpin 3.2 pl6 software. Chemical shifts are given in parts per million (ppm) downfield from internal reference trimethylsilane in δ units. Selected data are reported in the following manner: chemical shift (multiplicity, coupling constants (J), number of hydrogens). Abbreviations are as follows: s (singulet), d (doublet), t (triplet), q (quartet), spt (septet), m (multiplet), br (broad).

Intermediates

Intermediate 1.1

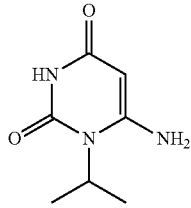

1.1

The reaction was performed under argon atmosphere and in dried glassware. Sodium [metal] (4.50 g, 196 mmol) was added in pieces to dry propan-2-ol (150 mL). The mixture was stirred 2 h and heated to 95° C. After the sodium was completely dissolved, isopropyl-urea (10.0 g, 97.9 mmol) and cyano-acetic acid ethyl ester (10.4 mL, 97.9 mmol) were added and the mixture was stirred overnight at 95° C. The mixture was cooled down and H₂O (40.0 mL) was added and the pH was adjusted to 6 with conc HCl. Stirring was continued under ice cooling and N₂ atmosphere for 12 h. The obtained precipitate was filtered and dried to obtain 7.33 g of the product.

MS (ESI+): (M+H)+ 170
HPLC: RT=0.23 min, Method F

Intermediate 1.2

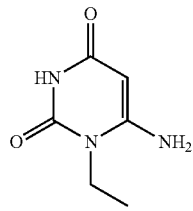

1.2

The reaction was performed under argon atmosphere and in dried glassware. Sodium (metal) (20.9 g, 908 mmol) was added in pieces to dry ethanol (600 mL). The mixture was stirred 3 d and heated to 60° C. After the sodium was completely dissolved, ethylurea (40.0 g, 454 mmol) and ethyl 2-cyanoacetate (48.3 mL, 454 mmol) were added and the mixture was stirred 4 d at reflux. The mixture was concentrated in vacuo, H$_2$O (200 mL) was added and the pH was adjusted to 7 with conc HCl. Stirring was continued under ice cooling for 30 min. The obtained precipitate was filtered, washed with H$_2$O and dried to obtain 48.59 g of the product.

MS (ESI+): (M+H)+ 156
HPLC: RT=1.18 min, Method B

Intermediate 1.3

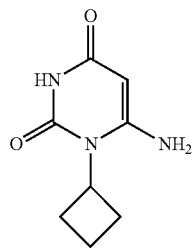

1.3

The reaction was performed under nitrogen atmosphere and in dried glassware. Sodium (metal) (0.6 g, 26.3 mmol) was added in pieces to dry propan-2-ol (20 mL). The mixture was stirred 1 h at 60° C. Then EtOH (5 mL, 60.7 mmol) was added and the mixture was stirred 30 min at 60° C. After the sodium was completely dissolved, cyclobutylurea (1.5 g, 13.1 mmol) and ethyl 2-cyanoacetate (1.4 mL, 13.1 mmol) were added and the mixture was stirred overnight at reflux. The mixture was concentrated in vacuo, H$_2$O (5.0 mL) was added and the pH was adjusted to 7 with conc HCl. Stirring was continued under ice cooling and N$_2$ atmosphere for 45 min. The obtained precipitate was filtered and dried to obtain 1.61 g of the product.

MS (ESI+): (M+H)+ 182
HPLC: RT=0.31 min, Method F

Intermediate 2.1

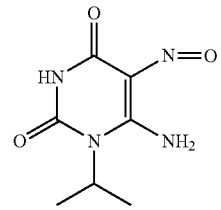

2.1

To a mixture of intermediate 1.1 (1.00 g, 5.91 mmol) in HCl (1 mol/l, 16.5 mL, 16.5 mmol) NaNO$_2$ (571 mg, 8.28 mmol) in H$_2$O (6.00 mL) was added dropwise. NaOH (4 N, about 4 mL) was added until the pH of the solution reached pH=9. The obtained precipitate was filtered, washed with MeOH and tert-butylmethylether and dried to obtain 0.79 g of the product.

MS (ESI+): (M+H)+ 199
HPLC: RT=0.24 min, Method F

Intermediate 2.2

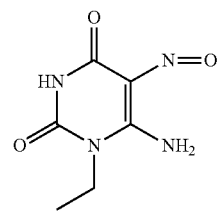

2.2

To a mixture of intermediate 1.2 (48.6 g, 0.304 mol) in HCl (1 mol/l, 800 mL, 800 mmol) NaNO$_2$ (29.3 g, 0.425 mol) in H$_2$O (280 mL) was added dropwise. The mixture was stirred overnight at rt. Then the mixture was basified with NaOH (60%, about 15 mL). The obtained precipitate was filtered, washed with MeOH and tert-butylmethylether and dried to obtain 43.8 g of the product.

MS (ESI+): (M+H)+ 185
HPLC: RT=0.09 min, Method B

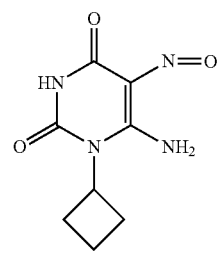

2.3

Intermediate 2.3

To a mixture of intermediate 1.3 (2.31 g, 0.013 mol) in HCl (1 mol/l, 16.5 mL, 16.5 mmol) NaNO$_2$ (1.23 g, 0.018 mol) in H$_2$O (6 mL) was added dropwise. Then the mixture was neutralised with NaOH (4N). The obtained precipitate was filtered, washed with H₂O and tert-butylmethylether and dried to obtain 2.27 g of the product.

MS (ESI+): (M+H)+ 211
HPLC: RT=0.30 min, Method F

Intermediate 3.1

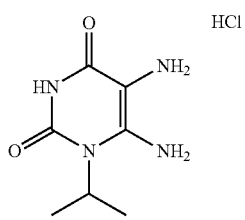

3.1

A mixture of intermediate 2.1 (8.04 g, 40.6 mmol), Pd/C (10%, 1.9 g), MeOH (120 mL), H₂O (80 mL) and HCl solution (4 mol/L, 11.2 mL, 44.6 mmol) was hydrogenated at rt and 50 psi of H₂ for 4 h. The mixture was filtered, MeOH was evaporated, ACN was added and freeze dried to obtain 3.04 g of the product.

MS (ESI⁺): (M+H)⁺ 185
HPLC: RT=0.01 min, Method D

Intermediate 3.2

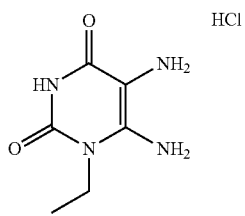

3.2

A mixture of intermediate 2.2 (43.3 g, 235 mmol), Pd/C (10%, 4.95 g), MeOH (400 mL), H₂O (300 mL) and HCl solution (1 mol/L, 259 mL, 259 mmol) was hydrogenated at rt and 50 psi of H₂ for 1 d. The mixture was filtered, MeOH was evaporated, ACN was added and freeze dried to obtain 47.2 g of the product.

MS (ESI⁺): (M+H)⁺ 169/171
HPLC: RT=0.08/0.1 min, Method B

Intermediate 3.3

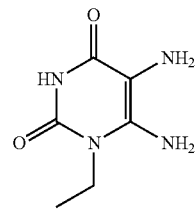

3.3

A mixture of intermediate 2.2 (31.0 g, 109 mmol), Pd/C (10%, 3.0 g), MeOH (270 mL), H₂O (207 mL) and HCl solution (1 mol/L, 185 mL, 185 mmol) was hydrogenated at rt and 50 psi of H₂ for 1.5 d (temperature increased to 50° C.). The mixture was filtered, MeOH was evaporated and freeze dried. The residue was dissolved in H₂O (390 mL) and NaHCO₃ was added until the pH reached 6-7. The obtained precipitate was filtered, washed with cold H₂O and tert-butylmethylether and dried to give 15.6 g of the product.

MS (ESI⁺): (M+H)⁺ 171
HPLC: RT=0.14 min, Method F

Intermediate 3.4

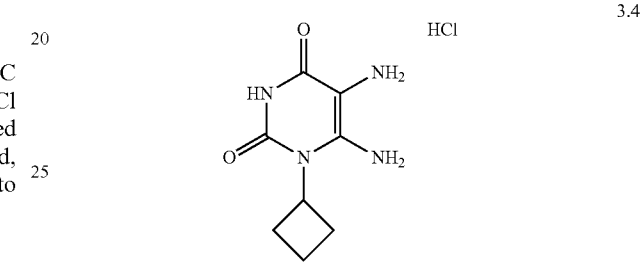

3.4

A mixture of intermediate 2.3 (1.0 g, 4.76 mmol), Pd/C (10%, 115 mg), MeOH (15 mL), H₂O (7.5 mL) and HCl solution (1 mol/L, 5.23 mL, 5.23 mmol) was hydrogenated at rt and 50 psi of H₂ for 4 h. The mixture was filtered and the mixture was concentrated in vacuo. The crude product was purified by chromatography to obtain 1.24 g of the product.

MS (ESI⁺): (M+H)⁺ 197
HPLC: RT=0.15 min, Method F

Intermediate 4.1

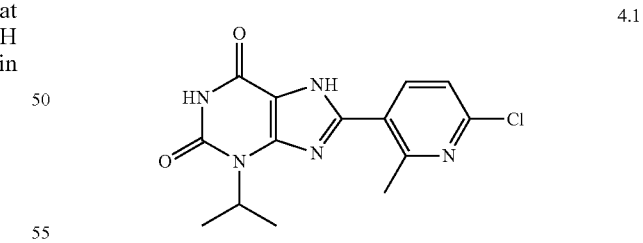

4.1

To a mixture of intermediate 3.1 (0.4 g, 1.8 mmol) in DMF (1.00 mL) and DMSO (1.00 mL) 6-chloro-2-methylpyridine-3-carbaldehyde (282 mg, 1.8 mmol) was added and the mixture was stirred 45 min at 100° C. in the microwave. The mixture was cooled to rt, H₂O was added and the obtained precipitate was filtered and dried to obtain 0.41 g of the product.

MS (ESI⁺): (M+H)⁺ 319
HPLC: RT=0.70 min, Method F

Intermediate 4.2

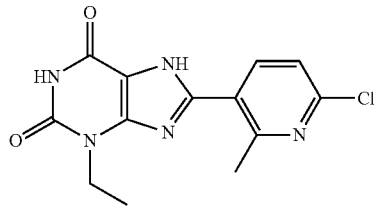

Intermediate 4.2 was prepared in an analogous manner to intermediate 4.1 using intermediate 3.2 and 6-chloro-2-methylpyridine-3-carbaldehyde.
MS (ESI+): (M+H)+ 306
HPLC: RT=0.54 min, Method C Intermediate 4.3

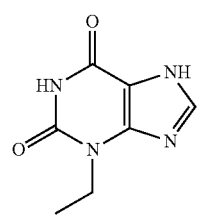

To a mixture of intermediate 3.3 (2.0 g, 10.6 mmol) in (diethoxymethoxy) ethane (16.5 mL) formic acid (0.535 mL, 12.2 mmol) was added and the mixture was stirred overnight at 150° C. The mixture was cooled in an icebath, the obtained precipitate was filtered, washed with tert-butylmethylether and dried to obtain 1.93 g of the product.
MS (ESI+): (M+H)+ 181
HPLC: RT=0.27 min, Method F Intermediate 4.4

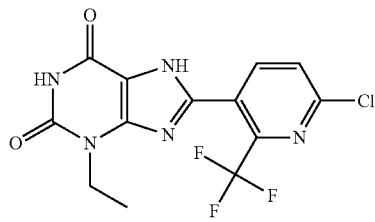

To a mixture of intermediate 3.2 (0.8 g, 3.1 mmol) in DMF (4.00 mL, 49.2 mmol) and DMSO (4.00 mL, 56.3 mmol) 6-chloro-2-(trifluoromethyl)pyridine-3-carbaldehyde (649 mg, 3.1 mmol) was added and the mixture was stirred 45 min at 100° C. in the microwave. H2O was added, the obtained precipitate was filtered and dried to obtain 1.10 g of the product.
MS (ESI+): (M+H)+ 360
HPLC: RT=0.68 min, Method F Intermediate 4.6

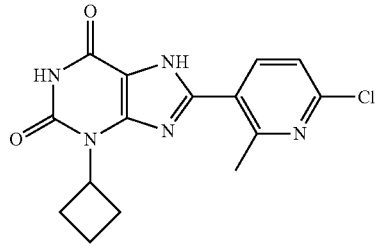

To a mixture of intermediate 3.4 (300 mg, 1.03 mmol) in DMF (1 mL, 12.3 mmol) and DMSO (1 mL, 14.1 mmol) 6-chloro-2-methylpyridine-3-carbaldehyde (160.5 mg, 1.03 mmol) was added and the mixture was stirred 45 min at 100° C. in the microwave. H2O was added, the obtained precipitate was filtered and dried to obtain 0.31 g of the product.
MS (ESI+): (M+H)+ 332/334
HPLC: RT=0.75 min, Method F Intermediate 4.8

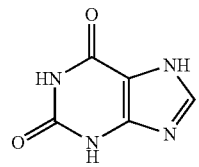

To a mixture of 5,6-diamino-1,2,3,4-tetrahydropyrimidine-2,4-dione-sulfate (8.45 g, 35.2 mmol) in (diethoxymethoxy) ethane (52.7 mL, 317 mmol) formic acid (3.08 mL, 70.4 mmol) was added and the mixture was stirred overnight at 150° C. The mixture was cooled, H2O was added and the obtained precipitate was filtered, washed with H2O and dried to obtain 5.83 g of the product.
MS (ESI+): (M+H)+ 153.1
HPLC: RT=0.10 min, Method D Intermediate 4.10

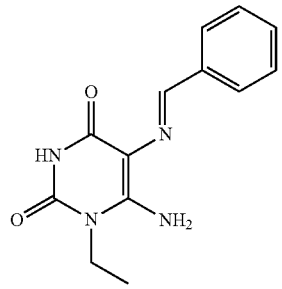

To a mixture of intermediate 3.2 (2.0 g, 8.23 mmol) in H2O (104 ml) benzaldehyde (1.67 mL, 16.46 mmol) was added and the mixture was stirred 1 h at rt. The obtained precipitate was filtered, washed with water and dried to obtain 2.27 g of the product.
MS (ESI⁺): (M+H)⁺ 259/260
HPLC: RT=0.41 min, Method D Intermediate 4.11

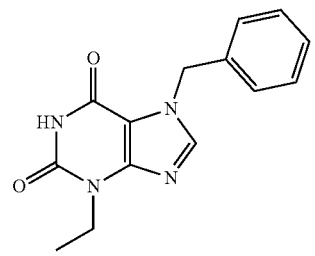

4.11

To a mixture of intermediate 23.1 (594 mg, 1.62 mmol) in (diethoxymethoxy)ethane (17.47 mL, 105 mmol) formic acid (170.6 µL, 4.52 mmol) was added and the mixture was stirred 30 min at reflux. The mixture was cooled, H₂O was added and the obtained precipitate was filtered and dried to obtain 241 mg of the product.
MS (ESI⁺): (M+H)+ 271/272
HPLC: RT=0.39 min, Method D Intermediate 4.12

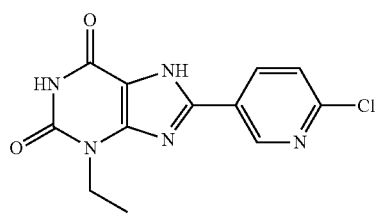

4.12

To a mixture of intermediate 3.2 (1.0 g, 4.84 mmol) in DMF (10 mL, 123 mmol) and DMSO (10 mL, 141 mmol) 6-chloropyridine-3-carbaldehyde (685 mg, 4.84 mmol) was added and the mixture was stirred 45 min at 100° C. in the microwave. H₂O was added, the obtained precipitate was filtered, washed with H₂O and dried to obtain 1.0 g of the product.
MS (ESI⁺): (M+H)⁺ 292/294
HPLC: RT=0.57 min, Method C Intermediate 4.13

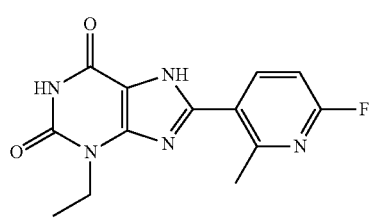

4.13

Intermediate 4.13 was prepared in an analogous manner to intermediate 4.12 using intermediate 3.2 and 6-fluoro-2-methylpyridine-3-carbaldehyde.
MS (ESI⁺): (M+H)⁺ 290/291
HPLC: RT=0.52 min, Method F Intermediate 5.1

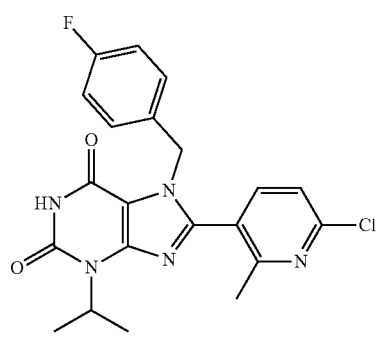

5.1

To a mixture of intermediate 4.1 (405 mg, 1.27 mmol) in DMF (3.00 mL), THF (3 mL) and DMSO (3 mL) DIPEA (0.262 mL, 1.52 mmol) and 1-(bromomethyl)-4-fluorobenzene (0.157 mL, 1.27 mmol) were added and the mixture was stirred 2.5 h at 80° C. The mixture was acidified with TFA and purified by chromatography to obtain 508 mg of the product.
MS (ESI⁺): (M+H)⁺ 427
HPLC: RT=0.88 min, Method F Intermediate 5.2

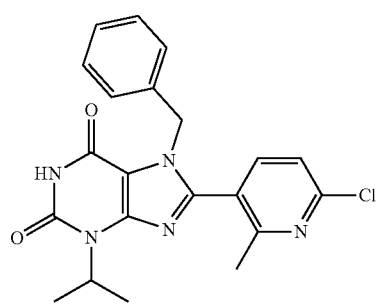

5.2

To a mixture of intermediate 4.1 (1.5 g, 4.47 mmol) in DMF (15.0 mL), DIPEA (0.923 mL, 5.37 mmol) and (bromomethyl)benzene (0.53 mL, 4.47 mmol) were added and the mixture was stirred 1 h at 80° C. H₂O was added and extracted with EtOAc. The combined organic layers were dried and concentrated in vacuo to obtain 1.54 g of the product.
MS (ESI⁺): (M+H)+ 411/413
HPLC: RT=0.9 min, Method F

Intermediate 5.3

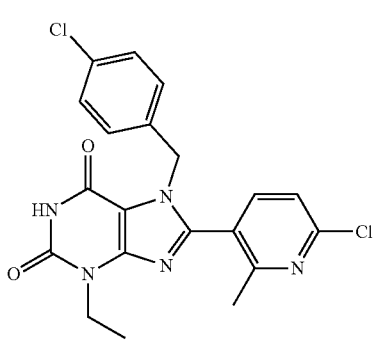

Intermediate 5.3 was prepared in an analogous manner to intermediate 5.1 using intermediate 4.2 and 1-(bromomethyl)-4-chlorobenzene.

MS (ESI$^+$): (M+H)$^+$ 430

HPLC: RT=0.85 min, Method F

Intermediate 5.4

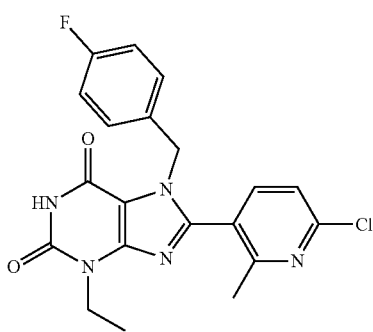

To a mixture of intermediate 4.2 (1.0 g, 3.27 mmol) in DMF (10.0 mL), DIPEA (0.675 mL, 3.93 mmol) and 1-(bromomethyl)-4-fluorobenzene (0.404 mL, 3.27 mmol) were added and the mixture was stirred 4 h at 80° C. The mixture was cooled, filtered and the filtrate was purified by chromatography to obtain 0.67 g of the product.

MS (ESI$^+$): (M+H)+ 414/416

HPLC: RT=0.79 min, Method F

Intermediate 5.5

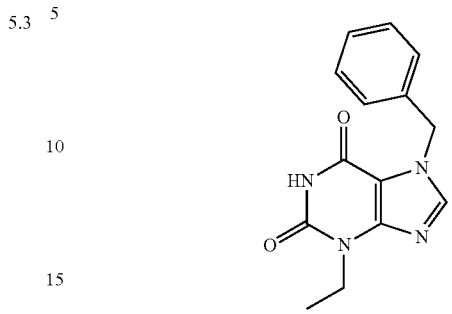

To a mixture of intermediate 4.3 (150 mg, 0.83 mmol) in THF (0.53 mL) and DMSO (0.53 mL) DIPEA (0.29 mL, 1.67 mmol) was added an the mixture was stirred 5 min at 80° C. Then (bromomethyl)benzene (0.99 mL, 0.83 mmol) was added and the mixture was stirred 1 h at 80° C. H$_2$O was added and extracted with EtOAc. The combined organic layers were dried, concentrated in vacuo and purified by chromatography to obtain 85.0 mg of the product.

MS (ESI$^+$): (M+H)+ 271/272

HPLC: RT=0.4 min, Method G

Intermediate 5.6

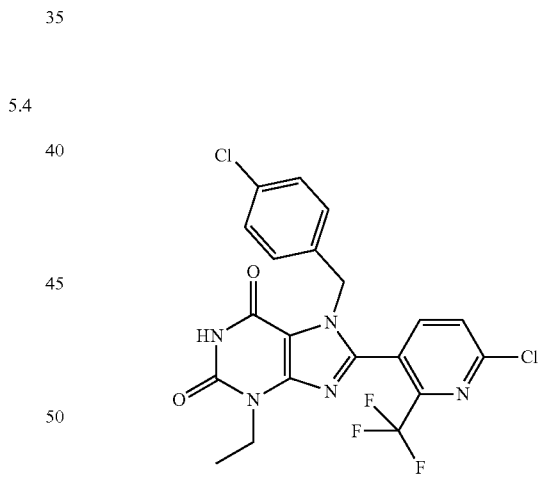

To a mixture of intermediate 4.4 (0.2 g, 0.56 mmol) in DMF (4.0 mL), DIPEA (0.115 mL, 0.67 mmol) and 1-(bromomethyl)-4-chlorobenzene (114 mg, 0.56 mmol) were added and the mixture was stirred 2.5 h at 80° C. The reaction mixture was filtered and purified by chromatography to obtain 226 mg of the product.

MS (ESI$^+$): (M+H)$^+$ 484

HPLC: RT=0.95 min, Method F

Intermediate 5.7

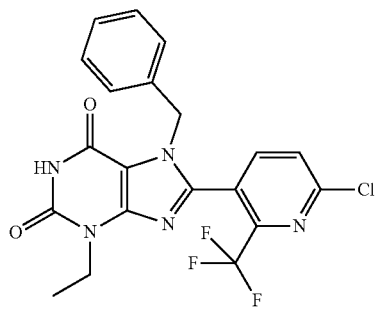

Intermediate 5.7 was prepared in an analogous manner to intermediate 5.6 using intermediate 4.4 and (bromomethyl)benzene.
MS (ESI⁺): (M+H)⁺ 450
HPLC: RT=0.87 min, Method F Intermediate 5.9

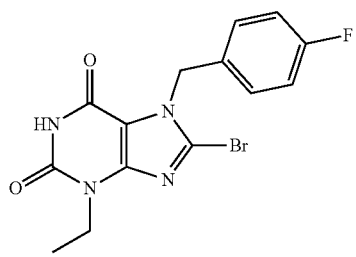

To a mixture of intermediate 13.1 (90 mg, 0.347 mmol) in DMF (1.0 mL), DIPEA (0.119 mL, 0.695 mmol) and 1-(bromomethyl)-4-fluorobenzene (0.043 mL, 0.347 mmol) were added and the mixture was stirred 1 h at rt. H₂O was added, the obtained precipitate was filtered and dried to obtain 104 mg of the product.
MS (ESI⁺): (M+H)⁺ 367/369
HPLC: RT=0.74 min, Method F Intermediate 5.10

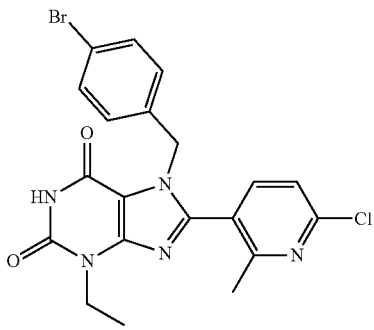

Intermediate 5.10 was prepared in an analogous manner to intermediate 5.6 using intermediate 4.2 and 1-bromo-4-(bromomethyl)benzene.
MS (ESI⁺): (M+H)⁺ 476
HPLC: RT=0.88 min, Method F Intermediate 5.11

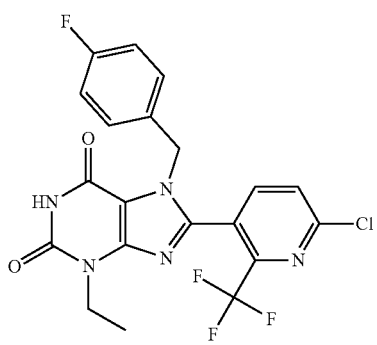

Intermediate 5.11 was prepared in an analogous manner to intermediate 5.6 using intermediate 4.4 and 1-(bromomethyl)-4-fluorobenzene.
MS (ESI⁺): (M+H)⁺ 468
HPLC: RT=0.90 min, Method F Intermediate 5.12

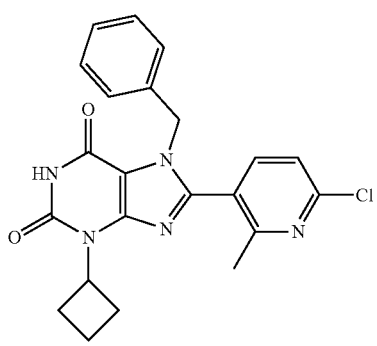

To a mixture of intermediate 4.6 (308 mg, 0.93 mmol) in DMF (5.0 mL), DIPEA (0.192 mL, 1.11 mmol) and (bromomethyl)benzene (110.3 µL, 0.93 mmol) were added and the mixture was stirred 2 h at 80° C. The reaction mixture was purified by chromatography to obtain 282 mg of the product.
MS (ESI⁺): (M+H)⁺ 422/424
HPLC: RT=0.96 min, Method F Intermediate 5.14

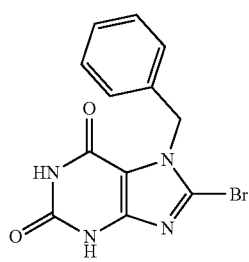
5.14

To a mixture of intermediate 13.2 (6.1 g, 13.2 mmol) in DMF (35 mL), THF (35 mL) and DMSO (35 mL) DIPEA (6.8 mL, 39.6 mmol) and (bromomethyl)benzene (1.67 mL, 14.5 mmol) were added and the mixture was stirred 45 min at rt. The mixture was filtered, concentrated in vacuo and purified by chromatography to obtain 1.70 g of the product.

MS (ESI$^+$): (M+H)$^+$ 321

HPLC: RT=0.56 min, Method F

Intermediate 5.15

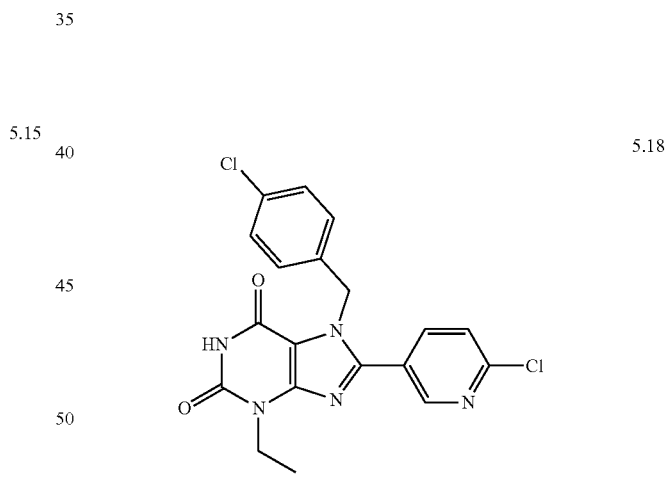
5.15

To a mixture of intermediate 4.2 (1.0 g, 3.27 mmol) in DMF (10.0 mL), DIPEA (0.675 mL, 3.93 mmol) and (bromomethyl)benzene (388.5 µL, 3.27 mmol) were added and the mixture was stirred 4 h at 80° C. The reaction mixture was cooled, filtered and purified by chromatography to obtain 684 mg of the product.

MS (ESI$^+$): (M+H)$^+$ 396/398

HPLC: RT=0.78 min, Method F

Intermediate 5.17

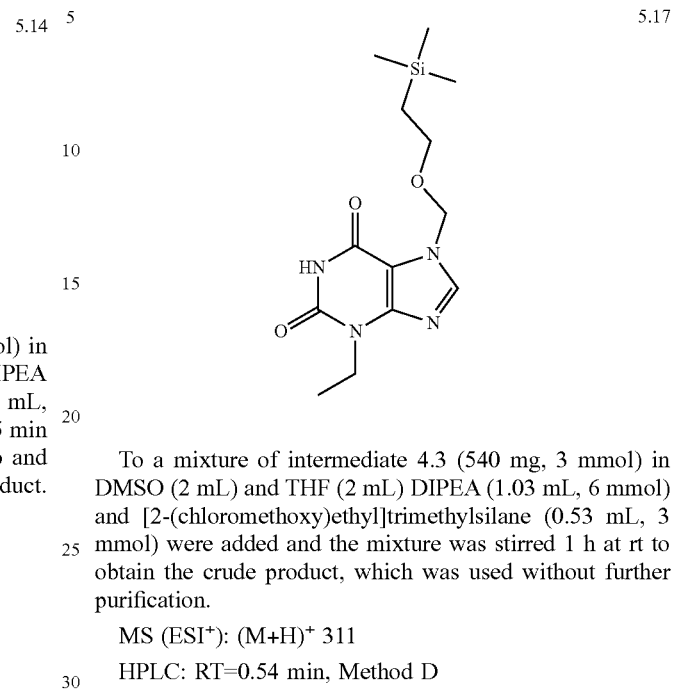
5.17

To a mixture of intermediate 4.3 (540 mg, 3 mmol) in DMSO (2 mL) and THF (2 mL) DIPEA (1.03 mL, 6 mmol) and [2-(chloromethoxy)ethyl]trimethylsilane (0.53 mL, 3 mmol) were added and the mixture was stirred 1 h at rt to obtain the crude product, which was used without further purification.

MS (ESI$^+$): (M+H)$^+$ 311

HPLC: RT=0.54 min, Method D

Intermediate 5.18

5.18

To a mixture of intermediate 4.12 (350 mg, 1.2 mmol) in DMF (3 mL, 37 mmol) DIPEA (247.7 µL, 1.44 mmol) and 1-(bromomethyl)-4-chlorobenzene (246.6 mg, 1.2 mmol) were added and the mixture was stirred overnight at 80° C. The reaction mixture was filtered and purified by chromatography to obtain 148 mg of the product.

MS (ESI$^+$): (M+H)+ 416/418

HPLC: RT=0.85 min, Method F

Intermediate 5.19

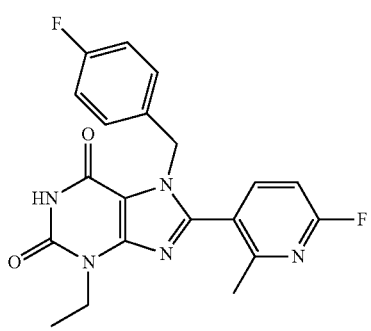

Intermediate 5.19

To a mixture of intermediate 4.13 (426 mg, 1.47 mmol) in DMF (5 mL, 61.5 mmol) DIPEA (304 µL, 1.77 mmol) and 1-(bromomethyl)-4-fluorobenzene (193 µL, 1.47 mmol) were added and the mixture was stirred 1 h at 80° C. The reaction mixture was filtered, H$_2$O was added and extracted with EtOAc. The combined organic layers were dried and concentrated in vacuo. The crude product was purified by chromatography to obtain 344 mg of the product.

MS (ESI$^+$): (M+H)$^+$ 398/400

HPLC: RT=0.73 min, Method F

Intermediate 5.20

Intermediate 5.21

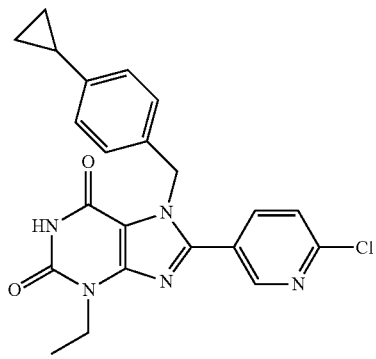

Intermediate 4.12 (300 mg, 1.03 mmol) was dissolved in DMF (1 mL), THF (1 mL) and DMSO (1 mL). DIPEA (581 µL, 3.4 mmol) was added and the mixture was stirred 5 min at 80° C. Then intermediate 24.1 (217 mg, 1.03 mmol) was added and the mixture was stirred 1.5 h at 80° C. The reaction mixture was acidified with TFA, filtered, purified by chromatography and freeze dried to obtain 61.1 mg of the product.

MS (ESI$^+$): (M+H)$^+$ 422

HPLC: RT=0.91 min, Method F

Intermediate 5.23

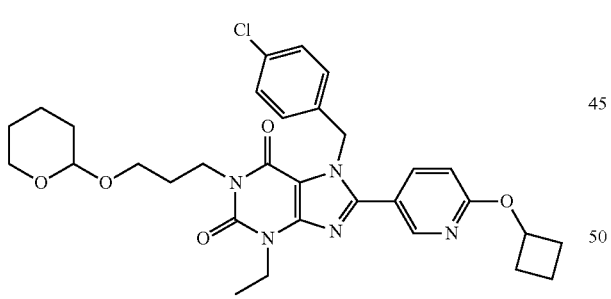

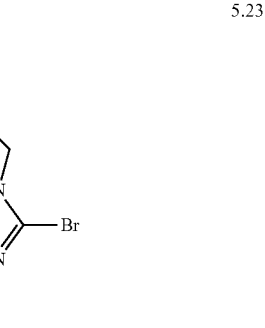

To a mixture of intermediate 22.1 (23.5 mg, 0.05 mmol) in THF (413 µL, 5.2 mmol) and DMSO (413 µL, 5.8 mmol) DIPEA (9.5 µL, 0.06 mmol) and 1-(bromomethyl)-4-chlorobenzene (15.4 mg, 0.075 mmol) were added and the mixture was stirred at 50° C. The mixture was cooled and used without further purification.

MS (ESI$^+$): (M+H)$^+$ 594

HPLC: RT=0.9 min, Method D

To a mixture of intermediate 13.1 (611 mg, 2.36 mmol) in DMF (5.75 mL) DIPEA (1.22 mL, 7.08 mmol) and 1-(bromomethyl)-4-chlorobenzene (484.6 mg, 2.36 mmol) were added and the mixture was stirred 1 h at rt. The mixture was purified by chromatography to obtain 850 mg of the product.

MS (ESI$^+$): (M+H)$^+$ 385

HPLC: RT=0.57 min, Method G

Intermediate 5.24

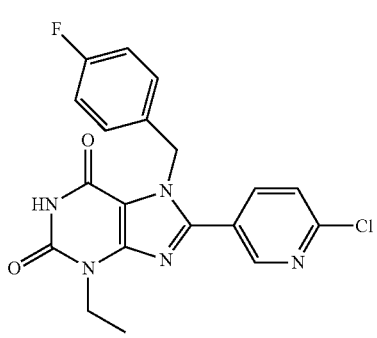

To a mixture of intermediate 4.12 (150 mg, 0.514 mmol) in DMF (3 mL) DIPEA (106 µL, 0.617 mmol) and 1-(bromomethyl)-4-fluorobenzene (63.5 µL, 0.514 mmol) were added and the mixture was stirred overnight at 80° C. The mixture was cooled, filtered and purified by chromatography to obtain 54.0 mg of the product.

MS (ESI$^+$): (M+H)$^+$ 400/402

HPLC: RT=0.79 min, Method F

Intermediate 5.25

Intermediate 5.26

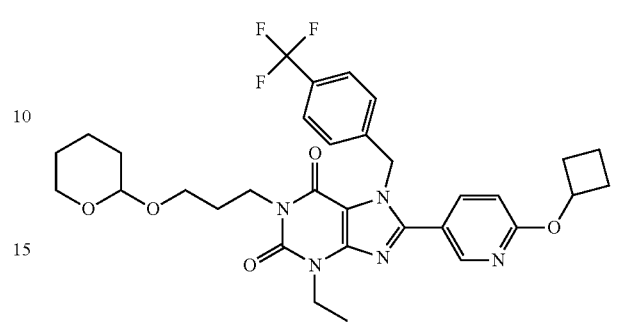

To a mixture of intermediate 22.1 (42.3 mg, 0.09 mmol) in THF (744 µL, 9.27 mmol) and DMSO (740 µL, 10.4 mmol) DIPEA (17 µL, 0.10 mmol) and 1-(bromomethyl)-4-(trifluoromethyl)benzene (20.9 µL, 0.135 mmol) were added and the mixture was stirred overnight at 50° C. The mixture was cooled and used without further purification.

MS (ESI$^+$): (M+H)$^+$ 628

HPLC: RT=0.92 min, Method D

Intermediate 5.27

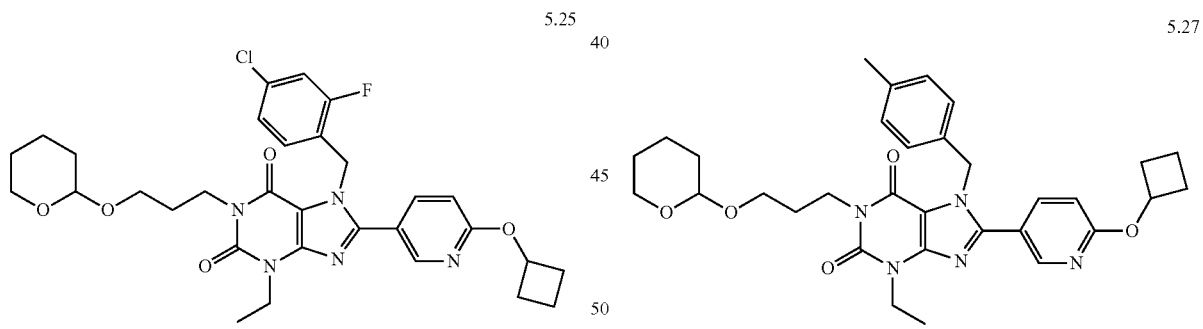

To a mixture of intermediate 22.1 (42.3 mg, 0.09 mmol) in THF (744 µL, 9.27 mmol) and DMSO (740 µL, 10.4 mmol) DIPEA (17 µL, 0.10 mmol) and 1-(bromomethyl)-4-chloro-2-fluorobenzene (18.3 µL, 0.135 mmol) were added and the mixture was stirred overnight at 50° C. The mixture was cooled and used without further purification.

MS (ESI$^+$): (M+H)$^+$ 614

HPLC: RT=0.92 min, Method D

To a mixture of intermediate 22.1 (42.3 mg, 0.09 mmol) in THF (744 µL, 9.27 mmol) and DMSO (740 µL, 10.4 mmol) DIPEA (17 µL, 0.10 mmol) and 1-(bromomethyl)-4-methylbenzene (25 mg, 0.135 mmol) were added and the mixture was stirred overnight at 50° C. The mixture was cooled and used without further purification.

MS (ESI$^+$): (M+H)$^+$ 574

HPLC: RT=0.91 min, Method D

Intermediate 5.28

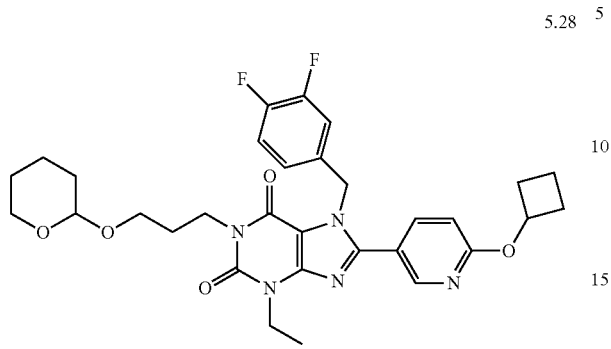

To a mixture of intermediate 22.1 (42.3 mg, 0.09 mmol) in THF (744 µL, 9.27 mmol) and DMSO (740 µL, 10.4 mmol) DIPEA (17 µL, 0.10 mmol) and 4-(bromomethyl)-1,2-difluorobenzene (28 mg, 0.135 mmol) were added and the mixture was stirred overnight at 50° C. The mixture was cooled and used without further purification.

MS (ESI$^+$): (M+H)$^+$ 596

HPLC: RT=0.88 min, Method D

Intermediate 5.29

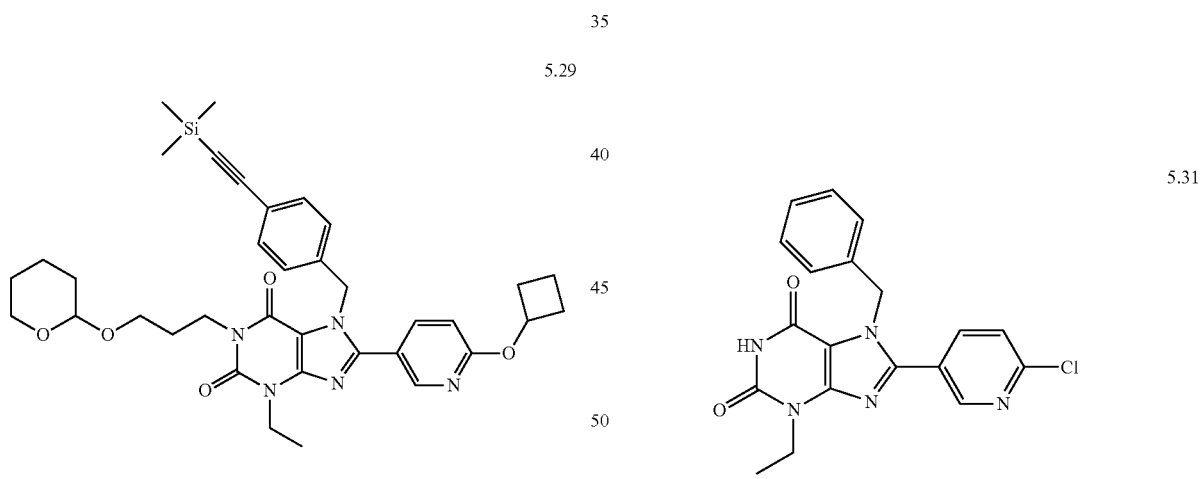

To a mixture of intermediate 22.1 (74 mg, 0.102 mmol) in THF (1 mL, 12.5 mmol) and DMSO (1 mL, 14.1 mmol) DIPEA (81 µL, 0.47 mmol) and intermediate 24.2 (63 mg, 0.24 mmol) were added and the mixture was stirred 45 min at 50° C. and overnight at 90° C. Additional DIPEA and intermediate 24.2 and ACN (2 mL) were added and the mixture was stirred 4 h at 90° C. The mixture was cooled, filtered and purified by chromatography to obtain 13.0 mg of the product.

MS (ESI$^+$): (M+H)$^+$ 656

HPLC: RT=0.97 min, Method A

Intermediate 5.30

To a mixture of intermediate 4.3 (400 mg, 2.22 mmol) in THF (1.42 mL) and DMSO (1.42 mL) DIPEA (274 µL, 4.44 mmol) and after 5 min at 80° C. 1-(bromomethyl)-4-fluorobenzene (274 µL, 2.22 mmol) were added and the mixture was stirred 1 h at 80° C. H$_2$O was added and extracted with EtOAc. The combined organic layers were dried, concentrated in vacuo and purified by chromatography to obtain 268 mg of the product.

MS (ESI$^+$): (M+H)$^+$ 289

HPLC: RT=0.59 min, Method F

Intermediate 5.31

To a mixture of intermediate 4.12 (150 mg, 0.514 mmol) in DMF (3 mL, 37 mmol) DIPEA (106 µL, 0.617 mmol) and (bromomethyl)benzene (61 µL, 0.514 mmol) were added and the mixture was stirred overnight at 80° C. The mixture was cooled, filtered and purified by chromatography to obtain 57.0 mg of the product.

MS (ESI$^+$): (M+H)$^+$ 382/384

HPLC: RT=0.78 min, Method F

Intermediate 6.1

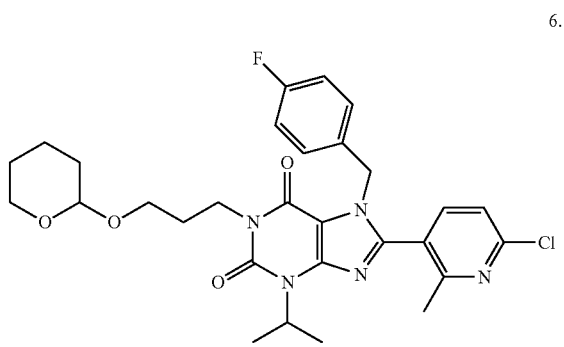

To a mixture of intermediate 5.1 (0.51 g, 1.19 mmol) in anhydrous DMF (2 mL) $K_2CO_3$ (0.328 g, 2.38 mmol) and 2-(3-bromopropoxy)tetrahydro-2H-pyrane (0.302 mL, 1.78 mmol) were added and the mixture was stirred for 1 h at 80° C. $H_2O$ was added and extracted with EtOAc. The combined organic layers were dried, concentrated in vacuo and the crude product purified by chromatography to obtain 556 mg of the product.

MS (ESI$^+$): (M+H)$^+$ 570
HPLC: RT=0.83 min, Method D

Intermediate 6.3

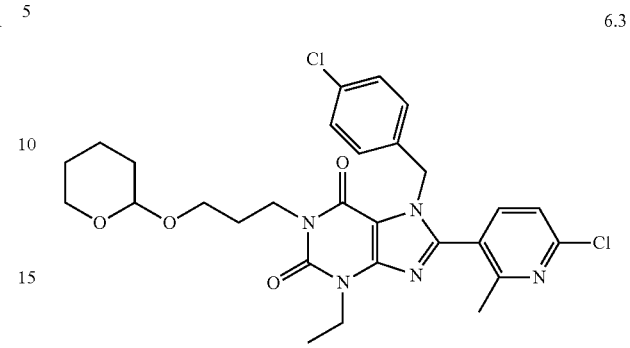

To a mixture of intermediate 5.3 (0.39 g, 0.91 mmol) in anhydrous DMF (2 mL) $K_2CO_3$ (0.252 g, 1.82 mmol) and 2-(3-bromopropoxy)tetrahydro-2H-pyrane (0.232 mL, 1.37 mmol) were added and the mixture was stirred for 2 h at 50° C. $H_2O$ was added and extracted with EtOAc. The combined organic layers were dried, concentrated in vacuo and the crude product purified by chromatography to obtain 438 mg of the product.

MS (ESI$^+$): (M+H)$^+$ 572
HPLC: RT=1.38 min, Method C

Intermediate 6.2

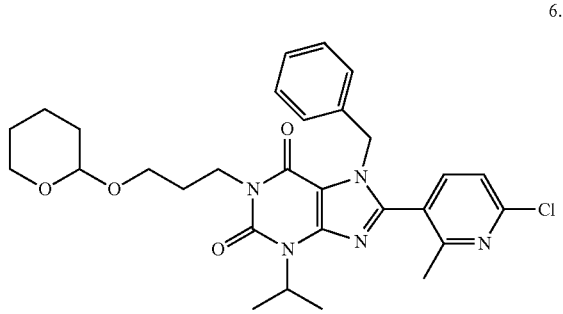

Intermediate 6.2 was prepared in an analogous manner to intermediate 6.1 using intermediate 5.2.

MS (ESI$^+$): (M+H)$^+$ 553/554
HPLC: RT=0.82 min, Method G

Intermediate 6.4

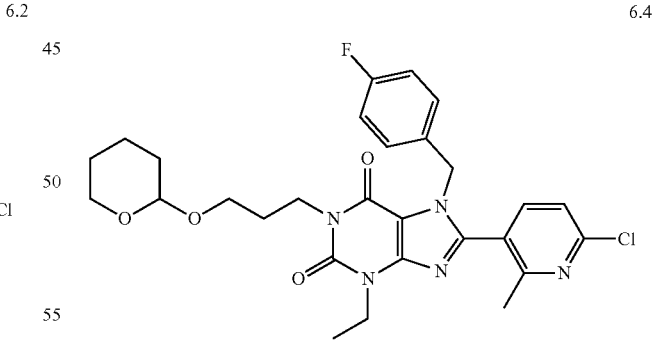

Intermediate 6.4 was prepared in an analogous manner to intermediate 6.1 using intermediate 5.4.

MS (ESI$^+$): (M+H)$^+$ 556/558
HPLC: RT=0.77 min, Method D

Intermediate 6.5

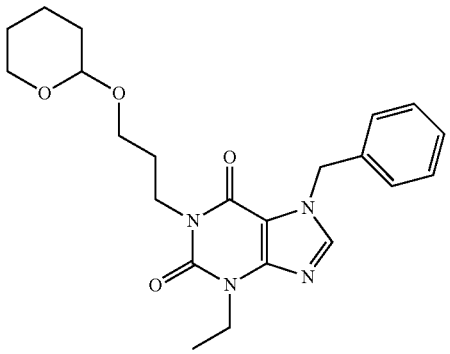

Intermediate 6.5 was prepared in an analogous manner to intermediate 6.1 using intermediate 5.5.
MS (ESI+): (M+H)+ 413/414
HPLC: RT=0.63 min, Method G Intermediate 6.6

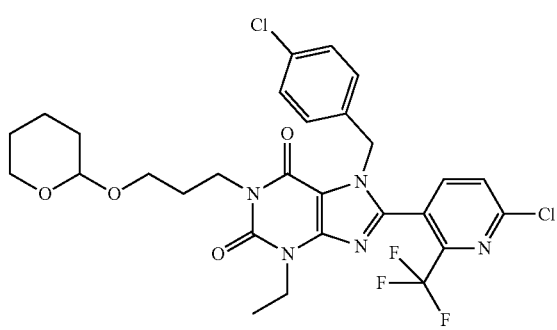

Intermediate 6.6 was prepared in an analogous manner to intermediate 6.3 using intermediate 5.6.
MS (ESI+): (M+H)+ 626
HPLC: RT=1.45 min, Method C Intermediate 6.7

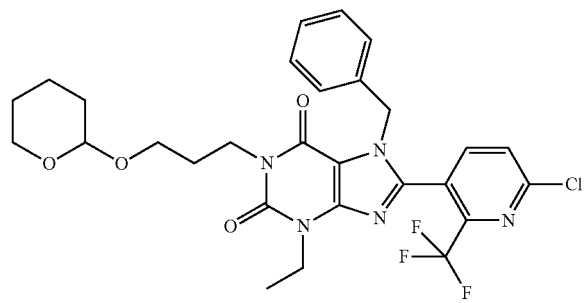

Intermediate 6.7 was prepared in an analogous manner to intermediate 6.3 using intermediate 5.7.
MS (ESI+): (M+H)+ 592
HPLC: RT=1.38 min, Method C Intermediate 6.9

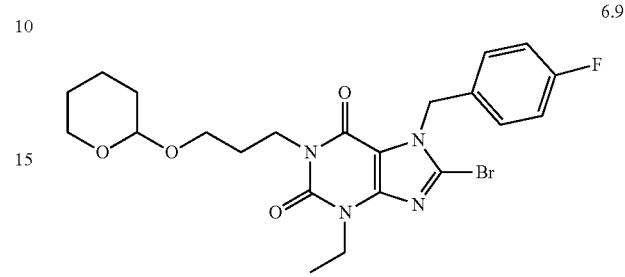

Intermediate 6.9 was prepared in an analogous manner to intermediate 6.3 using intermediate 5.9.
MS (ESI+): (M+H)+ 510/511
HPLC: RT=0.73 min, Method G Intermediate 6.10

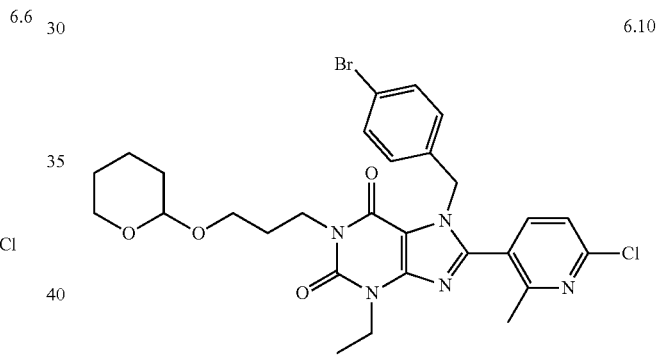

Intermediate 6.10 was prepared in an analogous manner to intermediate 6.3 using intermediate 5.10.
MS (ESI+): (M+H)+ 618
HPLC: RT=0.83 min, Method D Intermediate 6.11

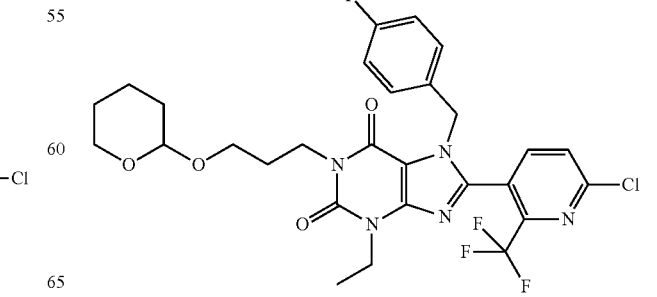

To a mixture of intermediate 5.11 (192 mg, 0.41 mmol) in anhydrous DMF (2 mL) K₂CO₃ (114 mg, 0.82 mmol) and 2-(3-bromopropoxy)tetrahydro-2H-pyrane (0.105 mL, 0.62 mmol) were added and the mixture was stirred for 2 h at 50° C. H₂O was added and extracted with EtOAc. The combined organic layers were dried, concentrated in vacuo and purified by chromatography to obtain 207 mg of the product.

MS (ESI⁺): (M+H)⁺ 610
HPLC: RT=1.40 min, Method C

Intermediate 6.12

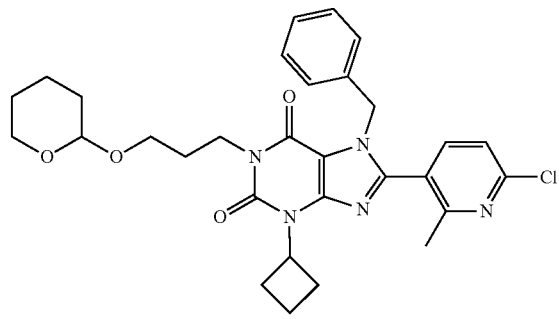

6.12

To a mixture of intermediate 5.12 (282 mg, 0.67 mmol) in anhydrous DMF (3 mL) K₂CO₃ (277.2 mg, 2.01 mmol) and 2-(3-bromopropoxy)tetrahydro-2H-pyrane (170.4 µL, 1.00 mmol) were added and the mixture was stirred for 2 h at 80° C. H₂O was added and extracted with EtOAc. The combined organic layers were dried, concentrated in vacuo and purified by chromatography to obtain 321 mg of the product.

MS (ESI⁺): (M+H)⁺ 564/566
HPLC: RT=0.84 min, Method F

Intermediate 6.14

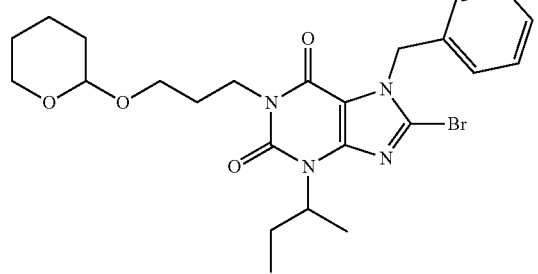

6.14

To a mixture of intermediate 19.1 (700 mg, 1.86 mmol) in THF (7.73 mL), DMSO (7.78 mL) and DMF (7.84 mL) K₂CO₃ (769 mg, 0.006 mol) and 2-(3-bromopropoxy)tetrahydro-2H-pyrane (0.42 mL, 2.78 mmol) were added and the mixture was stirred for 1 h at 100° C. The mixture was cooled, diluted with ACN and purified by chromatography to obtain 811 mg of the product.

MS (ESI⁺): (M+H-THP)⁺ 437
HPLC: RT=0.84 min, Method G

Intermediate 6.15

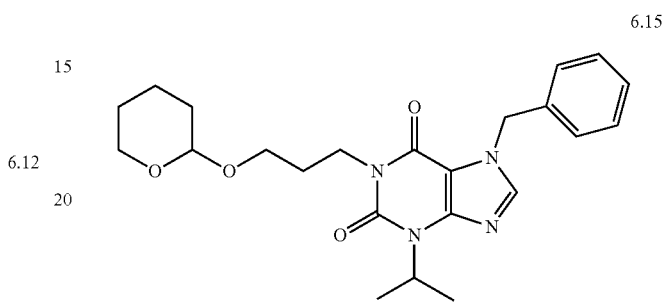

6.15

To a mixture of intermediate 19.2 (660 mg, 2.16 mmol) in anhydrous DMF (5 mL) K₂CO₃ (0.9 g, 6.48 mmol) and 2-(3-bromopropoxy)tetrahydro-2H-pyrane (0.55 mL, 3.24 mmol) were added and the mixture was stirred for 2 h at 80° C. H₂O was added and extracted with EtOAc. The combined organic layers were dried, concentrated in vacuo and the crude product was purified by chromatography and freeze dried to obtain 767 mg of the product.

MS (ESI⁺): (M+H)⁺ 427/428
HPLC: RT=0.97 min, Method F

Intermediate 6.16

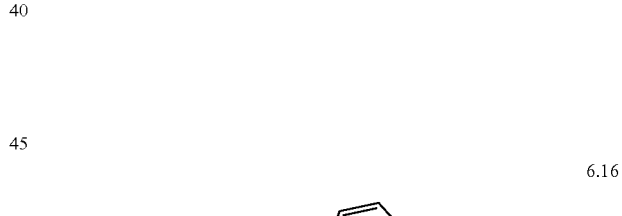

6.16

Intermediate 6.16 was prepared in an analogous manner to intermediate 6.11 using intermediate 5.15.

MS (ESI⁺): (M+H)⁺ 538/540
HPLC: RT=1.06 min, Method F

Intermediate 6.18

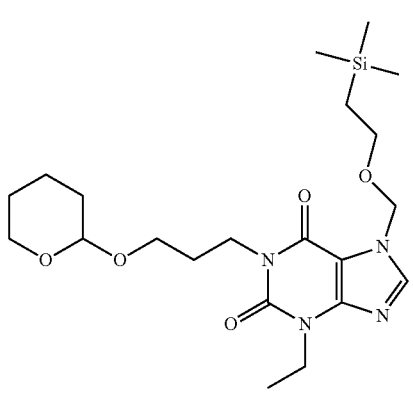

6.18

To the reaction mixture of intermediate 5.17 K$_2$CO$_3$ (1244 mg, 9 mol) and 2-(3-bromopropoxy)tetrahydro-2H-pyrane (764 µL, 4.5 mmol) were added and the mixture was stirred overnight at 90° C. The mixture was cooled and purified by chromatography to obtain 920 mg of the product.

MS (ESI$^+$): (M+H-THP)$^+$ 369

HPLC: RT=0.75 min, Method D

Intermediate 6.19

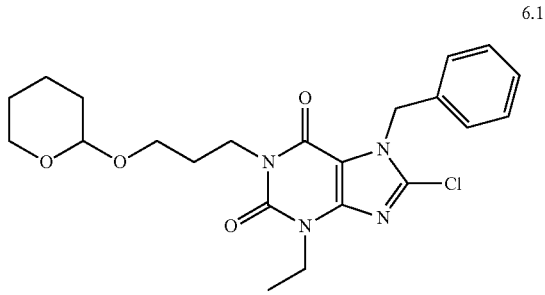

6.19

To a mixture of intermediate 11.5 (0.63 g, 2.08 mmol) in DMF (10 mL) K$_2$CO$_3$ (0.86 g, 6.23 mmol) and 2-(3-bromopropoxy)tetrahydro-2H-pyrane (0.53 mL, 3.12 mmol) were added and the mixture was stirred 2 h at 80° C. H$_2$O was added and extracted with EtOAc. The combined organic layers were dried and concentrated in vacuo. The crude product was purified by chromatography and freeze dried to obtain 414 mg of the product.

MS (ESI$^+$): (M+H)$^+$ 447/449

HPLC: RT=0.73 min, Method G

Intermediate 6.20

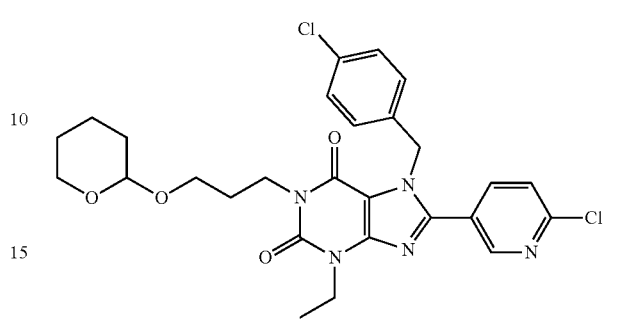

6.20

To a mixture of intermediate 5.18 (148 mg, 0.356 mmol) in anhydrous DMF (1 mL) K$_2$CO$_3$ (98.3 mg, 0.711 mmol) and 2-(3-bromopropoxy)tetrahydro-2H-pyrane (90.4 µL, 0.533 mmol) were added and the mixture was stirred 2 h at 50° C. H$_2$O was added and extracted with EtOAc. The combined organic layers were dried and concentrated in vacuo. The crude product was purified by chromatography and freeze dried to obtain 174 mg of the product.

MS (ESI$^+$): (M+H)$^+$ 558/560

HPLC: RT=1.38 min, Method C

Intermediate 6.21

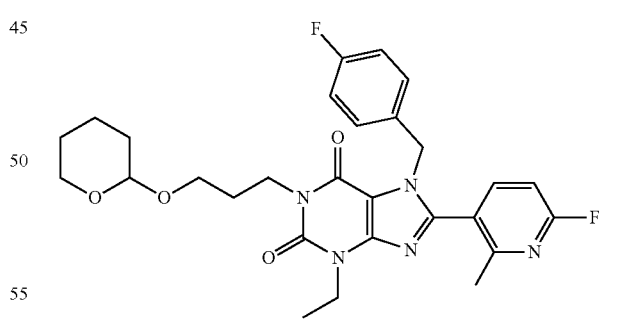

6.21

Intermediate 6.21 was prepared in an analogous manner to intermediate 6.19 using intermediate 5.19.

MS (ESI$^+$): (M+H)$^+$ 540/541

HPLC: RT=0.69 min, Method D

Intermediate 6.22

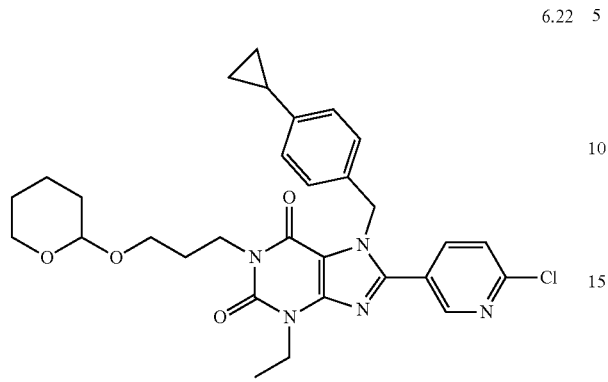

To a mixture of intermediate 5.21 (61 mg, 0.145 mmol) in DMF (2 mL) K₂CO₃ (40 mg, 0.29 mmol) and 2-(3-bromopropoxy)tetrahydro-2H-pyrane (36.8 μL, 0.217 mmol) were added and the mixture was stirred 2 h at 50° C. H₂O was added and extracted with EtOAc. The combined organic layers were dried and concentrated in vacuo. The crude product was purified by chromatography and freeze dried to obtain 66 mg of the product.

MS (ESI$^+$): (M+H)$^+$ 564

HPLC: RT=1.17 min, Method F

Intermediate 6.24

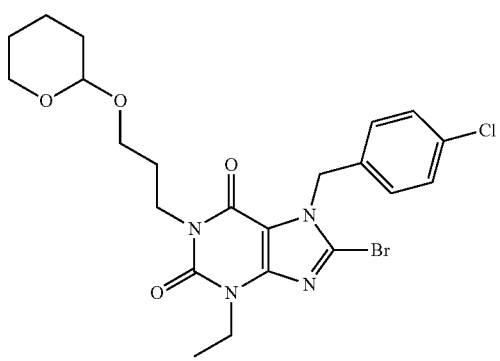

To a mixture of intermediate 5.23 (900 mg, 2.35 mmol) in DMF (3.81 mL) K₂CO₃ (0.97 g, 7.04 mmol) and 2-(3-bromopropoxy)tetrahydro-2H-pyrane (0.60 mL, 3.52 mmol) were added and the mixture was stirred for 1 h at 110° C. The mixture was cooled, filtered, diluted with ACN and purified by chromatography to obtain 1.15 g of the product.

MS (ESI$^+$): (M+H-THP)$^+$ 527

HPLC: RT=0.79 min, Method G

Intermediate 6.25

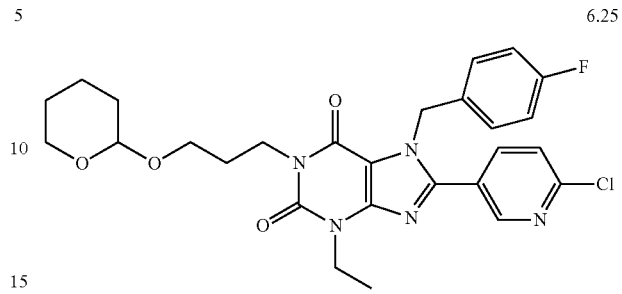

To a mixture of intermediate 5.24 (54 mg, 0.135 mmol) in DMF (1 mL) K₂CO₃ (37 mg, 0.270 mmol) and 2-(3-bromopropoxy)tetrahydro-2H-pyrane (34.3 μL, 0.203 mmol) were added and the mixture was stirred for 2 h at 50° C. H₂O was added and extracted with EtOAc. The combined organic layers were dried and concentrated in vacuo. The crude product was purified by chromatography and freeze dried to obtain 55.0 mg the product.

MS (ESI$^+$): (M+H-THP)$^+$ 542/544

HPLC: RT=1.32 min, Method C

Intermediate 6.26

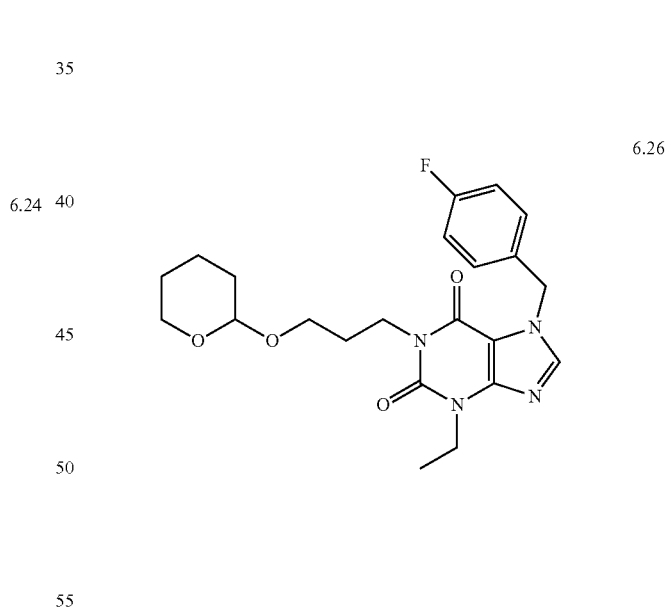

To a mixture of intermediate 5.30 (268 mg, 0.928 mmol) in DMF (3 mL) K₂CO₃ (567 mg, 1.856 mmol) and 2-(3-bromopropoxy)tetrahydro-2H-pyrane (0.24 mL, 1.392 mmol) were added and the mixture was stirred 1 h at 80° C. H₂O was added and extracted with EtOAc. The combined organic layers were dried, concentrated in vacuo and the crude product was purified by chromatography to obtain 345 mg of the product.

MS (ESI$^+$): (M+H)+ 431

HPLC: RT=0.91 min, Method F

Intermediate 6.27

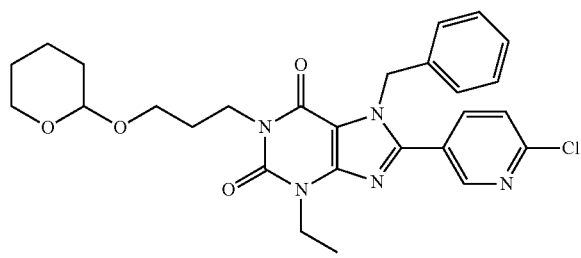

Intermediate 6.27 was prepared in an analogous manner to intermediate 6.25 using intermediate 5.31.
MS (ESI+): (M+H-THP)+ 524/526
HPLC: RT=1.31 min, Method C Intermediate 7.1

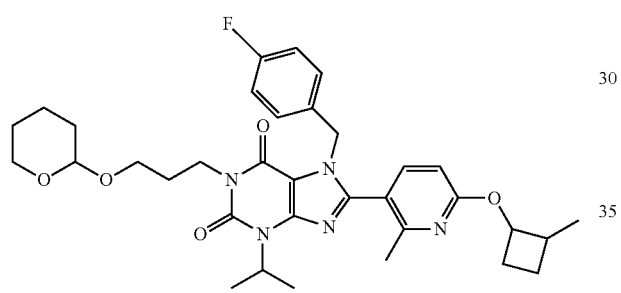

To a mixture of intermediate 6.1 (50 mg, 0.088 mmol) in dioxane (1 mL) 2-methylcyclobutan-1-ol (0.5 mL) and sodium hydride (55%, 7.7 mg, 0.175 mmol) were added. The mixture was stirred for 6 h at 100° C. H$_2$O was added and extracted with EtOAc. The combined organic layers were dried and concentrated in vacuo and the resulting crude product was used without further purification.
HPLC: RT=1.36 min, Method F Intermediate 7.2

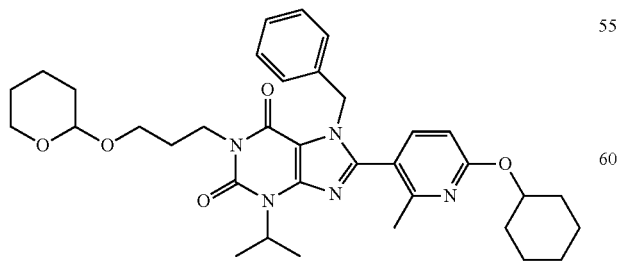

To a mixture of cyclohexanol (26.7 µL, 0.254 mmol) and sodium hydride (11.1 mg, 0.254 mmol) in DMF (0.5 mL) intermediate 6.2 (70 mg, 0.127 mmol) was added and the reaction was stirred 1 h at 50° C. H$_2$O was added and extracted with DCM. The combined organic layers were dried and concentrated in vacuo and the resulting crude product used without further purification.
MS (ESI+): (M+H)+ 616/617
HPLC: RT=0.75 min, Method E Intermediate 7.3

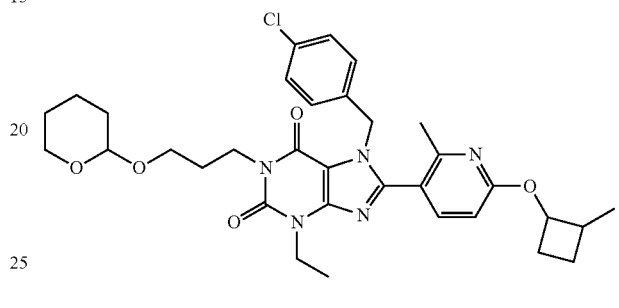

To a mixture of sodium hydride (55%, 7.6 mg, 0.18 mmol) in 2-methylcyclobutan-1-ol (0.5 ml) intermediate 6.3 (50 mg, 0.09 mmol) was added and the mixture was stirred 1.5 h at 100° C. H$_2$O was added and extracted with EtOAc. The combined organic layers were dried and concentrated in vacuo and used without further purification.
MS (ESI+): (M+H)+ 622
HPLC: RT=1.65 min, Method C Intermediate 7.4

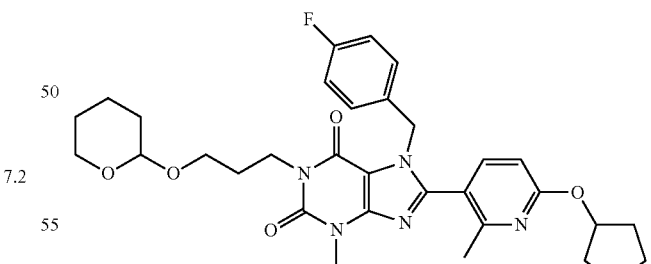

Intermediate 7.4 was prepared in an analogous manner to intermediate 7.1 using intermediate 6.1 and cyclopentanol.
MS (ESI+): (M+H)+ 621
HPLC: RT=1.36 min, Method F Intermediate 7.5

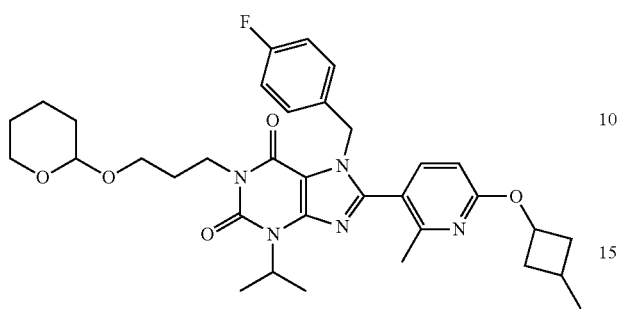

Intermediate 7.5 was prepared in an analogous manner to intermediate 7.1 using intermediate 6.1 and 3-methylcyclobutan-1-ol.
HPLC: RT=1.35 min, Method F Intermediate 7.6

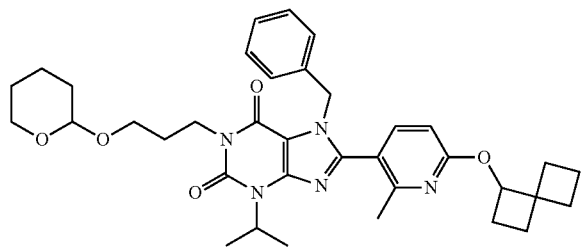

To a mixture of intermediate 6.2 (70 mg, 0.13 mmol) in DMF (0.5 mL) spiro[3.3]heptan-1-ol (28.5 mg, 0.25 mmol) and sodium hydride (55%, 11.1 mg, 0.25 mmol) were added. The mixture was stirred for 1 h at 50° C. H$_2$O was added and extracted with DCM. The combined organic layers were dried and concentrated in vacuo and the crude product was used without further purification.
MS (ESI$^+$): (M+H)$^+$ 628/629
HPLC: RT=0.8 min, Method E Intermediate 7.7

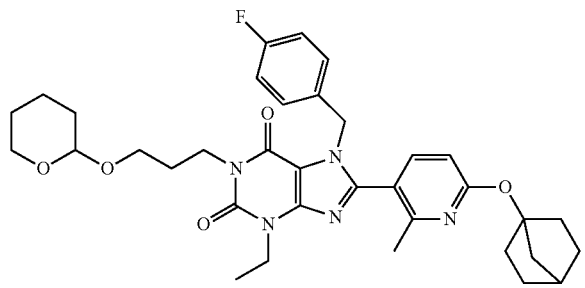

To a mixture of intermediate 6.4 (135 mg, 0.24 mmol) in dioxane (1 mL) bicyclo[2.2.1]heptan-2-ol (0.5 mL, 4.28 mmol) and sodium hydride (55%, 21.2 mg, 0.49 mmol) were added. The mixture was stirred for 3 h at 110° C. H$_2$O was added and extracted with EtOAc. The combined organic layers were dried and concentrated in vacuo. The crude product was purified by chromatography to obtain 117 mg of the product.
MS (ESI$^+$): (M+H)$^+$ 632
HPLC: RT=0.98 min, Method G Intermediate 7.8

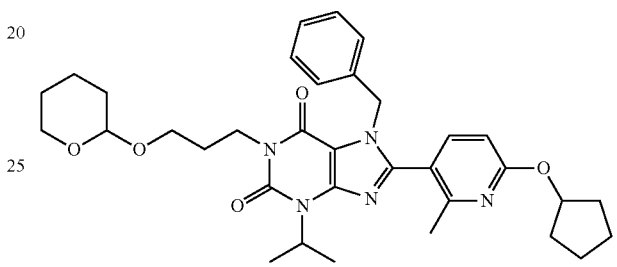

To a mixture of cyclopentanol (1 mL) and sodium hydride (55%, 15.8 mg, 0.36 mmol) in DMF (1 mL) intermediate 6.2 (100 mg, 0.18 mmol) was added and the reaction was stirred 1.5 h at 110° C. H$_2$O was added and extracted with EtOAc. The combined organic layers were dried and concentrated in vacuo and used without further purification.
HPLC: RT=0.98 min, Method D Intermediate 7.9

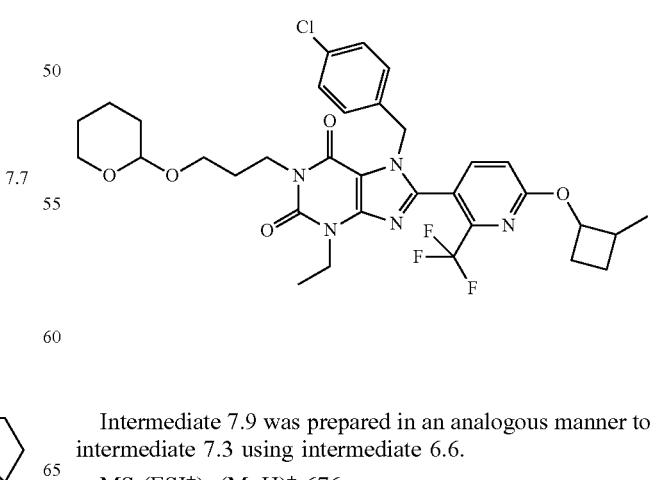

Intermediate 7.9 was prepared in an analogous manner to intermediate 7.3 using intermediate 6.6.
MS (ESI$^+$): (M+H)$^+$ 676
HPLC: RT=1.65 min, Method C Intermediate 7.11

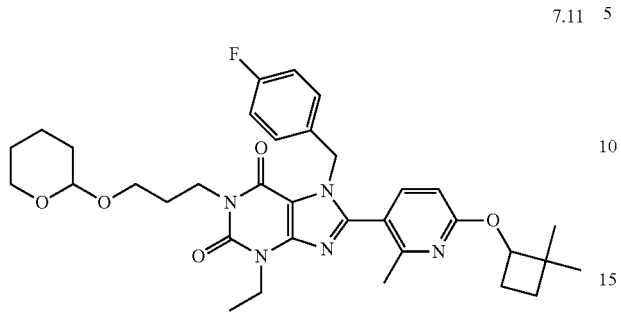

7.11

To a mixture of 2,2-dimethylcyclobutan-1-ol (0.5 mL) and sodium hydride (55%, 11 mg, 0.252 mmol) intermediate 6.4 (70 mg, 0.126 mmol) was added and the reaction was stirred 2 h at rt. H₂O was added and extracted with DCM. The combined organic layers were dried and concentrated in vacuo and the crude product was used without further purification.

MS (ESI⁺): (M+H)+ 620/621

HPLC: RT=0.97 min, Method D

Intermediate 7.12

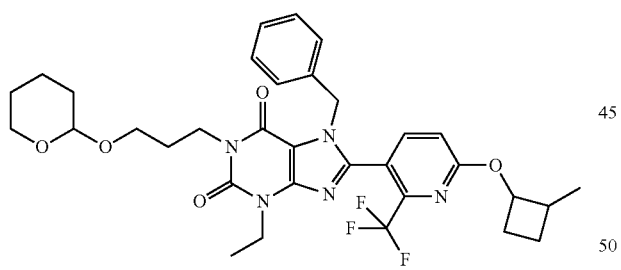

7.12

To a mixture of sodium hydride (55%, 13.3 mg, 0.30 mmol) in 2-methylcyclobutan-1-ol (0.5 ml) intermediate 6.7 (90 mg, 0.15 mmol) was added and the mixture was stirred 1.5 h at 100° C. H₂O was added and extracted with EtOAc. The combined organic layers were dried, concentrated in vacuo and the crude product was purified by chromatography to obtain 33.0 mg the product.

MS (ESI⁺): (M+H)⁺ 642

HPLC: RT=1.62 min, Method C

Intermediate 7.14

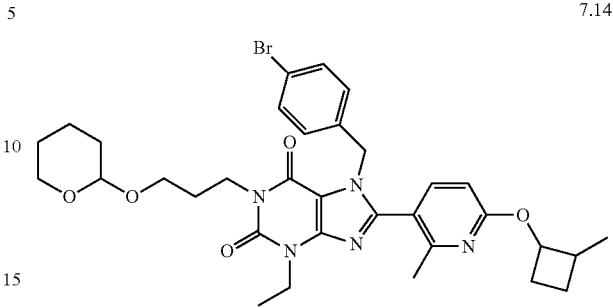

7.14

Intermediate 7.14 was prepared in an analogous manner to intermediate 7.11 using intermediate 6.10.

MS (ESI⁺): (M+H)⁺ 668

HPLC: RT=0.99 min, Method D

Intermediate 7.15

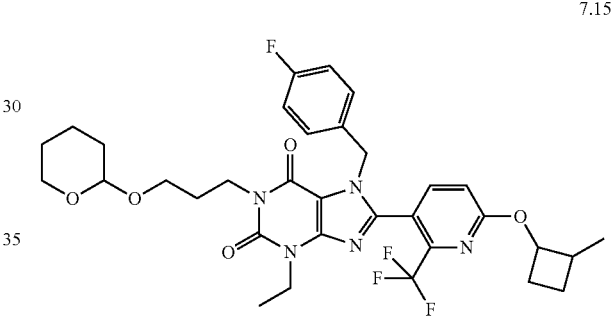

7.15

To a mixture of sodium hydride (55%, 12.9 mg, 0.30 mmol) in 2-methylcyclobutan-1-ol (0.3 ml) intermediate 6.11 (90 mg, 0.15 mmol) was added and the mixture was stirred 2 h at 100° C. H2O was added and extracted with EtOAc. The combined organic layers were dried, concentrated in vacuo and the resulting crude product was purified by chromatography to obtain 69.7 mg of the product.

MS (ESI⁺): (M+H)⁺ 660

HPLC: RT=1.61 min, Method C

Intermediate 7.17

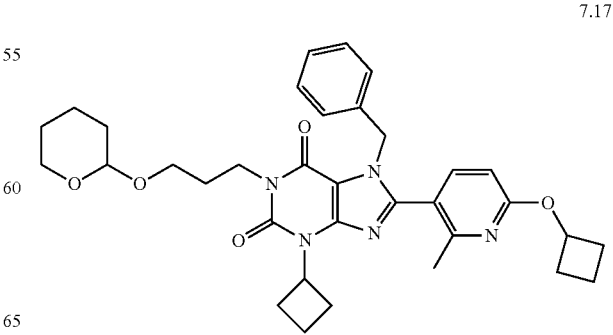

7.17

To a mixture of cyclobutanol (44.2 μL, 0.567 mmol) and sodium hydride (24.8 mg, 0.567 mmol) in DMF (1 mL) intermediate 6.12 (160 mg, 0.284 mmol) was added and the reaction was stirred 4.5 h at 50° C. H₂O was added and extracted with EtOAc. The combined organic layers were dried and concentrated in vacuo and the resulting crude product was used without further purification.

MS (ESI⁺): (M+H)⁺ 600/601

HPLC: RT=0.99 min, Method G

Intermediate 7.18

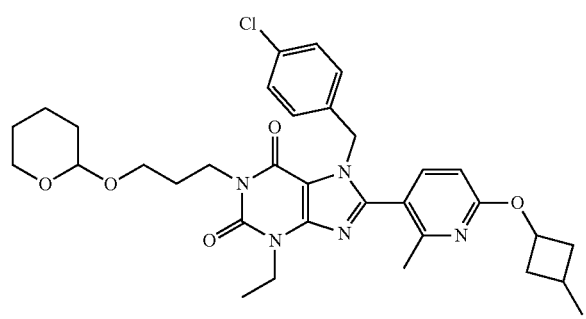

7.18

To a mixture of sodium hydride (55%, 12.2 mg, 0.28 mmol) in 3-methylcyclobutan-1-ol (0.3 ml) intermediate 6.3 (80 mg, 0.14 mmol) was added and the mixture was stirred 2 h at 100° C. H₂O was added and extracted with EtOAc. The combined organic layers were dried and concentrated in vacuo and the resulting crude product was used without further purification.

MS (ESI⁺): (M+H)⁺ 622

HPLC: RT=1.64 min, Method C

Intermediate 7.20

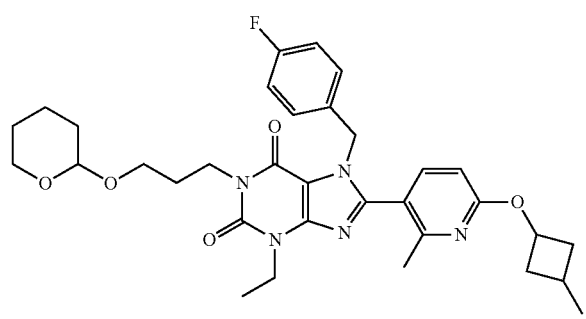

7.20

Intermediate 7.20 was prepared in an analogous manner to intermediate 7.11 using intermediate 6.4 and 3-methyl-cyclobutan-1-ol.

MS (ESI⁺): (M+H)⁺ 606/607

HPLC: RT=0.93 min, Method D

Intermediate 7.21

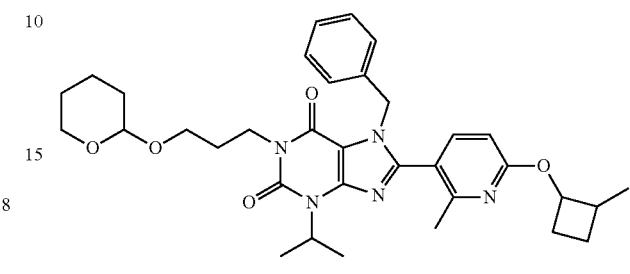

7.21

To a mixture of sodium hydride (55%, 14.2 mg, 0.33 mmol) in 2-methylcyclobutan-1-ol (0.5 ml) intermediate 6.2 (100 mg, 0.16 mmol) was added and the mixture was stirred 2 h at rt. H₂O was added and extracted with DCM. The combined organic layers were dried and concentrated in vacuo and the resulting crude product was used without further purification.

MS (ESI⁺): (M+H)⁺ 602/603

HPLC: RT=1.68 min, Method C

Intermediate 7.22

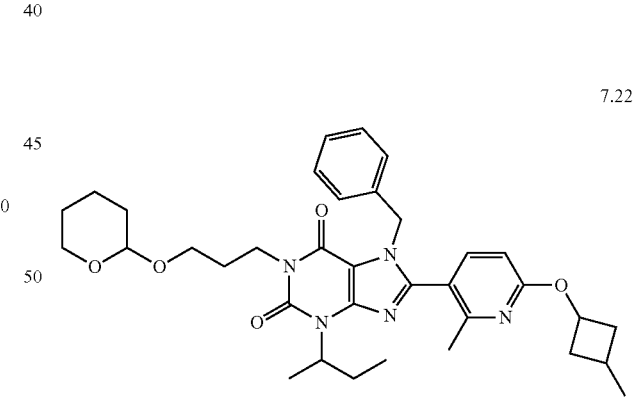

7.22

To a mixture of intermediate 15.2 (230 mg, 0.42 mmol) in THF (2.5 mL) 3-methylcyclobutan-1-ol (72 mg,) sodium hydride (60%, 33.5 mg, 0.84 mmol) was added and stirred 1 h at rt, 30 min at 40° C. and 1.5 h at 60° C. The mixture was cooled and used without further purification.

MS (ESI⁺): (M+H)+ 616

HPLC: RT=0.75 min, Method G

Intermediate 7.23

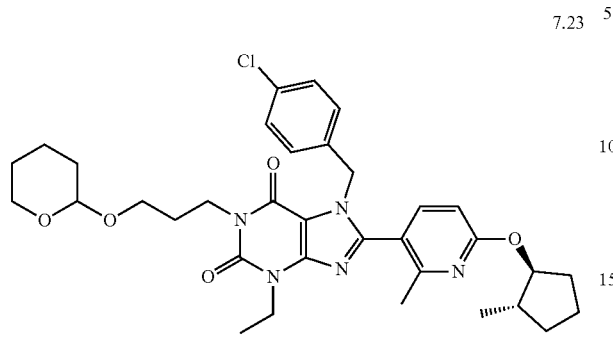

7.23

To a mixture of intermediate 6.3 (60 mg, 0.11 mmol) in dioxane (0.5 mL) trans-2-methylcyclopentan-1-ol (1 mL) and sodium hydride (55%, 9.2 mg, 0.21 mmol) were added. The mixture was stirred for 1.5 h at 100° C. H₂O was added and extracted with EtOAc. The combined organic layers were dried and concentrated in vacuo to obtain 13.1 mg of the product as a racemic mixture.

MS (ESI⁺): (M+H)⁺ 636

HPLC: RT=0.76 min, Method H

Intermediate 7.24

7.24

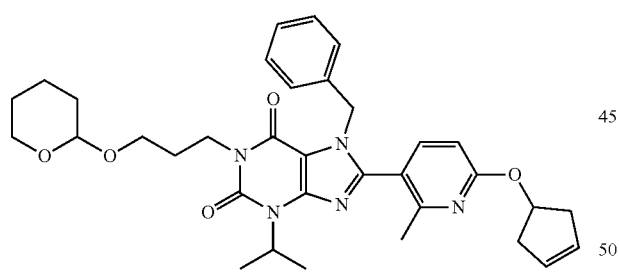

To a mixture of cyclopent-3-en-1-ol (21.3 mg, 0.25 mmol) and sodium hydride (11.1 mg, 0.25 mmol) in DMF (0.5 mL) intermediate 6.2 (70 mg, 0.13 mmol) was added and the reaction was stirred 1 h at 50° C. H₂O was added and extracted with DCM. The combined organic layers were dried and concentrated in vacuo and used without further purification.

MS (ESI⁺): (M+H)⁺ 600/601

HPLC: RT=0.64 min, Method E

Intermediate 7.25

7.25

To a mixture of sodium hydride (55%, 11.6 mg, 0.266 mmol) in cyclopentanol (0.5 ml) intermediate 6.3 (76 mg, 0.133 mmol) was added and the mixture was stirred 1.5 h at 100° C. H₂O was added and extracted with EtOAc. The combined organic layers were dried, concentrated in vacuo and purified by chromatography to obtain 26.2 mg of the product.

MS (ESI⁺): (M+H)⁺ 622

HPLC: RT=1.64 min, Method C

Intermediate 7.26

7.26

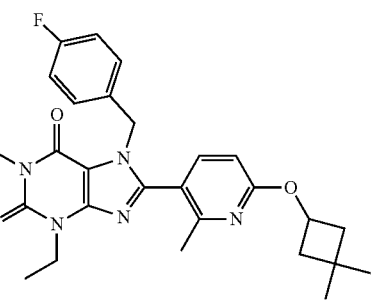

Intermediate 7.26 was prepared in an analogous manner to intermediate 7.21 using intermediate 6.4 and 3,3-dimethylcyclobutan-1-ol.

MS (ESI⁺): (M+H)+ 620/621

HPLC: RT=0.96 min, Method D

Intermediate 7.27

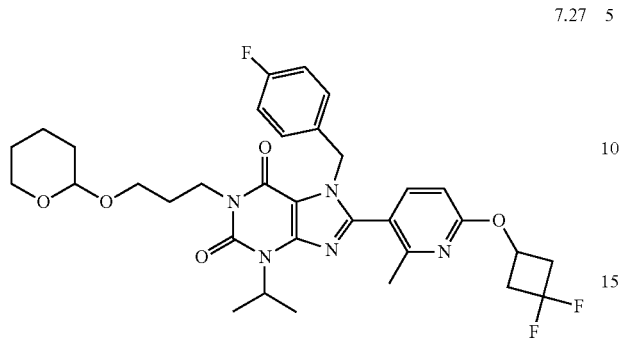

7.27

The reaction was performed under argon atmosphere.

A mixture of intermediate 6.1 (74 mg, 0.13 mmol), 5-(di-tert-butylphosphanyl)-1',3',5'-triphenyl-1'H-1,4'-bipyrazole (3.3 mg, 0.006 mmol), tris((1E,4E)-1,5-diphenyl-penta-1,4-dien-3-one)dipalladium (4.8 mg, 0.005 mmol), $Cs_2CO_3$ (42.3 mg, 0.13 mmol) and 3,3-difluorocyclobutan-1-ol (300 μL) in anhydrous dioxane (2 ml, 22.7 mmol) was stirred 45 min at 100° C. in the microwave. The mixture was filtered, concentrated in vacuo, the resulting crude product was purified by chromatography and freeze dried to obtain 53.0 mg of the product.

MS (ESI$^+$): (M+H)$^+$ 462/463

HPLC: RT=0.9 min, Method G

Intermediate 7.28

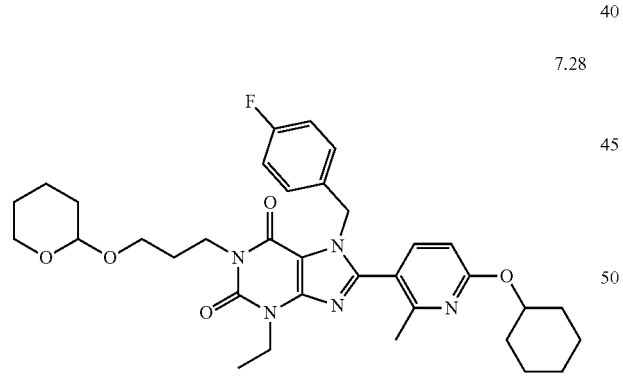

7.28

To a mixture of intermediate 6.4 (50 mg, 0.09 mmol) in cyclohexanol (0.5 mL, 4.8 mmol) and dioxane (1 ml, 11.3 mmol) sodium hydride (55%, 7.9 mg, 0.18 mmol) was added and the reaction was stirred 1 h at 110° C. $H_2O$ was added and extracted with EtOAc. The combined organic layers were dried and concentrated in vacuo and the resulting crude product was used without further purification.

MS (ESI$^+$): (M+H)$^+$ 620

HPLC: RT=0.95 min, Method F

Intermediate 7.29

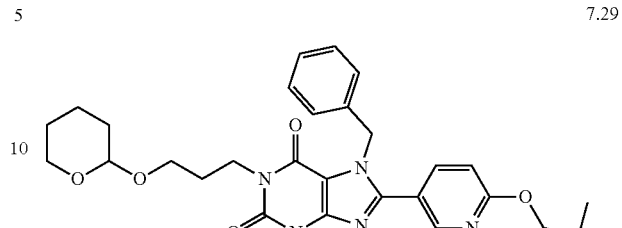

7.29

To a mixture of sodium hydride (55%, 11.4 mg, 0.26 mmol) in 2,2-dimethylcyclobutan-1-ol (0.5 ml) intermediate 6.16 (70 mg, 0.13 mmol) was added and the mixture was stirred 1 h at 50° C. $H_2O$ was added and extracted with DCM. The combined organic layers were dried, concentrated in vacuo and the resulting crude product used without further purification.

MS (ESI$^+$): (M+H)$^+$ 602/603

HPLC: RT=1.32 min, Method F

Intermediate 7.30

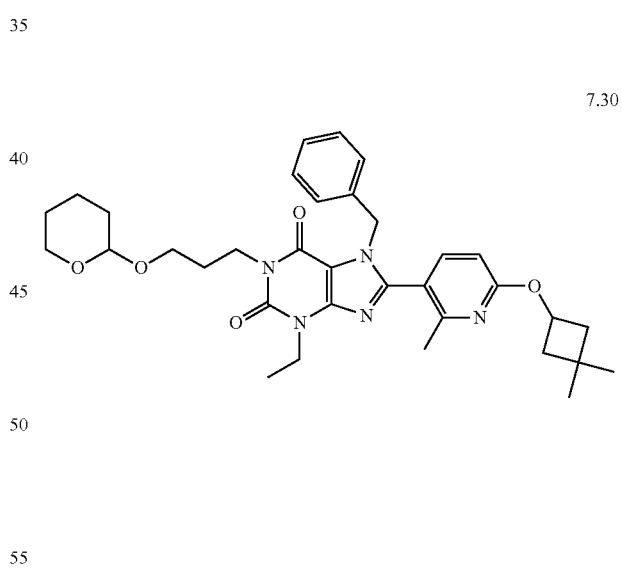

7.30

To a mixture of sodium hydride (55%, 11.4 mg, 0.26 mmol) in 3,3-dimethylcyclobutan-1-ol (0.5 ml) intermediate 6.16 (70 mg, 0.13 mmol) was added and the mixture was stirred 1 h at rt. Additional sodium hydride was added and the mixture was stirred 1 h at 50° C. $H_2O$ was added and extracted with DCM. The combined organic layers were dried, concentrated in vacuo and the resulting crude product was used without further purification.

MS (ESI$^+$): (M+H)$^+$ 602/603

HPLC: RT=1.29 min, Method F

Intermediate 7.31

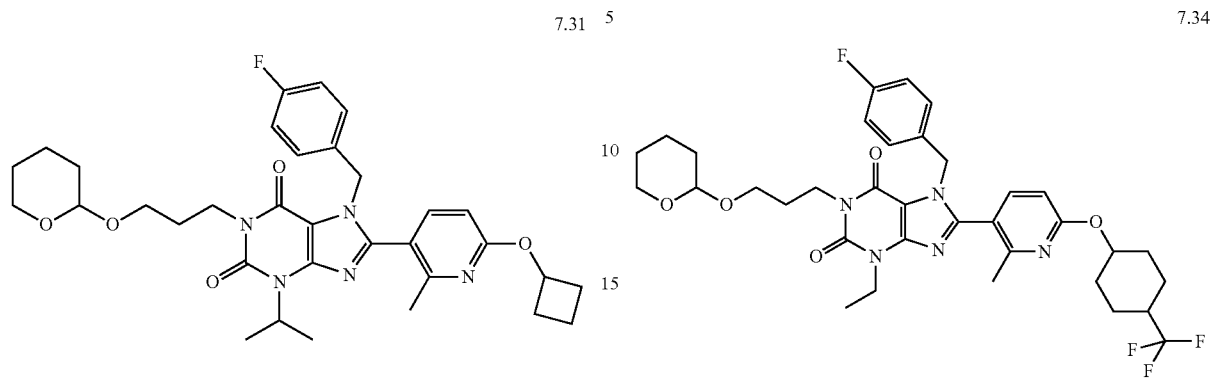

Intermediate 7.31 was prepared in an analogous manner to intermediate 7.21 using intermediate 6.1.

MS (ESI$^+$): (M+H)$^+$ 606

HPLC: RT=0.85 min, Method D

Intermediate 7.32

To a mixture of intermediate 6.16 (83 mg, 0.15 mmol) in dioxane (0.5 ml, 5.67 mmol) 3-methylcyclobutan-1-ol (0.5 mL) and sodium hydride (55%, 13.5 mg, 0.31 mmol) were added and the reaction was stirred 2 h at 100° C. H$_2$O was added and extracted with EtOAc. The combined organic layers were dried and concentrated in vacuo and used without further purification.

MS (ESI$^+$): (M+H)$^+$ 588

HPLC: RT=0.93 min, Method D

Intermediate 7.34

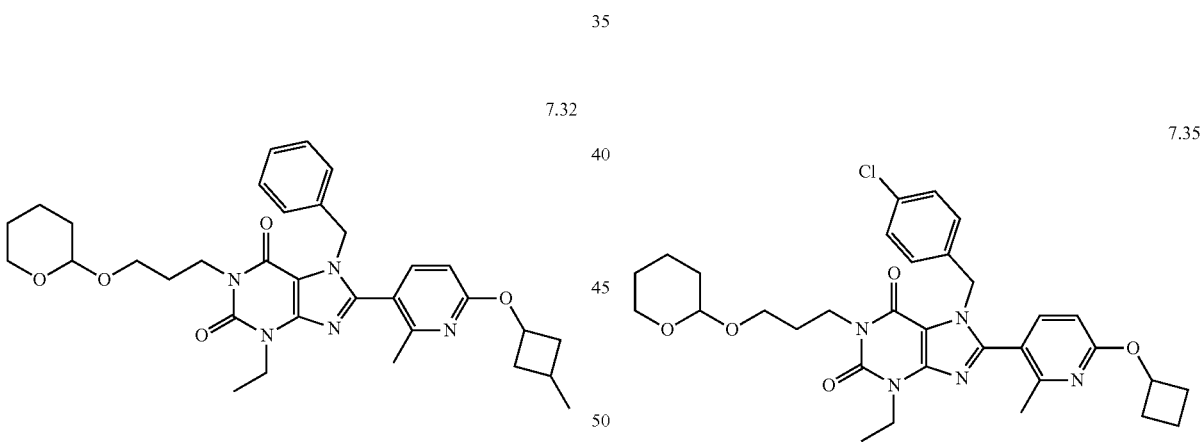

Intermediate 7.34 was prepared in an analogous manner to intermediate 7.6 using intermediate 6.4 and 4-(trifluoromethyl)cyclohexan-1-ol.

MS (ESI$^+$): (M+H)$^+$ 688/689

HPLC: RT=0.94 min, Method G

Intermediate 7.35

To a mixture of sodium hydride (55%, 12.7 mg, 0.29 mmol) in cyclobutanol (1.5 ml) intermediate 6.3 (83 mg, 0.145 mmol) was added and the mixture was stirred overnight at 100° C. H$_2$O was added and extracted with EtOAc. The combined organic layers were dried, concentrated in vacuo and the resulting crude product used without further purification.

MS (ESI$^+$): (M+H)+ 622

HPLC: RT=1.64 min, Method C

Intermediate 7.36

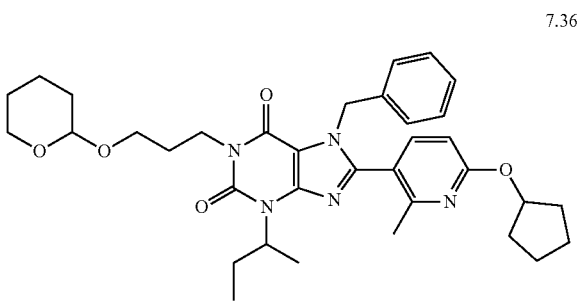 [SMILES: CCC(C)n1c(=O)n(CCCOC2CCCCO2)c(=O)c2c1nc(-c1ccc(OC3CCCC3)nc1C)n2Cc1ccccc1]

7.36

To a mixture of intermediate 15.2 (230 mg, 0.42 mmol) in THF (2.52 ml, 31.4 mmol) cyclopentanol (72 mg, 0.84 mmol) and sodium hydride (60%, 33.5 mg, 0.84 mmol) were added and the reaction was stirred 1 h at rt, 30 min at 40° C. and 1.5 h at 60° C. The mixture was cooled and used without further purification.

MS (ESI$^+$): (M+H)$^+$ 616

HPLC: RT=0.75 min, Method E

Intermediate 7.37

7.37

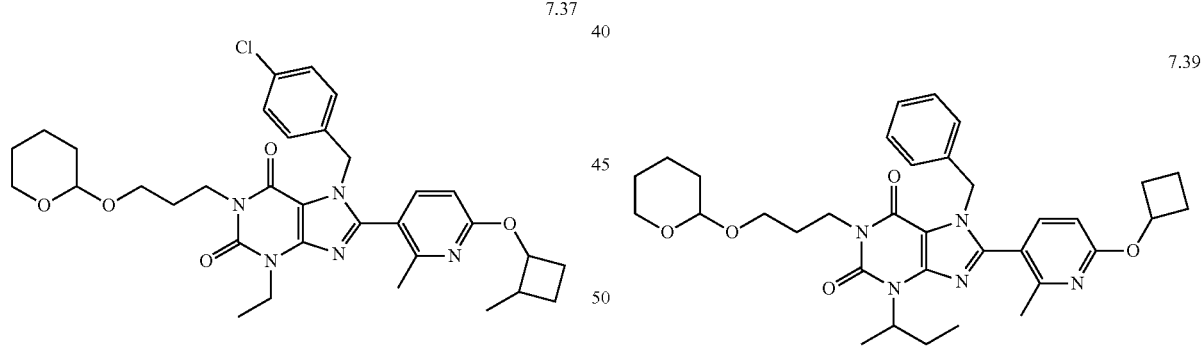

To a mixture of intermediate 6.20 (57 mg, 0.102 mmol) in dioxane (0.3 ml, 3.40 mmol) 2-methylcyclobutan-1-ol (0.2 mL) and sodium hydride (55%, 8.9 mg, 0.204 mmol) were added and the reaction was stirred 2 h at rt and 1 h at 40° C. H$_2$O was added and extracted with DCM. The combined organic layers were dried, concentrated and the resulting crude product used without further purification.

MS (ESI$^+$): (M+H)+ 608/610

HPLC: RT=1.62 min, Method C

Intermediate 7.38

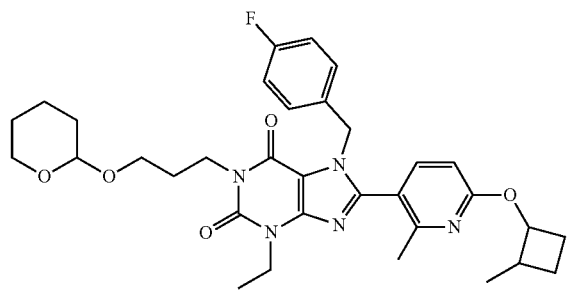

7.38

To a mixture of sodium hydride (55%, 9.3 mg, 0.214 mmol) in 2-methylcyclobutan-1-ol (0.3 ml) and DMF (0.3 mL) intermediate 6.4 (70 mg, 0.107 mmol) was added and the mixture was stirred 1 h at rt and 2 h at 50° C. H$_2$O was added and extracted with DCM. The combined organic layers were dried, concentrated in vacuo and the resulting crude product used without further purification.

MS (ESI$^+$): (M+H)$^+$ 606/607

HPLC: RT=1.6 min, Method C

Intermediate 7.39

7.39

To a mixture of intermediate 15.2 (230 mg, 0.42 mmol) in THF (2.52 ml, 31.4 mmol) cyclobutanol (60.4 mg, 0.84 mmol) and sodium hydride (60%, 33.5 mg, 0.84 mmol) were added and the reaction was stirred 1 h at rt, 30 min at 40° C. and 1.5 h at 60° C. The mixture was cooled and the resulting crude product was used without further purification.

MS (ESI$^+$): (M+H)$^+$ 602

HPLC: RT=0.69 min, Method E

Intermediate 7.40

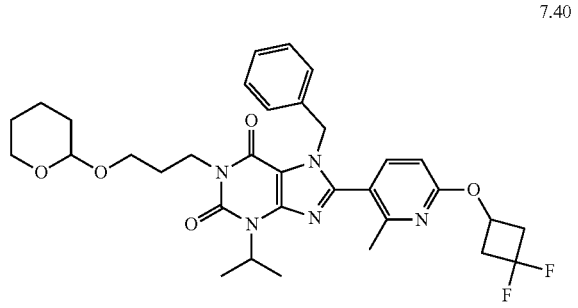 [SMILES: Cc1nc(OC2CC(F)(F)C2)ccc1-c1nc2c(c(=O)n(CCCOC3CCCCO3)c(=O)n2C(C)C)n1Cc1ccccc1]

The reaction was performed under argon atmosphere.

A mixture of intermediate 6.2 (70 mg, 0.127 mmol), 5-(di-tert-butylphosphanyl)-1',3',5'-triphenyl-1'H-1,4'-bipyrazole (3.21 mg, 0.006 mmol), tris((1E,4E)-1,5-diphenylpenta-1,4-dien-3-one)dipalladium (4.64 mg, 0.005 mmol), $Cs_2CO_3$ (41.3 mg, 0.127 mmol) and 3,3-difluorocyclobutan-1-ol (250 mg) in anhydrous dioxane (2 ml, 22.7 mmol) was stirred 45 min at 100° C. in the microwave. The mixture was filtered, concentrated in vacuo, purified by chromatography and freeze dried to obtain 61 mg of the product.

MS (ESI$^+$): (M+H)$^+$ 624/625

HPLC: RT=0.9 min, Method G

Intermediate 7.41

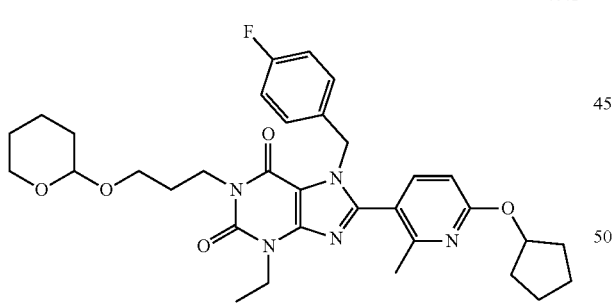

To a mixture of sodium hydride (55%, 11 mg, 0.252 mmol) in cyclopentanol (0.5 ml) intermediate 6.4 (70 mg, 0.126 mmol) was added and the mixture was stirred 2 h at rt. $H_2O$ was added and extracted with DCM. The combined organic layers were dried, concentrated and the resulting crude product used without further purification.

MS (ESI$^+$): (M+H)$^+$ 606/607

HPLC: RT=0.93 min, Method D

Intermediate 7.42

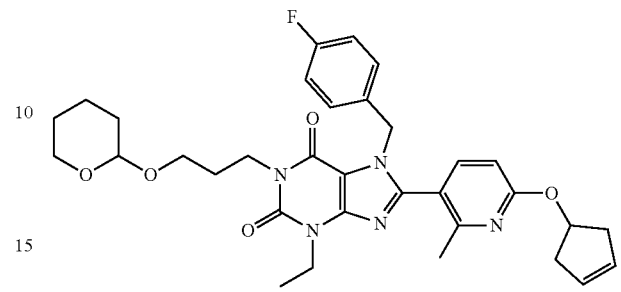

To a mixture of intermediate 6.4 (50 mg, 0.09 mmol) in dioxane (1 ml, 11.3 mmol) cyclopent-3-en-1-ol (0.5 mL) and sodium hydride (55%, 7.85 mg, 0.18 mmol) were added and the reaction was stirred 1 h at 110° C. $H_2O$ was added and extracted with EtOAc. The combined organic layers were dried, concentrated and the resulting crude product used without further purification.

MS (ESI$^+$): (M+H)$^+$ 604

HPLC: RT=0.88 min, Method G

Intermediate 7.43

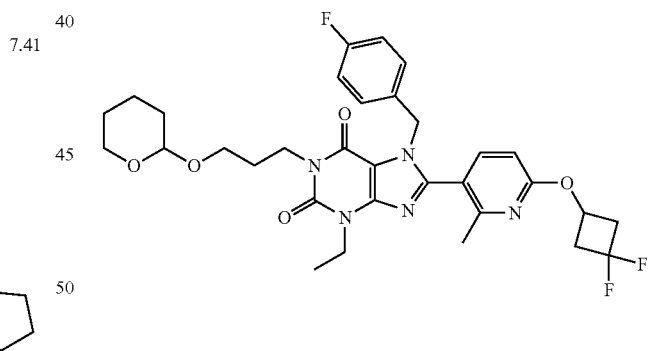

A mixture of intermediate 6.21 (80 mg, 0.126 mmol) and 3,3-difluorocyclobutan-1-ol (27.2 mg, 0.252 mmol) in anhydrous THF (0.5 ml, 6.2 mmol) was cooled to 0°, then potassium 2-methylpropan-2-olate (28.3 mg, 0.252 mmol) was added and the reaction was stirred 1 h under cooling. $H_2O$ was added and extracted with DCM. The combined organic layers were dried, concentrated and the resulting crude product used without further purification.

MS (ESI$^+$): (M+H)$^+$ 628/629

HPLC: RT=0.78 min, Method D

Intermediate 7.45

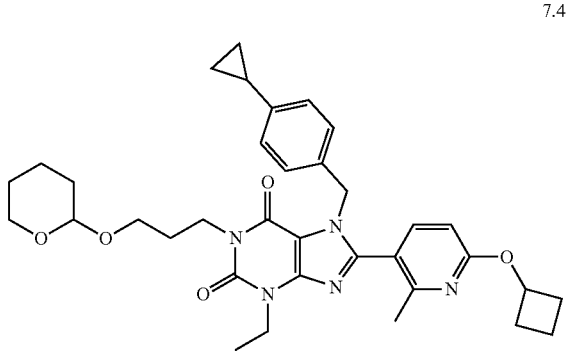

To a mixture of intermediate 6.22 (66 mg, 0.12 mmol) in dioxane (1 ml) cyclobutanol (0.5 mL) and sodium hydride (55%, 10.3 mg, 0.24 mmol) were added and the reaction was stirred 4.5 h at 110° C. H$_2$O was added and extracted with EtOAc. The combined organic layers were dried, concentrated and the resulting crude product used without further purification.

HPLC: RT=1.30 min, Method F

Intermediate 7.47

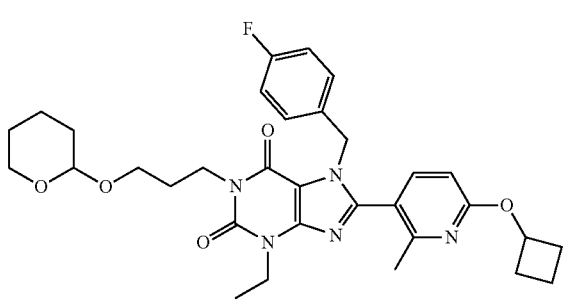

Intermediate 7.47 was prepared in an analogous manner to intermediate 7.41 using intermediate 6.4 and cyclobutanol.

MS (ESI$^+$): (M+H)$^+$ 606

HPLC: RT=0.9 min, Method D

Intermediate 7.48

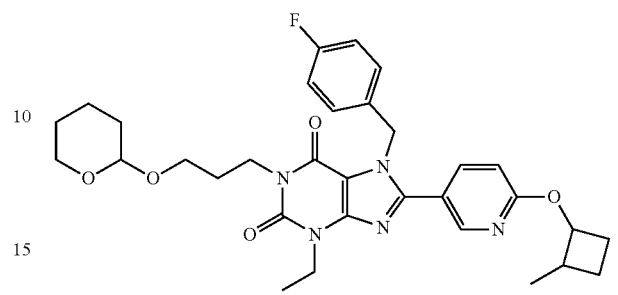

To a mixture of intermediate 6.25 (55 mg, 0.101 mmol) in dioxane (0.3 ml) 2-methylcyclobutan-1-ol (0.2 mL) and sodium hydride (55%, 8.86 mg, 0.203 mmol) were added and the reaction was stirred 1 h at 40° C. H$_2$O was added and extracted with DCM. The combined organic layers were dried, concentrated and the resulting crude product was used without further purification.

MS (ESI$^+$): (M+H)$^+$ 592/593

HPLC: RT=1.56 min, Method C

Intermediate 7.49

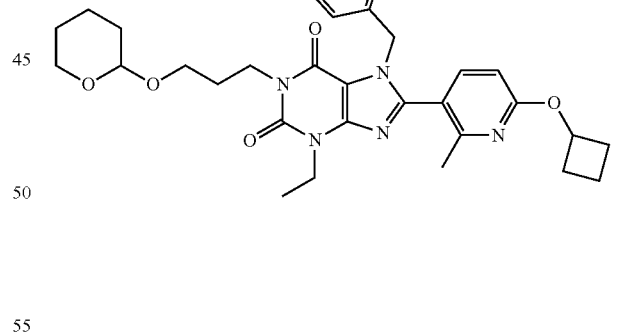

To a mixture of intermediate 6.16 (83 mg, 0.154 mmol) in dioxane (0.5 ml) cyclobutanol (2.0 mL) and sodium hydride (55%, 13.5 mg, 0.309 mmol) were added and the reaction was stirred 2 h at 100° C. H$_2$O was added and extracted with EtOAc. The combined organic layers were dried, concentrated and the resulting crude product was used without further purification.

MS (ESI$^+$): (M+H)$^+$ 574

HPLC: RT=0.89 min, Method D

Intermediate 7.50

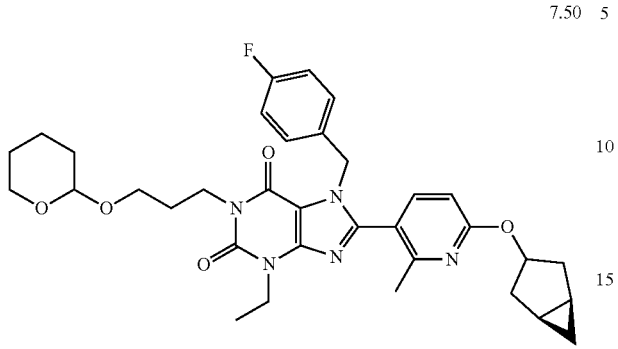

To a mixture of intermediate 6.4 (70 mg, 0.126 mmol) in DMF (1 ml) cis-bicyclo[3.1.0]hexan-3-ol (61.8 mg, 0.629 mmol) and sodium hydride (55%, 11 mg, 0.252 mmol) were added and the reaction was stirred 1 h at 50° C. Additional sodium hydride and (1R,5S)-bicyclo[3.1.0]hexan-3-ol were added and the mixture was stirred 1 h at 50° C. H$_2$O was added and extracted with DCM. The combined organic layers were dried, concentrated and the resulting crude product was used without further purification.

MS (ESI$^+$): (M+H)+ 618/619
HPLC: RT=0.94 min, Method G

Intermediate 7.51

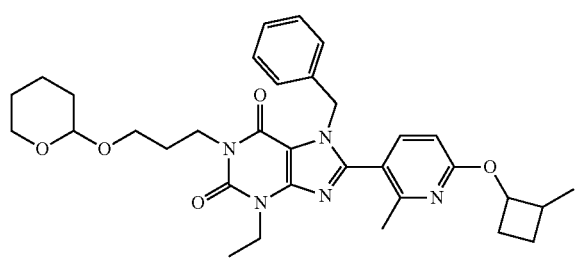

To a mixture of sodium hydride (55%, 13.8 mg, 0.316 mmol) in 2-methylcyclobutan-1-ol (0.5 ml) intermediate 6.16 (85 mg, 0.158 mmol) was added and the mixture was stirred 1.5 h at 100° C. H$_2$O was added and extracted with EtOAc. The combined organic layers were dried, concentrated and the resulting crude product was used without further purification.

MS (ESI$^+$): (M+H)$^+$ 588
HPLC: RT=0.94 min, Method D

Intermediate 7.52

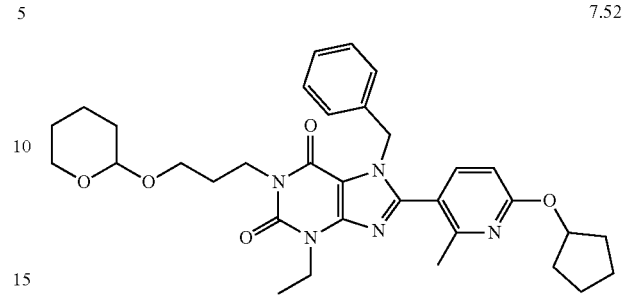

To a mixture of intermediate 6.16 (83 mg, 0.154 mmol) in dioxane (0.5 ml) cyclopentanol (0.5 mL) and sodium hydride (55%, 13.5 mg, 0.309 mmol) were added and the reaction was stirred 6 h at 100° C. H$_2$O was added and extracted with EtOAc. The combined organic layers were dried, concentrated and the resulting crude product was used without further purification.

MS (ESI$^+$): (M+H)$^+$ 588
HPLC: RT=0.93 min, Method D

Intermediate 7.53

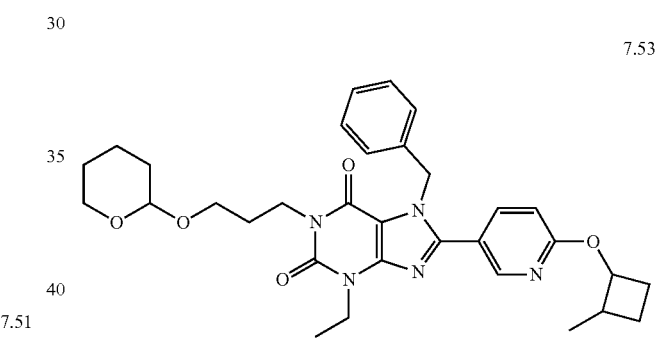

To a mixture of intermediate 6.27 (54 mg, 0.067 mmol) in dioxane (0.3 ml) 2-methylcyclobutan-1-ol (0.2 mL) and sodium hydride (55%, 5.9 mg, 0.134 mmol) were added and the reaction was stirred 2 h at rt and 1 h at 40° C. H$_2$O was added and extracted with DCM. The combined organic layers were dried, concentrated in vacuo and the resulting crude product was used without further purification.

MS (ESI$^+$): (M+H)$^+$ 574/575
HPLC: RT=1.56 min, Method C

Intermediate 8.1

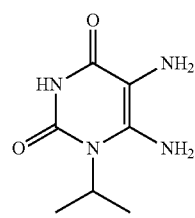

To a mixture of 2.1 (2.5 g, 12.62 mmol) in NaOH (1 mol/L, 30 mL, 30 mmol) hydrazine hydrate (1.16 mL, 23.34 mmol) was added and cooled to 0° C. Then raney nickel was added and the mixture was stirred for 1 h at 0° C. The mixture was cooled, acidified to a pH of 7-8 with conc. HCl, the obtained precipitate was filtered, washed with H₂O (50 mL) and tert-butylmethylether (50 mL) and dried to obtain 2.15 g the product.

MS (ESI⁺): (M+H) 185

HPLC: RT=0.15 min, Method F

Intermediate 9.1

After stirring a mixture of cyclobutanol (0.31 mL, 3.8 mmol) and sodium hydride (91.2 mg, 3.8 mmol) for 5 min DMF (2 ml, 25 mmol) 2-chloro-6-fluoropyridine (250 mg, 1.9 mmol) was added and the mixture was stirred for 1 h at rt. H₂O was added and extracted with DCM. The combined organic layers were dried and concentrated in vacuo. The crude product was purified by chromatography to obtain 245 mg of the product.

MS (ESI⁺): (M+H)⁺ 184/186

HPLC: RT=0.69 min, Method F

Intermediate 9.2

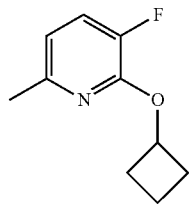

The reaction was performed under argon atmosphere.

To a mixture of Pd(OAc)₂ (118 mg, 0.526 mmol) and {[1,1'-binaphthalene]-2-yl}di-tert-butyl)phosphane (210 mg, 0.526 mmol) in anhydrous dioxane (20 mL, 227 mmol) 2-bromo-3-fluoro-6-methylpyridine (1.0 g, 5.263 mmol), cyclobutanol (821 μL, 10.526 mmol) and Cs₂CO₃ (1.715 g, 5.263 mmol) were added after 5 min. The reaction mixture was stirred 45 min at 140° C. in the microwave. The mixture was filtered, concentrated in vacuo and purified by chromatography to obtain 270 mg of the product.

MS (ESI⁺): (M+H)⁺ 182/183

HPLC: RT=0.72 min, Method G

Intermediate 9.3

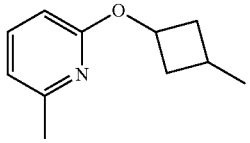

After stirring a mixture of 3-methylcyclobutan-1-ol (0.25 mL, 2.7 mmol) and sodium hydride (55%, 236 mg, 5.4 mmol) in DMF (5 ml, 61.5 mmol) for 10 min 2-fluoro-6-methylpyridine (300 mg, 2.7 mmol) was added and the mixture was stirred for 1 h at rt. H₂O was added and extracted with diethylether. The combined organic layers were dried and concentrated and the resulting crude product was used without further purification.

MS (ESI⁺): (M+H)⁺ 178/179

HPLC: RT=0.54 min, Method F

Intermediate 9.4

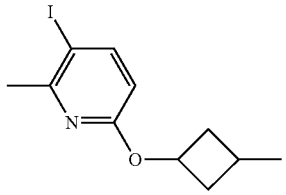

To a mixture of 6-fluoro-3-iodo-2-methylpyridine (237 mg, 1.0 mmol) and 3-methylcyclobutan-1-ol (103 mg, 1.2 mmol) in THF (2 mL, 25 mmol) (tert-butoxy)potassium (224 mg, 2.0 mmol) was added at 0° C. The mixture was stirred 15 min at 0° C. H2O was added and extracted with EtOAc. The combined organic layers were dried and concentrated in vacuo to obtain 250 mg of the product.

HPLC: RT=1.407/1.724 min cis/trans, Method K

Intermediate 9.5

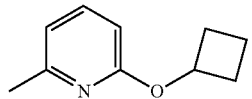

After stirring a mixture of cyclobutanol (1.05 mL, 13.5 mmol) and sodium hydride (55%, 1178 mg, 27 mmol) for 10 min DMF (10 ml, 123 mmol) 2-fluoro-6-methylpyridine (1.5 g, 13.5 mmol) was added and the mixture was stirred for 1 h at rt. Additional sodium hydride was added and the mixture was stirred 1 h at 50° C. H₂O was added and extracted with diethylether. The combined organic layers were dried, concentrated and the resulting crude product was used without further purification.

MS (ESI⁺): (M+H)⁺ 164

HPLC: RT=0.38 min, Method F

Intermediate 9.6

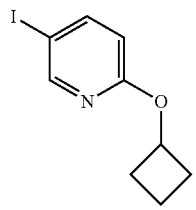

9.6

To a mixture of cyclobutanol (8.14 mL, 104.4 mmol) in THF (25.1 mL, 313.2 mmol) sodium hydride (60%, 835.2 mg, 20.8 mmol) was added and stirred for 20 min at 60° C. Then 2-chloro-5-iodopyridine (5.0 g, 20.8 mmol) was added and the mixture was stirred overnight at 60° C. The mixture was cooled, filtered and concentrated in vacuo. The crude product was purified by chromatography to obtain 2.60 g the product.
MS (ESI$^+$): (M+H)$^+$ 276
HPLC: RT=0.76 min, Method D Intermediate 9.7

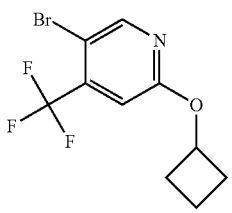

9.7

To a mixture of 5-bromo-2-chloro-4-(trifluoromethyl) pyridine (521 mg, 2.0 mmol) and cyclobutanol (313.2 µL, 4 mmol) in THF (2.4 mL, 30 mmol) potassium 2-methylpropan-2-olate (247 mg, 2.2 mmol) was added and the mixture was stirred 20 min at rt. H$_2$O was added and extracted with DCM. The combined organic layers were dried and concentrated in vacuo to obtain 845 mg of the product.
MS (ESI$^+$): (M+H)$^+$ 297
HPLC: RT=1.22 min, Method G Intermediate 9.8

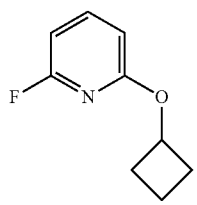

9.8

To a mixture of 2,6-difluoropyridine (1.0 g, 8.69 mmol) and cyclobutanol (627 mg, 8.69 mmol) in DMF (8 mL) sodium hydride (379 mg, 8.69 mmol) was added and the mixture was stirred overnight at rt. H$_2$O was added and extracted with EtOAc. The combined organic layers were dried and concentrated in vacuo. The crude product was purified by chromatography to obtain 1.0 g of the product.
MS (ESI$^+$): (M+H)$^+$ 116
HPLC: RT=0.58 min, Method F Intermediate 10.1

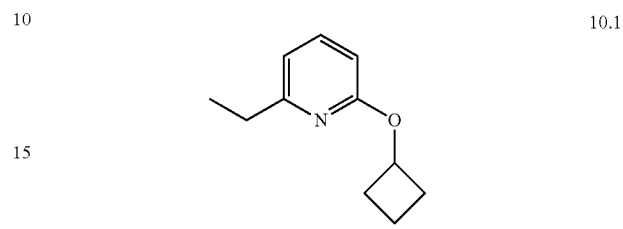

10.1

The reaction was performed under argon atmosphere.
To a mixture of intermediate 9.1 (1.52 g, 8.28 mmol), potassium ethyltrifluoroboranuide (2.25 g, 16.57 mmol) and K$_2$CO$_3$ (3.43 g, 24.85 mmol) in toluene/H$_2$O (10/1, 12 mL) Pd(OAc)$_2$ (93 mg, 0.41 mmol) and X-Phos were added and the mixture was stirred for 10 h at 140° C. The mixture was filtered, concentrated in vacuo and purified by chromatography to obtain 885 mg of the product.
MS (ESI$^+$): (M+H)$^+$ 178/179
HPLC: RT=0.54 min, Method F Intermediate 11.1

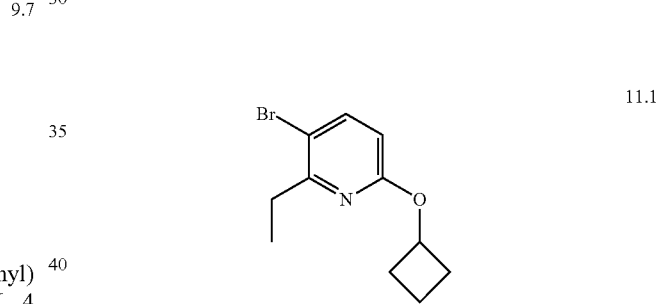

11.1

To a mixture of intermediate 10.1 (90 mg, 0.11 mmol) anhydrous DMF (10 mL, 122.9 mmol) 1-bromopyrrolidine-2,5-dione (909 mg, 5.11 mmol) was added and the mixture was stirred for 2.5 h at rt. Na$_2$S$_2$O$_3$ solution (10%) was added and extracted with DCM. The combined organic layers were dried and concentrated in vacuo. The crude product was purified by chromatography to obtain 905 mg of the product.
MS (ESI$^+$): (M+H)*256/258
HPLC: RT=1.25 min, Method F Intermediate 11.2

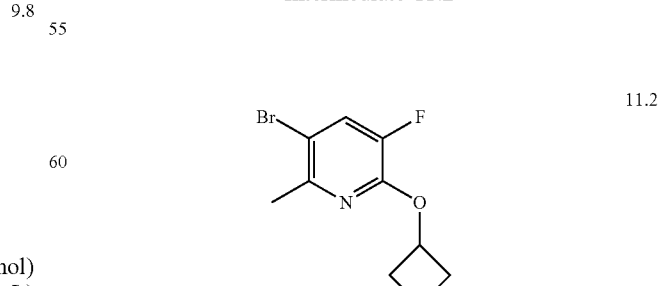

11.2

To a mixture of intermediate 9.2 (220 mg, 1.21 mmol) in anhydrous DMF (3 mL, 36.9 mmol) 1-bromopyrrolidine-2,5-dione (259 mg, 1.46 mmol) was added and the mixture was stirred for 2 h at 60° C. Na$_2$S$_2$O$_3$ solution (10%) was added and extracted with DCM. The combined organic layers were dried and concentrated in vacuo. The crude product was purified by chromatography to obtain 116 mg of the product.

HPLC: RT=0.85 min, Method G

Intermediate 11.3

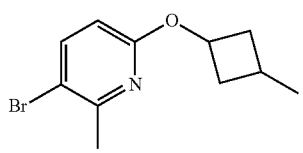

11.3

The reaction was performed under argon atmosphere.

To a mixture of intermediate 9.3 (478 mg, 2.7 mmol) in anhydrous THF (30 mL, 374 mmol) 1,3-dibromo-5,5-dimethylimidazolidine-2,4-dione (1.16 g, 4.05 mmol) was added and the mixture was stirred overnight at rt. Na$_2$S$_2$O$_3$ solution was added, evaporated the THF and extracted with DCM. The combined organic layers were dried and concentrated in vacuo. The crude product was purified by chromatography to obtain 498 mg of the product.

MS (ESI$^+$): (M+H)$^+$ 256/258

HPLC: RT=1.21 min, Method F

Intermediate 11.4

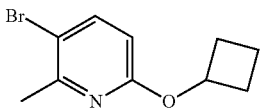

11.4

The reaction was performed under argon atmosphere.

To a mixture of intermediate 9.5 (2.59 g, 13.5 mmol) in anhydrous THF (100 mL, 1247 mmol) 1,3-dibromo-5,5-dimethylimidazolidine-2,4-dione (5.78 g, 20.2 mmol) was added and the mixture was stirred overnight at rt. Na$_2$S$_2$O$_3$ solution was added, evaporated the THF and extracted with DCM. The combined organic layers were dried and concentrated in vacuo. The crude product was purified by chromatography to obtain 2.27 g of the product.

MS (ESI$^+$): (M+H)$^+$ 242/244

HPLC: RT=1.14 min, Method F

Intermediate 11.5

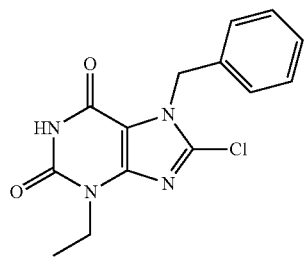

11.5

To a mixture of intermediate 4.11 (722 mg, 2.23 mmol) in anhydrous THF (25 mL) 1-chloropyrrolidine-2,5-dione (0.33 g, 2.45 mmol) was added and the mixture was stirred overnight at 60° C. The mixture was concentrated in vacuo, H$_2$O was added and the obtained precipitate was filtered and dried to obtain 633 mg the product.

MS (ESI$^+$): (M+H)+ 305/307

HPLC: RT=0.7 min, Method G

Intermediate 11.6

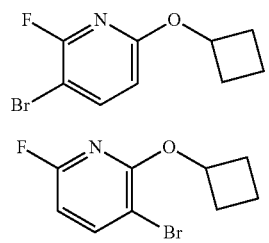

To a mixture of intermediate 9.8 (300 mg, 1.79 mmol) in DCM (5 mL) 1-bromopyrrolidine-2,5-dione (319 mg, 1.79 mmol) was added and the mixture was stirred 1 h at 50° C. Additional 1-bromopyrrolidine-2,5-dione and DMF (1 mL) were added and the mixture was stirred overnight at 50° C. and 3 d at rt. The mixture was concentrated in vacuo and purified by chromatography to obtain 389 mg of the product as a 70/30 (11.6.1/11.6.2) mixture of regioisomers.

MS (ESI$^+$): (M+H)$^+$ 246

HPLC: RT=1.09 min, Method F

Intermediate 12.1

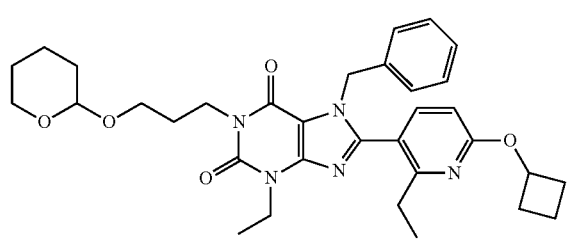

12.1

The reaction was performed under argon atmosphere.

To a mixture of intermediate 6.5 (107 mg, 0.22 mmol) and intermediate 11.1 (56.5 mg, 0.22 mmol) in anhydrous THF (195 µL, 2.43 mmol) and anhydrous DMF (412 µL, 5.07 mmol) K$_2$CO$_3$ (61 mg, 0.44 mmol), tricyclohexylphosphane (25 mg, 0.088 mmol), Pd(OAc)$_2$ (10 mg, 0.044 mmol) and CuI (126 mg, 0.66 mmol) were added and the mixture was stirred overnight at 130° C. MeOH was added, filtered and concentrated in vacuo. H$_2$O was added and extracted with DCM. The combined organic layers were dried and concentrated in vacuo. The crude product was purified by chromatography to obtain 44.0 mg of the product.

MS (ESI$^+$): (M+H)$^+$ 588/589
HPLC: RT=0.95 min, Method G

Intermediate 12.2

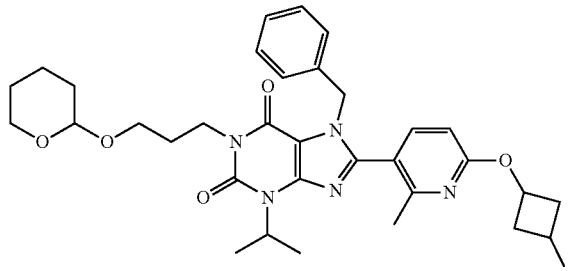

12.2

The reaction was performed under argon atmosphere.

To a mixture of intermediate 6.15 (100 mg, 0.234 mmol) and intermediate 11.3 (60.1 mg, 0.234 mmol) in anhydrous THF (200 µL, 2.49 mmol) and anhydrous DMF (400 µL, 4.92 mmol) K$_2$CO$_3$ (65 mg, 0.469 mmol), tricyclohexylphosphane (26 mg, 0.094 mmol), Pd(OAc)$_2$ (10.5 mg, 0.047 mmol) and CuI (134 mg, 0.703 mmol) were added and the mixture was stirred 2 d at 130° C. H$_2$O was added and extracted with EtOAc. The combined organic layers were dried and concentrated in vacuo. The crude product was purified by chromatography and freeze dried to obtain 35.0 mg the product.

MS (ESI$^+$): (M+H)$^+$ 602
HPLC: RT=1.32 min, Method F

Intermediate 12.3

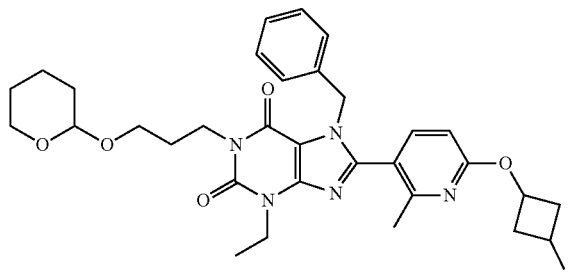

12.3

The reaction was performed under argon atmosphere.

To a mixture of intermediate 6.5 (310 mg, 0.752 mmol) and intermediate 9.4 (190 mg, 0.627 mmol) in anhydrous THF (2 mL, 25 mmol) and anhydrous DMF (2 mL, 25 mmol) K$_2$CO$_3$ (173 mg, 1.254 mmol), tricyclohexylphosphane (70 mg, 0.251 mmol), Pd(OAc)$_2$ (28 mg, 0.125 mmol) and CuI (358 mg, 1.88 mmol) were added and the mixture was stirred overnight at 125° C. The mixture was cooled and purified by silica column and further purified by chromatography to obtain 57.0 mg of the product.

MS (ESI$^+$): (M+H)$^+$ 588
HPLC: RT=0.92 min, Method D

Intermediate 12.4

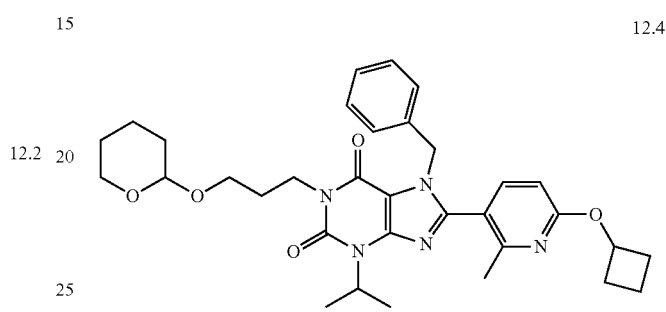

12.4

The reaction was performed under argon atmosphere.

To a mixture of intermediate 6.15 (220 mg, 0.52 mmol) and intermediate 11.4 (125 mg, 0.52 mmol) in anhydrous THF (400 µL, 5 mmol) and anhydrous DMF (800 µL, 9.8 mmol) K$_2$CO$_3$ (143 mg, 1.03 mmol), tricyclohexylphosphane (58 mg, 0.206 mmol), Pd(OAc)$_2$ (23 mg, 0.103 mmol) and CuI (295 mg, 1.55 mmol) were added and the mixture was stirred overnight at 130° C. H$_2$O was added, the mixture was basified with NH$_3$ and extracted with EtOAc. The combined organic layers were dried and concentrated in vacuo. The crude product was purified by chromatography to obtain 121 mg of the product.

MS (ESI$^+$): (M+H)$^+$ 589/590
HPLC: RT=0.8 min, Method F

Intermediate 12.5

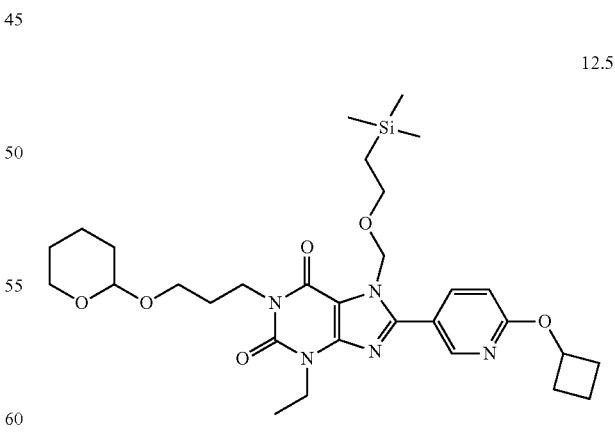

12.5

The reaction was performed under argon atmosphere.

To a mixture of intermediate 6.18 (700 mg, 1.55 mmol) and intermediate 9.6 (850 mg, 3.09 mmol) in anhydrous THF (9.92 mL, 124 mmol) and anhydrous DMF (5 mL, 62 mmol) K$_2$CO$_3$ (428 mg, 3.09 mmol), tricyclohexylphosphane (162 mg, 0.62 mmol), Pd(OAc)$_2$ (69 mg, 0.309 mmol)

and CuI (884 mg, 4.64 mmol) were added and the mixture was stirred 4 h at 180° C. H$_2$O was added and extracted with DCM. The combined organic layers were dried and concentrated in vacuo. The crude product was purified by chromatography to obtain 221 mg of the product.

MS (ESI$^+$): (M+H)$^+$ 600

HPLC: RT=0.99 min, Method D

Intermediate 12.6

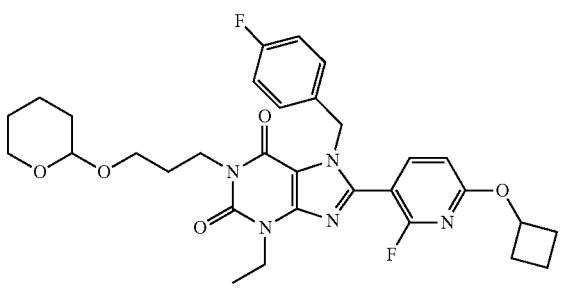

12.6

The reaction was performed under argon atmosphere.

To a mixture of intermediate 6.26 (80 mg, 0.19 mmol) and intermediate 11.6 (50.3 mg, 0.20 mmol) in anhydrous THF (164 µL, 2.04 mmol) and anhydrous DMF (348 µL, 4.27 mmol) K$_2$CO$_3$ (51.4 mg, 0.372 mmol), tricyclohexylphosphane (20.9 mg, 0.074 mmol), Pd(OAc)$_2$ (8.3 mg, 0.037 mmol) and CuI (106 mg, 0.558 mmol) were added and the mixture was stirred overnight at 130° C. The mixture was filtered, washed with ACN and DMF and purified by chromatography to obtain 42.3 mg of the product.

MS (ESI$^+$): (M+H)$^+$ 596

Intermediate 13.1

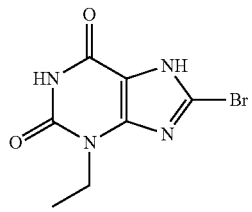

13.1

To a mixture of intermediate 4.3 (230 mg, 1.277 mmol) in HOAc (5 mL) sodium acetate (209.5 mg, 2.553 mmol) was added and the mixture was warmed to 50° C. To this mixture a solution of dibromine (131 µL, 2.553 mmol) in HOAc (5 mL) was added and the reaction mixture was stirred for 1 h at 50° C. Water was added, the obtained precipitate was filtered, washed with water and dried to obtain 90.0 mg of the product.

MS (ESI$^+$): (M+H)+ 261/262

HPLC: RT=0.37 min, Method F

Intermediate 13.2

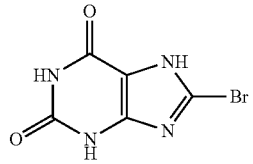

13.2

To a mixture of intermediate 4.8 (7.42 g, 35.74 mmol) in H$_2$O (35.4 mL, 1.97 mol) dibromine (2.75 mL, 53.62 mmol) was added and the mixture was stirred overnight at 100° C. in a closed vial. The mixture was cooled, H$_2$O was added (200 mL) and the obtained precipitate was filtered, washed with H$_2$O and tert-butylmethylether and dried to obtain 3.05 g of the product.

MS (ESI$^+$): (M+H)$^+$ 232

HPLC: RT=0.24 min, Method F

Intermediate 14.1

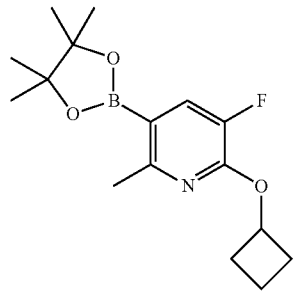

14.1

The reaction was performed under argon atmosphere.

A mixture of intermediate 11.2 (76 mg, 0.292 mmol), 4,4,5,5-tetramethyl-2-(4,4,5,5-tetramethyl-1,3,2-dioxaborolan-2-yl)-1,3,2-dioxaborolane (80.2 mg), potassium acetate (86.1 mg, 0.877 mmol) and 1,1'-bis(diphenylphosphino)ferrocene-palladium(II)dichloride dichloromethane complex (7.2 mg, 0.009 mmol) in dioxane (1 mL) was stirred overnight at 50° C. The mixture was filtered and concentrated in vacuo. H$_2$O was added and extracted with DCM. The combined organic layers were filtered over a silica column, dried and concentrated in vacuo to obtain 85.0 mg of the product.

MS (ESI$^+$): (M+H)$^+$ 308/309

HPLC: RT=0.94 min, Method G

Intermediate 15.1

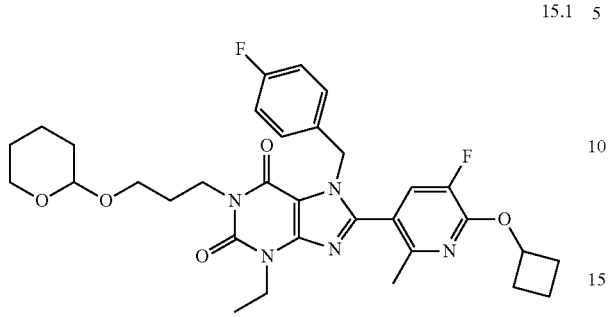

15.1

The reaction was performed under argon atmosphere.

To a mixture of intermediate 6.9 (112 mg, 0.22 mmol) and intermediate 14.1 (104 mg, 0.22 mmol) in THF (2 mL, 25 mmol) K3PO4 (1 mol/L, 0.44 mL, 0.44 mmol) was added and after 5 min dicyclohexyl[2',4',6'-tris(propan-2-yl)-[1,1'-biphenyl]-2-yl]phosphane {2'-amino-[1,1'-biphenyl]-2-yl}palladiumylium methanesulfonate (18.6 mg, 0.022 mmol) was added and the reaction mixture was stirred for 5 h at 100° C. The mixture was filtered, washed with MeOH and concentrated in vacuo. The crude product was purified by chromatography to obtain 35 mg of the product.

MS (ESI$^+$): (M+H)+ 610/611

HPLC: RT=1.26 min, Method F

Intermediate 15.2

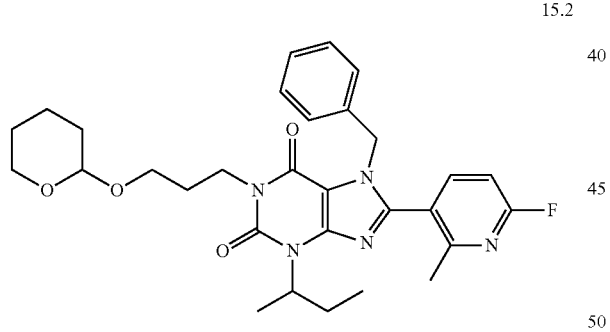

15.2

The reaction was performed under argon atmosphere.

To a mixture of intermediate 6.14 (810 mg, 1.56 mmol) in dioxane (34.4 mL, 390 mmol) [1,1'-Bis(diphenylphosphino)ferrocene]dichloropalladium(II), complex with dichloromethane (1:1, 255 mg, 0.31 mmol) was added and after 5 min (6-fluoro-2-methylpyridin-3-yl)boronic acid (314 mg, 2.03 mmol) and Cs$_2$CO$_3$ (2 mol/L, 1.56 mL, 3.12 mmol) were added and the mixture was stirred 3 h at 100° C. The mixture was cooled, filtered and washed with MeOH/ACN (1/1). Thiolpolymer (1 g) was added, the mixture was filtered again and washed with MeOH/ACN (1/1). The crude product was purified by chromatography to obtain 700 mg of the product.

MS (ESI$^+$): (M+H)$^+$ 550

HPLC: RT=0.83 min, Method G

Intermediate 15.3

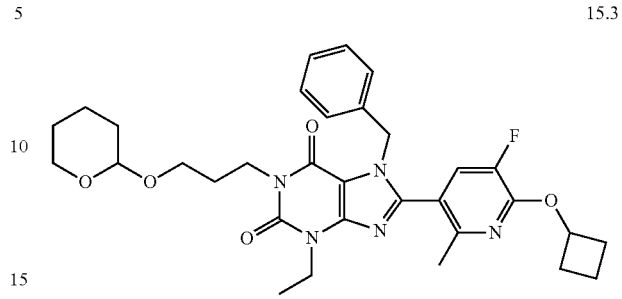

15.3

The reaction was performed under argon atmosphere.

To a mixture of intermediate 6.19 (100 mg, 0.22 mmol) and intermediate 14.1 (82 mg, 0.17 mmol) in THF (2 mL, 25 mmol) K$_3$PO$_4$ (0.5 mol/L, 0.9 mL, 0.45 mmol) was added and after 5 min (2-dicyclohexyphosphino-2',4',6'-trisisopropyl)-1,1'-biphenyl)[2-(2'-amino-1,1'-biphenyl)]palladium (II) methanesulfonate (18.9 mg, 0.022 mmol) was added and the reaction mixture was stirred 5 h at 100° C. The mixture was filtered, washed with MeOH and concentrated in vacuo. The crude product was purified by chromatography to obtain 58.0 mg of the product.

MS (ESI$^+$): (M+H)$^+$ 592/593

HPLC: RT=0.9 min, Method G

Intermediate 16.1

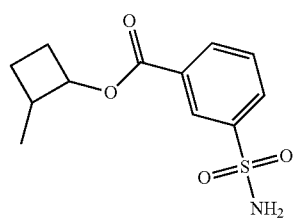

16.1

To a mixture of 3-sulfamoylbenzoic acid (70.1 mg, 0.348 mmol) and DMAP (4.4 mg, 0.036 mmol) in DMF (0.5 mL) 2-methylcyclobutan-1-ol (30 mg, 0.348 mmol) and DCC (86.5 mg, 0.415 mmol) were added and the mixture was stirred 1 h. H$_2$O was added and the mixture extracted with DCM. The combined organic layers were dried, concentrated in vacuo and purified by chromatography to obtain 21.0 mg the product as a diastereomeric mixture.

MS (ESI$^+$): (M+H)$^+$ 268/269

HPLC: RT=0.53/0.54 min, Method D

Intermediate 19.1

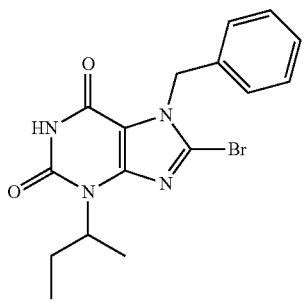

19.1

A mixture of intermediate 5.14 (1.7 g, 5.29 mmol) in DMF (22 mL, 270 mmol) was warmed to 50° C. Then sodium hydride (60%, 211.8 mg, 5.29 mmol) was added and stirred 30 min at 50° C. Additional DMF (7.3 mL, 90 mmol) and 2-iodobutane (3.05 mL, 26.5 mmol) were added and the mixture was stirred 3 h at 80° C. The mixture was cooled and purified by chromatography to obtain 700.0 mg of the product.

MS (ESI$^+$): (M+H)$^+$ 379

HPLC: RT=0.63 min, Method G

Intermediate 19.2

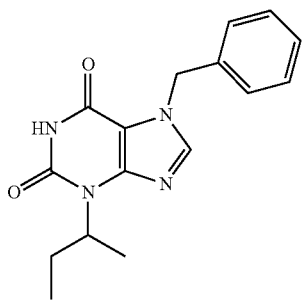

19.2

A mixture of intermediate 21.1 (2 g, 8.26 mmol) in DMF (45 mL, 553 mmol) was warmed to 50° C. Then sodium hydride (55%, 360.3 mg, 8.23 mmol) was added and stirred 1 h at 50° C. 2-iodopropane (4.13 mL, 41.28 mmol) were added and the mixture was stirred 1 h at 80° C. The mixture was cooled, purified by chromatography and freeze dried to obtain 661 mg of the product.

MS (ESI$^+$): (M+H)+ 285/286

HPLC: RT=0.65 min, Method F

Intermediate 20.1

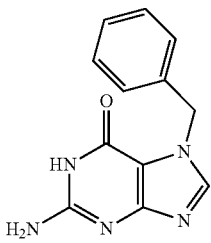

20.1

To a mixture of 2-amino-9-[(2R,3R,4S,5R)-3,4-dihydroxy-5-(hydroxymethyl)oxolan-2-yl]-6,9-dihydro-1H-purin-6-one (60 g, 211.8 mmol) in DMSO (160 ml, 2.25 mol) (bromomethyl)benzene (30.2 ml, 254.2 mmol) was added dropwise and the mixture was stirred 4 h at 50° C. The mixture was cooled and HCl (4 mol/l, 122 mL, 487.2 mmol) was added dropwise and the mixture was stirred 2 h at 70° C. The mixture was cooled, filtered, washed with MeOH and dried to obtain 41.8 g of the product.

MS (ESI$^+$): (M+H)$^+$ 242

HPLC: RT=0.28 min, Method D

Intermediate 21.1

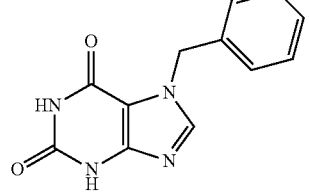

21.1

To a mixture of intermediate 20.1 (1.41 g, 5.86 mmol) in AcOH (40 ml) NaNO$_2$ (404 mg, 5.86 mmol) in H$_2$O (5 mL) was added dropwise at 50° C. and the mixture was stirred 3 h at 50° C. Additional NaNO2 (404 mg, 5.86 mmol) in H2O (5 mL) was added and the mixture was stirred overnight at 70° C. The mixture was cooled, basified with NaHCO$_3$ solution and extracted with DCM. The combined organic layers were dried and concentrated in vacuo. The crude product was purified by chromatography and freeze dried to obtain 1.13 g of the product.

MS (ESI$^+$): (M+H)$^+$ 242

HPLC: RT=0.32 min, Method A

Intermediate 22.1

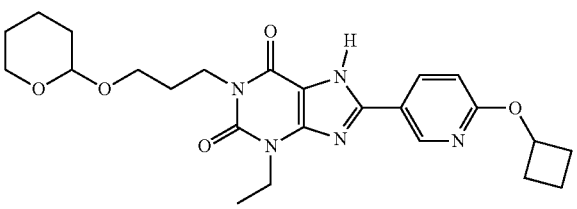

22.1

To a mixture of intermediate 12.5 (220 mg, 0.367 mmol) in THF (3.03 mL, 37.8 mmol) tetrabutylammonium fluoride (1 mol/L, 651 mg, 0.734 mmol) was added and the mixture was stirred overnight at 80° C. The mixture was cooled and used without further purification.

MS (ESI⁺): (M+H)⁺ 386
HPLC: RT=0.62 min, Method D

Intermediate 23.1

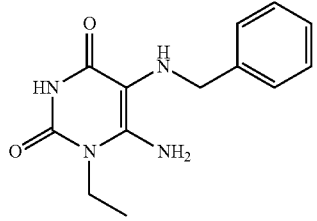

23.1

A mixture of intermediate 4.10 (0.89 g, 1.72 mmol), raney nickel (60 mg) and NaOH (1 N, 60 mL, 1.5 mol) was hydrogenated at rt and 50 psi of H₂ for 2 d. The mixture was filtered and acidified with HCl. The obtained precipitate was filtered, washed with water and dried to obtain 62.0 mg of the product.

MS (ESI⁺): (M+H)⁺ 261/262
HPLC: RT=0.34 min, Method D

Intermediate 24.1

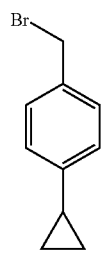

24.1

To a mixture of (4-cyclopropylphenyl)methanol (646 mg, 4.36 mmol) in DCM (5 mL) tribromophosphane (286.8 µL, 3.05 mmol) and THF (1 mL) were added and the mixture was stirred 30 min at rt. Additional tribromophosphane was added and the mixture was basified with saturated NaHCO₃ solution under ice cooling and extracted with DCM. The combined organic layers were dried and concentrated in vacuo to obtain 744 mg of the product.

HPLC: RT=0.69 min, Method F

Intermediate 24.2

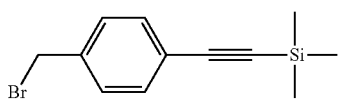

24.2

To a mixture of {4-[2-(trimethylsilyl)ethynyl]phenyl}methanol (772.4 mg, 3.78 mmol) in chloroform (3 mL) tribromophosphane (355.3 µL, 2.88 mmol) was added under ice cooling. The mixture was stirred overnight at rt. H₂O was added and extracted with DCM. The combined organic layers were dried and concentrated in vacuo. The crude product was purified by chromatography to obtain 150.0 mg of the product.

HPLC: RT=1.20 min, Method F

Intermediate 25.1

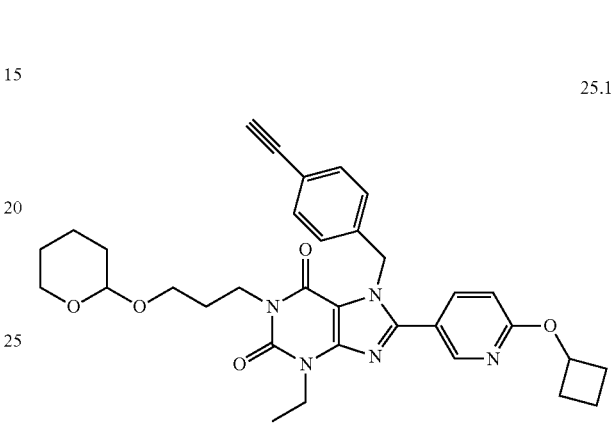

25.1

To a mixture of intermediate 5.29 (13 mg, 0.02 mmol) in MeOH (1 mL) and THF (1 mL) K₂CO₃ (5.5 mg) was added and the mixture was stirred 2 h at rt and used without further purification in the next step.

MS (ESI⁺): (M+H)⁺ 584
HPLC: RT=0.81 min, Method A

Intermediate 26.1

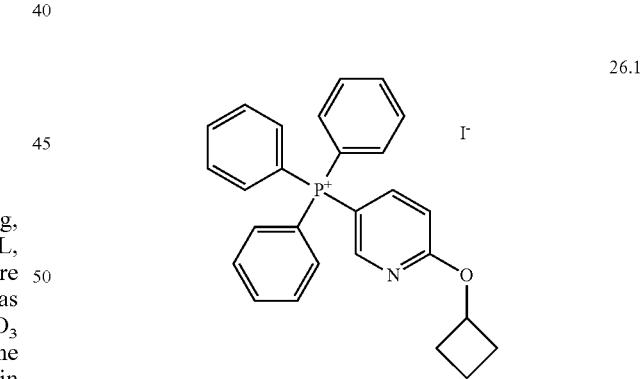

26.1

The reaction was performed under argon atmosphere.

A mixture of intermediate 9.6 (1.375 g, 5.00 mmol), tris(dibenzylideneacetone)-dipalladium(0) (45.8 mg, 0.05 mmol) and triphenylphosphane (1.31 g, 5.00 mmol) in xylol (3.37 mL, 28.5 mmol) was stirred 4.5 h at reflux. The mixture was cooled, EtOAc (100 mL) was added and heated to reflux. The mixture was cooled again and the obtained precipitate was filtered, washed with EtOAc and dried to obtain 2.20 g of the product.

MS (ESI⁺): (M+H)⁺ 410
HPLC: RT=0.58 min, Method A

Intermediate 27.1

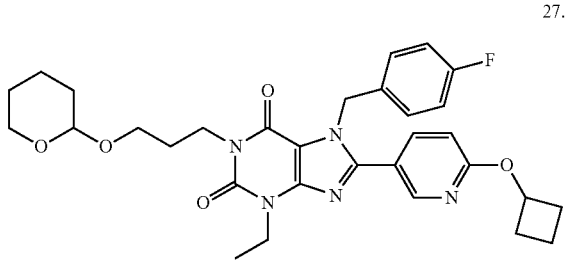

The reaction was performed under argon atmosphere.

To a mixture of intermediate 26.1 (633 mg, 0.88 mmol) and Pd(OAc)$_2$ (40 mg, 0.18 mmol) in DMF (2.5 mL) was added a solution of intermediate 6.9 (450 mg, 0.88 mmol) and K$_2$CO$_3$ (366 mg, 2.65 mmol) in DMF (3 mL) and the mixture was stirred 3 d at 120° C. The mixture was cooled, filtered over a celite pad, washed with DCM/MeOH (95/5), concentrated in vacuo and purified by chromatography to obtain 27.0 mg of the product.

MS (ESI$^+$): (M+H)$^+$ 578

HPLC: RT=0.87 min, Method D

EXAMPLES

Example 1

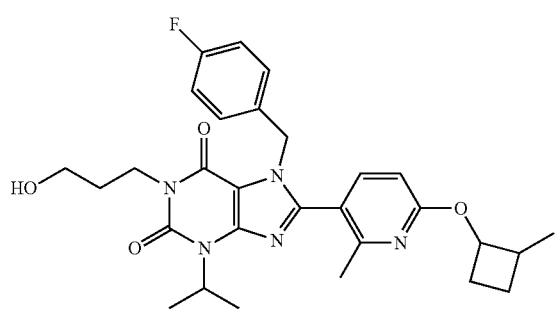

To a mixture of intermediate 7.1 (54.0 mg, 0.09 mmol) in MeOH (1.0 mL) and THF (1.0 mL) toluene-4-sulfonic acid hydrate (20.7 mg, 0.11 mmol) was added. The mixture was stirred 1 h at rt. The mixture was concentrated in vacuo and purified by chromatography to obtain 29.5 mg of the product.

MS (ESI$^+$): (M+H)$^+$ 536

HPLC: RT=0.84 min, Method F

Example 2

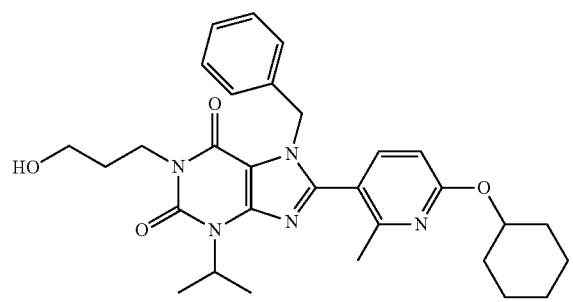

To a mixture of intermediate 7.2 (39.0 mg, 0.06 mmol) in MeOH (2.0 mL) toluene-4-sulfonic acid hydrate (0.06 g, 0.32 mmol) was added. The mixture was stirred 1 h at rt. The mixture was purified by chromatography to obtain 23.0 mg of the product.

MS (ESI$^+$): (M+H)$^+$ 533

HPLC: RT=0.88 min, Method G

1H NMR (DMSO-d6) δ 7.64 (d, J=8.4 Hz, 1H), 7.22-7.24 (m, 3H), 6.87-6.90 (m, 2H), 6.68 (d, J=8.4 Hz, 1H), 5.41 (s, 2H), 5.01-5.15 (m, 2H), 4.42 (t, J=5.3 Hz, 1H), 3.94-3.97 (m, 2H), 3.43-3.48 (m, 2H), 2.05 (s, 3H), 1.91-1.99 (m, 2H), 1.69-1.75 (m, 4H), 1.24-1.56 (m, 12H).

Example 3

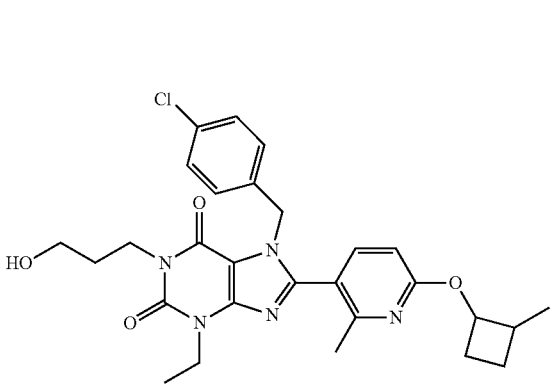

Example 3 was prepared in an analogous manner to example 1 using intermediate 7.3.

MS (ESI$^+$): (M+H)$^+$ 539/541 (Cl isotope pattern)

RT=1.44 min, Method C

Example 4

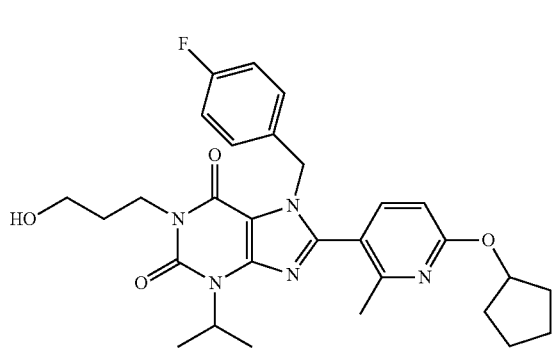

Example 4 was prepared in an analogous manner to example 1 using intermediate 7.4.
MS (ESI+): (M+H)+ 536
RT=0.83 min, Method F
1H NMR (DMSO-d6) δ 7.63 (d, J=8.5 Hz, 1H), 7.04-7.09 (m, 2H), 6.93-6.95 (m, 2H), 6.69 (d, J=8.5 Hz, 1H), 5.38-5.41 (m, 3H), 5.06-5.15 (m, 1H), 4.42 (t, J=5.3 Hz, 1H), 3.94-3.97 (m, 2H), 3.42-3.48 (m, 2H), 2.07 (s, 3H), 1.91-2.00 (m, 2H), 1.57-1.76 (m, 8H), 1.51 (d, J=6.8 Hz, 6H).

Example 5

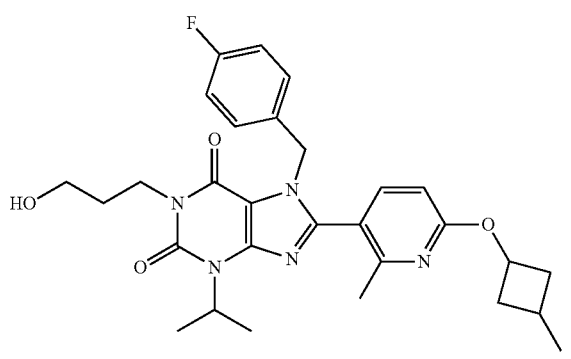

Example 5 was prepared in an analogous manner to example 1 using intermediate 7.5.
MS (ESI+): (M+H)+ 536
RT=0.83 min, Method F Example 6

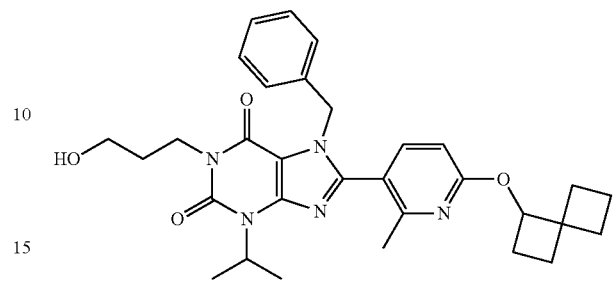

Example 6 was prepared in an analogous manner to example 1 using intermediate 7.6.
MS (ESI+): (M+H)+ 545
RT=0.59 min, Method E Example 7

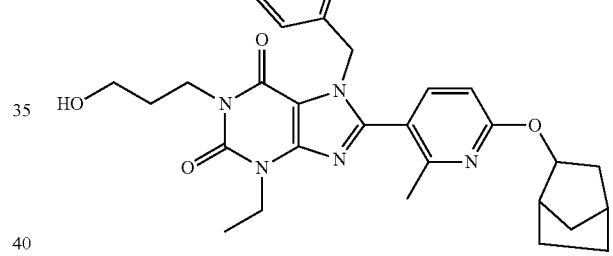

Example 7 was prepared in an analogous manner to example 1 using intermediate 7.7.
MS (ESI+): (M+H)+ 548
RT=0.84 min, Method G Example 8

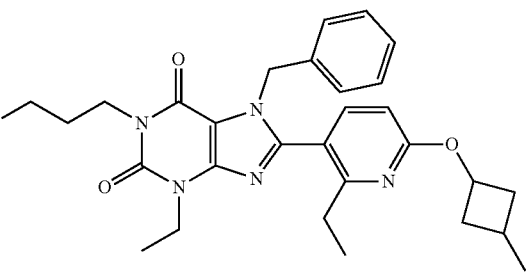

Example 7 was prepared in an analogous manner to example 2 using intermediate 12.1.
MS (ESI+): (M+H)+ 505
RT=0.8 min, Method G

Example 9

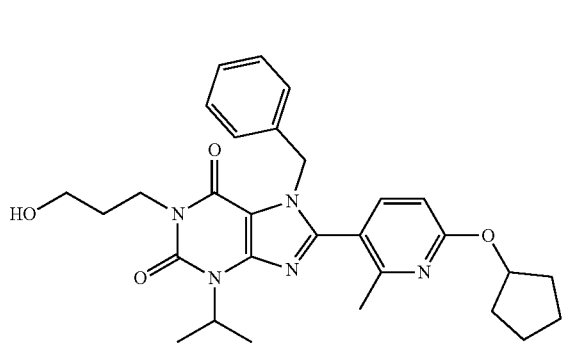

Example 9 was prepared in an analogous manner to example 1 using intermediate 7.8.

MS (ESI+): (M+H)+ 518

RT=0.85 min, Method D

1H NMR (DMSO-d6) δ 7.64 (d, J=8.5 Hz, 1H), 7.22-7.24 (m, 3H), 6.86-6.89 (m, 2H), 6.68 (d, J=8.5 Hz, 1H), 5.38-5.41 (m, 3H), 5.06-5.15 (m, 1H), 4.42 (t, J=5.3 Hz, 1H), 3.94-3.97 (m, 2H), 3.42-3.48 (m, 2H), 2.04 (s, 3H), 1.91-2.00 (m, 2H), 1.57-1.76 (m, 8H), 1.51 (d, J=7.0 Hz, 6H).

Example 10

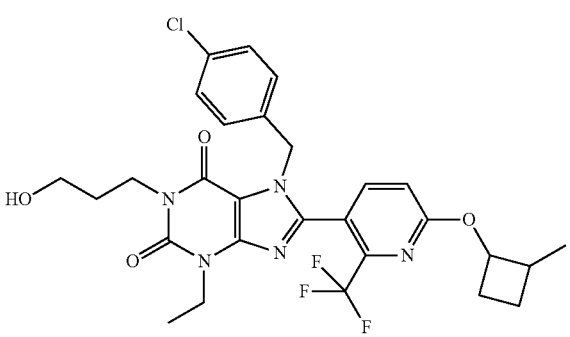

Example 10 was prepared in an analogous manner to example 1 using intermediate 7.9.

MS (ESI+): (M+H)+ 593/595 (Cl isotope pattern)

RT=1.47 min, Method C

Example 11

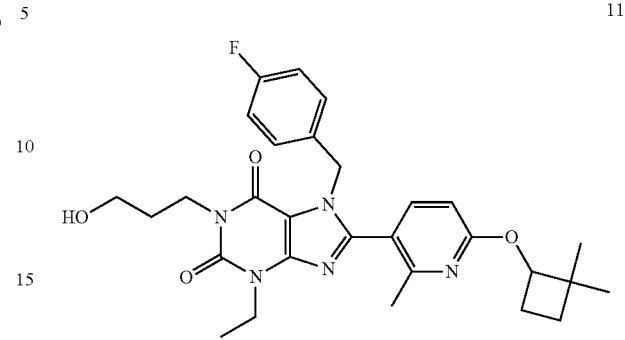

Example 11 was prepared in an analogous manner to example 2 using intermediate 7.11.

MS (ESI+): (M+H)+ 537

RT=0.84 min, Method D

Example 12

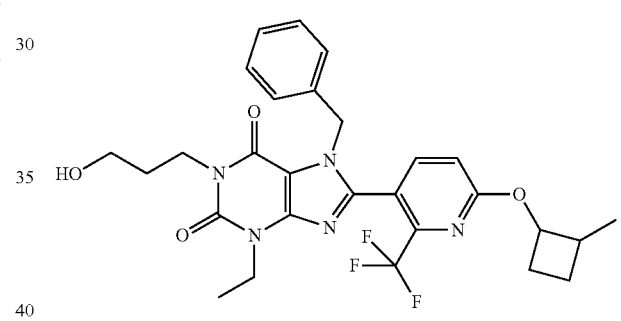

Example 12 was prepared in an analogous manner to example 1 using intermediate 7.12.

MS (ESI+): (M+H)+ 559

RT=1.41 min, Method C

Example 13

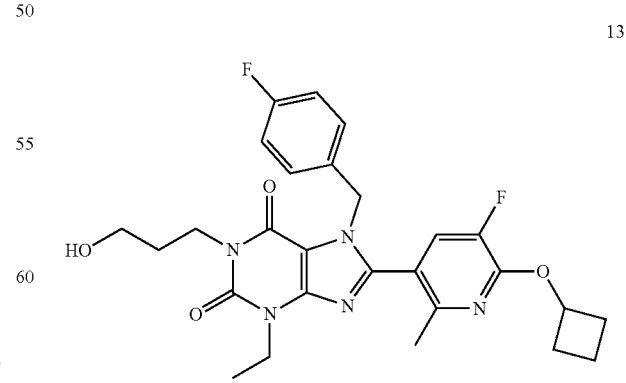

To a mixture of intermediate 15.1 (35.0 mg, 0.06 mmol) in MeOH (2.0 mL) toluene-4-sulfonic acid hydrate (0.055 g, 0.29 mmol) was added. The mixture was stirred 1 h at rt. The mixture was purified by chromatography to obtain 27.0 mg of the product.

MS (ESI⁺): (M+H)⁺ 527

HPLC: RT=0.78 min, Method G

Example 14

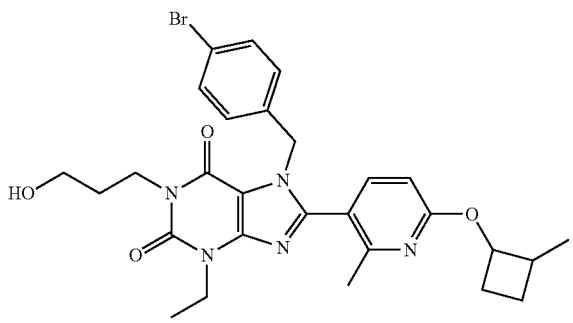

To a mixture of intermediate 7.14 (97 mg, 0.146 mmol) in MeOH (1.0 mL) and THF (1.0 mL) toluene-4-sulfonic acid hydrate (35 mg, 0.182 mmol) was added. The mixture was stirred 1.5 h at rt. The mixture was concentrated in vacuo and purified by chromatography to obtain 42.2 mg of the product.

MS (ESI⁺): (M+H)⁺ 583/585 (Br isotope pattern)

HPLC: RT=0.86 min, Method D

Example 15

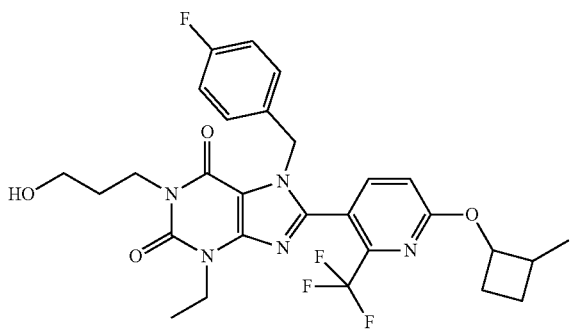

To a mixture of intermediate 7.15 (70 mg, 0.11 mmol) in MeOH (1.0 mL) and THF (1.0 mL) toluene-4-sulfonic acid hydrate (25 mg, 0.13 mmol) was added. The mixture was stirred 4 h at rt. The mixture was concentrated in vacuo and purified by chromatography to obtain 45.4 mg of the product.

MS (ESI⁺): (M+H)⁺ 577

HPLC: RT=1.42 min, Method C

Example 16

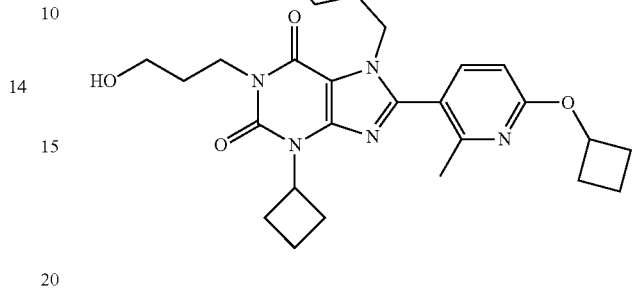

To a mixture of intermediate 7.17 (170 mg, 0.28 mmol) in MeOH (2.0 mL) toluene-4-sulfonic acid hydrate (0.27 g, 1.42 mmol) was added. The mixture was stirred 1 h at rt. The mixture was purified by chromatography and freeze dried to obtain 123 mg of the product.

MS (ESI⁺): (M+H)⁺ 517

RT=0.85 min, Method G

Example 17

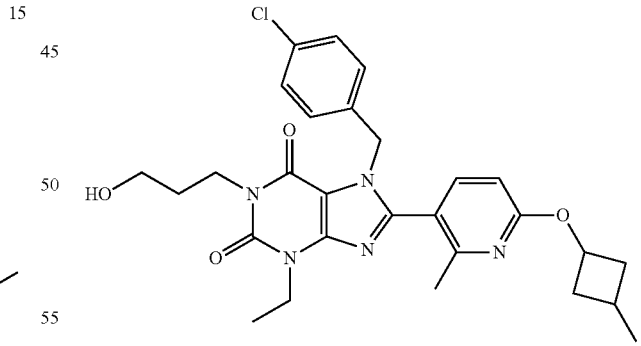

Example 17 was prepared in an analogous manner to example 15 using intermediate 7.18.

MS (ESI⁺): (M+H)⁺ 539/541 (Cl isotope pattern)

RT=0.84 min, Method C

Example 18

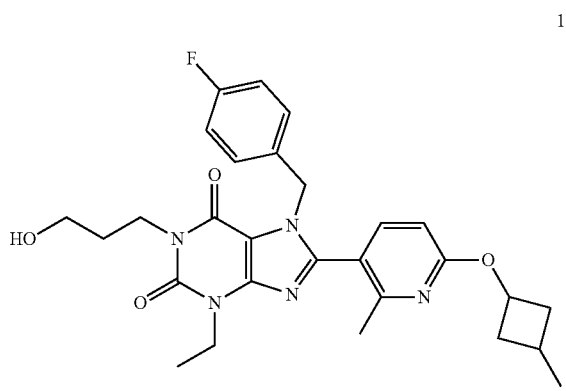

Example 18 was prepared in an analogous manner to example 16 using intermediate 7.20.

MS (ESI$^+$): (M+H)$^+$ 523

RT=0.8 min, Method D

Example 19

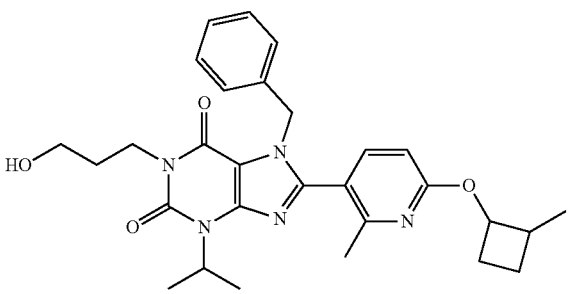

To a mixture of intermediate 7.21 (98 mg, 0.16 mmol) in THF (1.0 mL) toluene-4-sulfonic acid hydrate (0.155 g, 0.81 mmol) was added. The mixture was stirred 1 h at rt.

The mixture was purified by chromatography and freeze dried to obtain 55.0 mg of the product.

MS (ESI$^+$): (M+H)$^+$ 519

HPLC: RT=1.48 min, Method C

Example 20

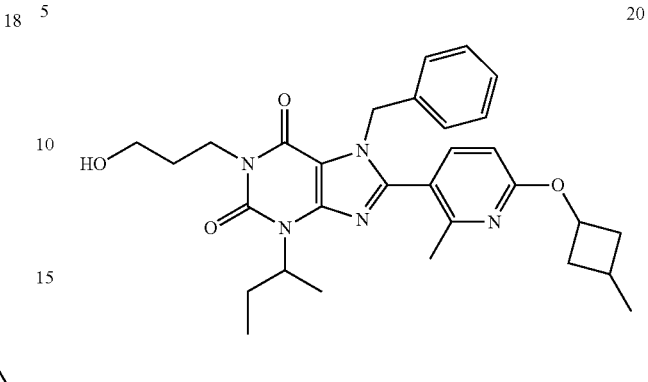

To a mixture of intermediate 7.22 (crude, 259 mg, 0.42 mmol) in ACN (1 mL) toluene-4-sulfonic acid hydrate (240 mg, 1.26 mmol) and MeOH (5 mL, 0.125 mol) were added and the mixture was stirred 30 min at rt. The mixture was purified by chromatography to obtain 170 mg of the product.

MS (ESI$^+$): (M+H)$^+$ 533

RT=0.88 min, Method G

Example 21

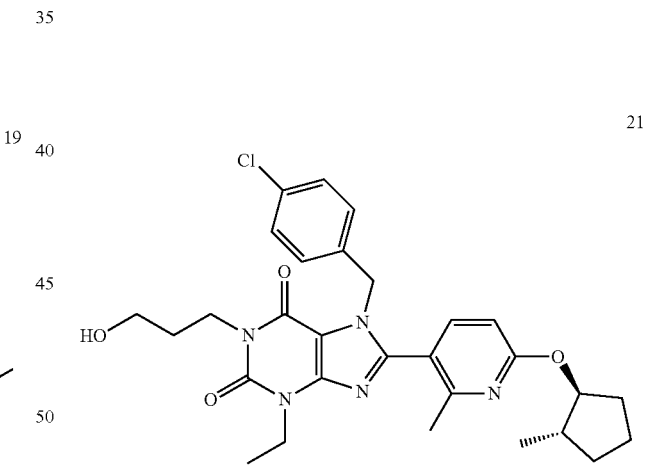

To a mixture of intermediate 7.23 (13 mg, 0.02 mmol) in MeOH (0.5 mL) and THF (0.5 mL) toluene-4-sulfonic acid hydrate (5 mg, 0.03 mmol) was added. The mixture was stirred 1.5 h at rt. The mixture was concentrated in vacuo and purified by chromatography to obtain 9.4 mg of the product as a racemic mixture.

MS (ESI$^+$): (M+H)$^+$ 553/555 (Cl isotope pattern)

RT=0.88 min, Method D

Example 22

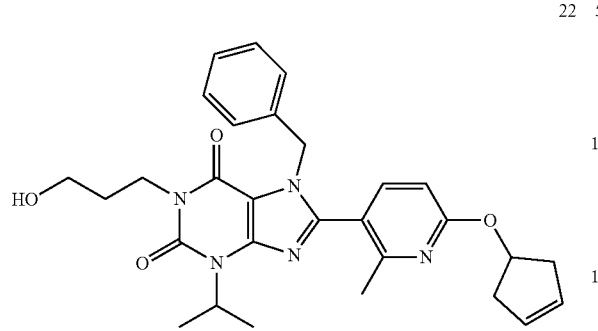

Example 22 was prepared in an analogous manner to example 16 using intermediate 7.24.

MS (ESI$^+$): (M+H)$^+$ 517

RT=0.41 min, Method E

Example 23

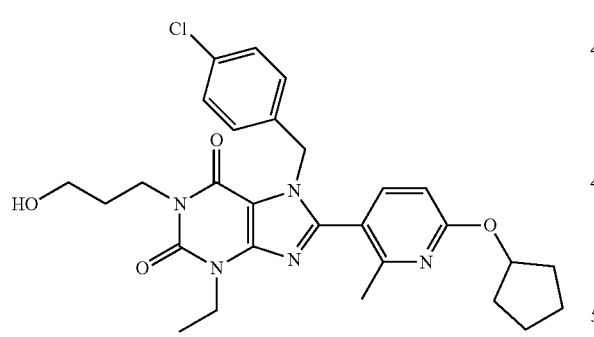

To a mixture of intermediate 7.25 (26 mg, 0.04 mmol) in MeOH (1 mL) and THF (1 mL) toluene-4-sulfonic acid hydrate (10 mg, 0.05 mmol) was added. The mixture was stirred 0.5 h at rt. The mixture was concentrated in vacuo and purified by chromatography to obtain 14.5 mg of the product.

MS (ESI$^+$): (M+H)$^+$ 539/541 (Cl isotope pattern)

RT=1.42 min, Method C

Example 24

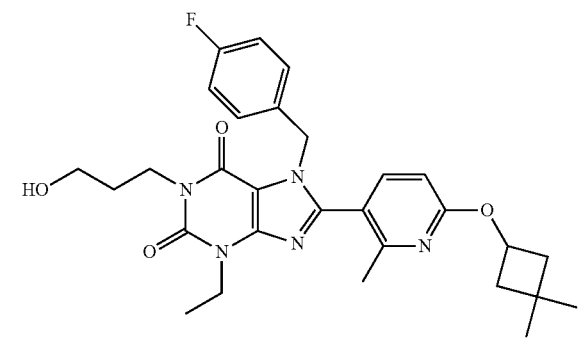

Example 24 was prepared in an analogous manner to example 16 using intermediate 7.26.

MS (ESI$^+$): (M+H)$^+$ 537

RT=0.82 min, Method D

Example 25

Example 25 was prepared in an analogous manner to example 16 using intermediate 7.27.

MS (ESI$^+$): (M+H)$^+$ 559

RT=1.08 min, Method F

1H NMR (DMSO-d6) δ 7.72 (d, J=8.5 Hz, 1H), 7.05-7.09 (m, 2H), 6.92-6.96 (m, 2H), 6.81 (d, J=8.5 Hz, 1H), 5.39 (s, 2H), 5.05-5.20 (m, 2H), 4.42 (t, J=5.3 Hz, 1H), 3.94-3.98 (m, 2H), 3.43-3.48 (m, 2H), 3.11-3.21 (m, 2H), 2.66-2.80 (m, 2H), 2.06 (s, 3H), 1.69-1.76 (m, 2H), 1.51 (d, J=6.9 Hz, 6H).

Example 26

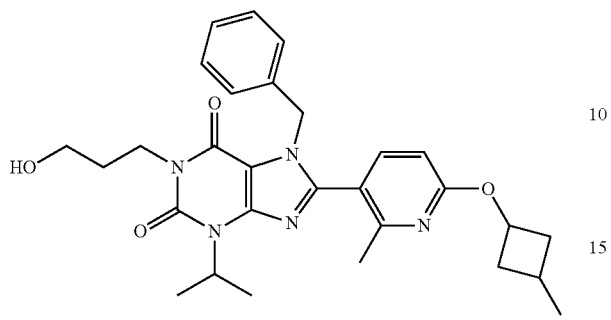

Example 26 was prepared in an analogous manner to example 16 using intermediate 12.2.
MS (ESI⁺): (M+H)⁺ 519
RT=1.13 min, Method F Example 27

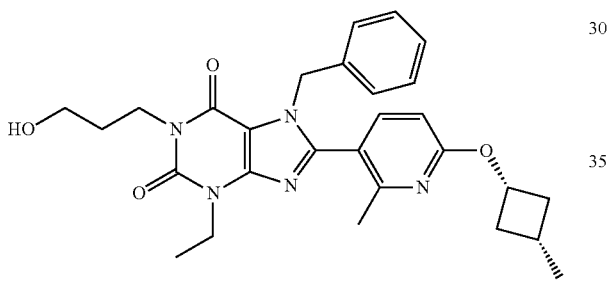

To a mixture of intermediate 12.3 (155 mg, 0.26 mmol) in MeOH (1.5 mL) toluene-4-sulfonic acid hydrate (100 mg, 0.53 mmol) was added. The mixture was stirred 3 h at rt. The mixture was concentrated in vacuo and purified by chromatography.Cis/trans isomers were separated by SFC (see example 28 for other isomer).
MS (ESI⁺): (M+H)⁺ 505
RT=4.428 min, Method J Example 28

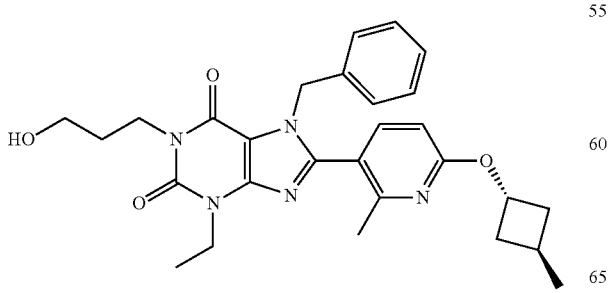

To a mixture of intermediate 12.3 (155 mg, 0.26 mmol) in MeOH (1.5 mL) toluene-4-sulfonic acid hydrate (100 mg, 0.53 mmol) was added. The mixture was stirred 3 h at rt. The mixture was concentrated in vacuo and purified by chromatography. Cis/trans isomers were separated by SFC (see example 27 for other isomer).
MS (ESI⁺): (M+H)⁺ 505
RT=5.005 min, Method J Example 29

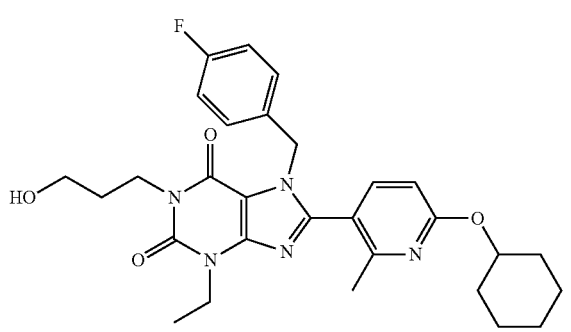

To a mixture of intermediate 7.28 (55 mg, 0.09 mmol) in MeOH (1.0 mL) and THF (1.0 mL) toluene-4-sulfonic acid hydrate (21 mg, 0.11 mmol) was added. The mixture was stirred 1 h at rt. The mixture was concentrated in vacuo and purified by chromatography to obtain 34.3 mg of the product.
MS (ESI⁺): (M+H)⁺ 537
HPLC: RT=0.82 min, Method D Example 30

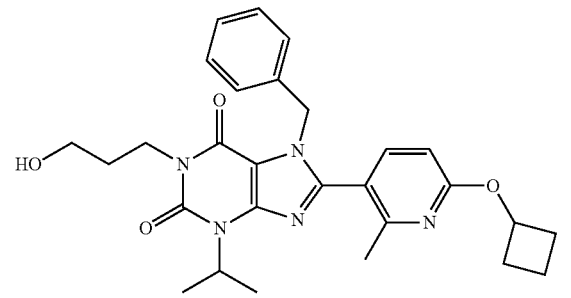

To a mixture of intermediate 12.4 (121 mg, 0.19 mmol) in MeOH (3.0 mL) toluene-4-sulfonic acid hydrate (182 mg, 0.96 mmol) was added. The mixture was stirred 1 h at rt. The mixture was concentrated in vacuo, purified by chromatography and freeze dried to obtain 95.0 mg of the product.
MS (ESI⁺): (M+H)⁺ 505
HPLC: RT=1.08 min, Method F
1H NMR (DMSO-d6) δ 7.66 (d, J=8.5 Hz, 1H), 7.21-7.25 (m, 3H), 6.86-6.89 (m, 2H), 6.70 (d, J=8.5 Hz, 1H), 5.41 (s, 2H), 5.05-5.19 (m, 2H), 4.42 (t, J=5.3 Hz, 1H), 3.94-3.97 (m, 2H), 3.42-3.48 (m, 2H), 2.36-2.45 (m, 2H), 2.01-2.12 (m, 5H), 1.61-1.83 (m, 4H), 1.51 (d, J=7.0 Hz, 6H).

Example 31

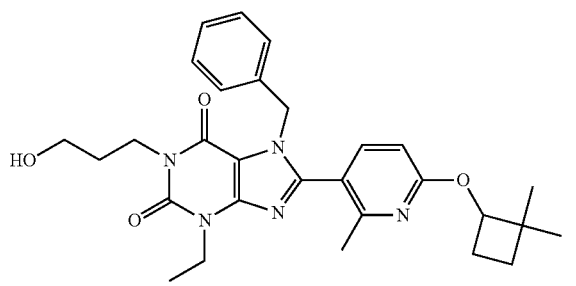

Example 31 was prepared in an analogous manner to example 30 using intermediate 7.29.
MS (ESI⁺): (M+H)⁺ 519
RT=0.85 min, Method D

Example 32

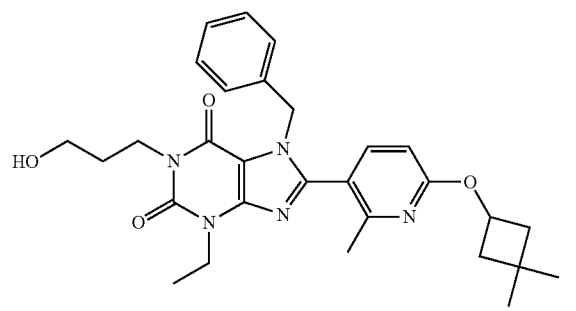

Example 32 was prepared in an analogous manner to example 30 using intermediate 7.30.
MS (ESI⁺): (M+H)⁺ 519
RT=0.83 min, Method D

Example 33

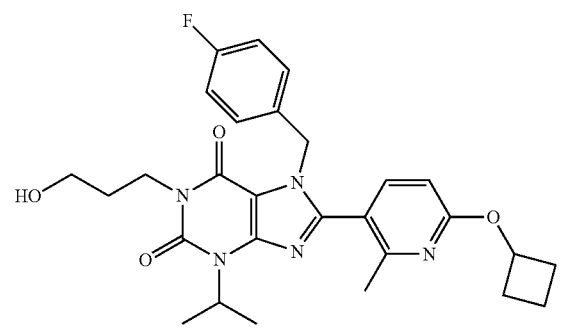

Example 33 was prepared in an analogous manner to example 29 using intermediate 7.31.
MS (ESI⁺): (M+H)⁺ 523
RT=0.73 min, Method D
1H NMR (DMSO-d6) δ 7.65 (d, J=8.5 Hz, 1H), 7.04-7.09 (m, 2H), 6.92-6.95 (m, 2H), 6.71 (d, J=8.4 Hz, 1H), 5.39 (s, 2H), 5.05-5.19 (m, 2H), 4.41-4.43 (m, 1H), 3.94-3.97 (m, 2H), 3.42-3.48 (m, 2H), 2.36-2.45 (m, 2H), 2.01-2.12 (m, 5H), 1.61-1.83 (m, 4H), 1.51 (d, J=7.0 Hz, 6H).

Example 34

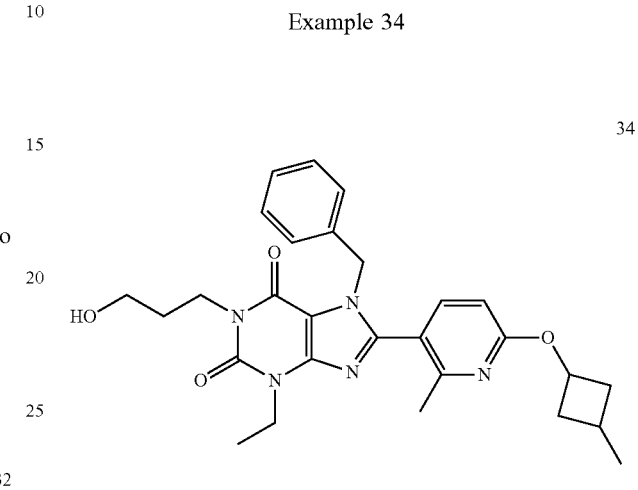

Example 34 was prepared in an analogous manner to example 29 using intermediate 7.32.
MS (ESI⁺): (M+H)⁺ 505
RT=0.79 min, Method D

Example 35

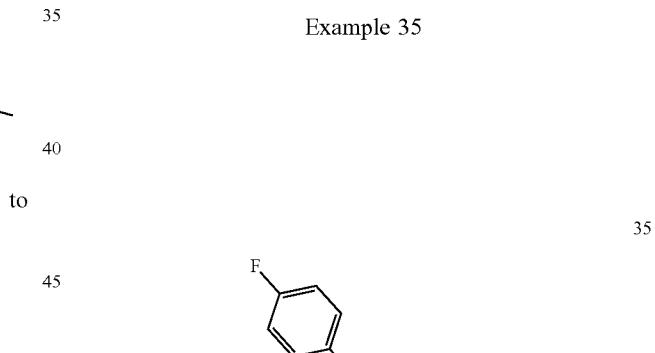

Example 35 was prepared in an analogous manner to example 30 using intermediate 7.34.
MS (ESI⁺): (M+H)⁺ 605
RT=0.72 min, Method D

Example 36

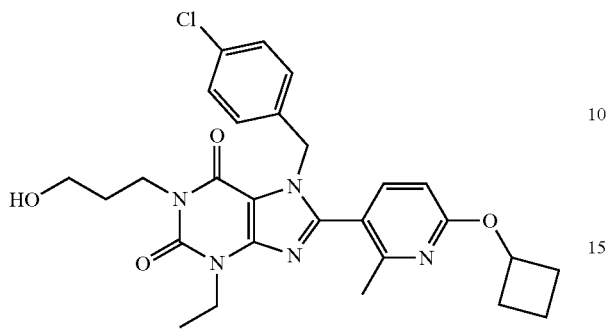

Example 36 was prepared in an analogous manner to example 29 using intermediate 7.35.
MS (ESI⁺): (M+H)⁺ 525/527 (Cl isotope pattern)
RT=1.35 min, Method C

Example 37

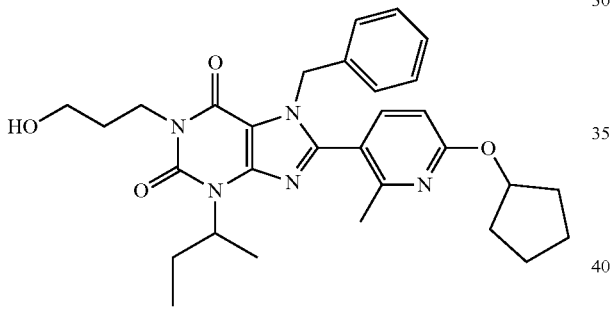

Example 37 was prepared in an analogous manner to example 30 using intermediate 7.36.
MS (ESI⁺): (M+H)⁺ 533
RT=0.88 min, Method G

Example 38

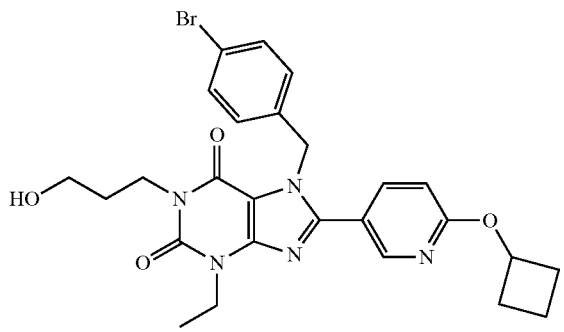

To a mixture of intermediate 22.1 (40 mg, 0.085 mmol) in THF (704 µL) and DMSO (697 µL) DIPEA (16.1 µL, 0.094 mmol) and 1-bromo-4-(bromomethyl)benzene (32 mg, 0.128 mmol) were added. The mixture was stirred 1.5 h at 50° C. Additional DIPEA was added and the mixture was stirred 45 min at 90° C. Then additional 1-bromo-4-(bromomethyl)benzene was added and the mixture was stirred 1 h at 90° C. The mixture was cooled and purified by chromatography to obtain 8.0 mg of the product.

MS (ESI⁺): (M+H)⁺ 555/557 (Br isotope pattern)
HPLC: RT=0.78 min, Method D

Example 39

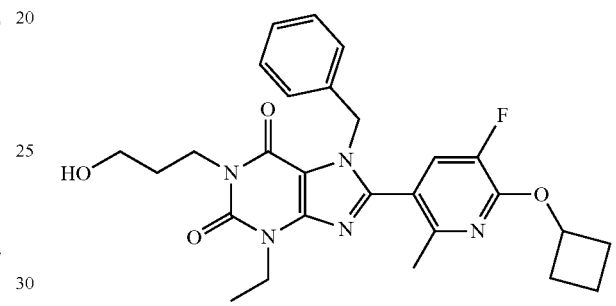

Example 39 was prepared in an analogous manner to example 30 using intermediate 15.3.
MS (ESI⁺): (M+H)⁺ 509
RT=0.77 min, Method G

Example 40

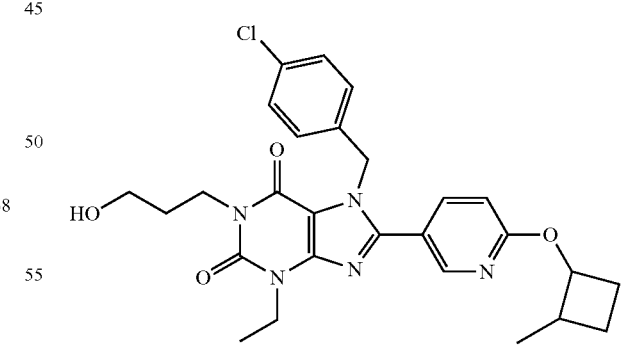

To a mixture of intermediate 7.37 (62 mg, 0.102 mmol) in THF (1.0 mL) toluene-4-sulfonic acid hydrate (182 mg, 0.96 mmol) was added. The mixture was stirred 1 h at rt. The mixture was concentrated in vacuo, purified by chromatography and freeze dried to obtain 40.0 mg of the product.

MS (ESI⁺): (M+H)⁺ 526/528 (Cl isotope pattern)
HPLC: RT=1.4 min, Method C

Example 41

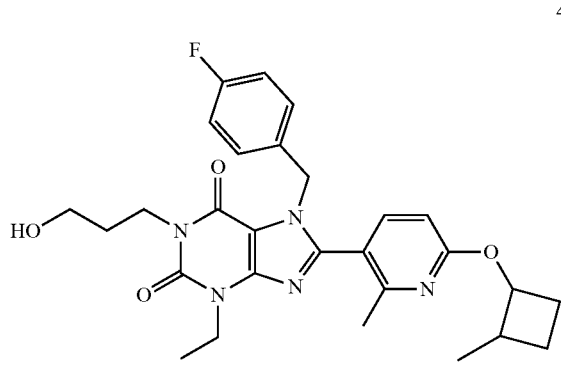

Example 41 was prepared in an analogous manner to example 40 using intermediate 7.38.

MS (ESI$^+$): (M+H)$^+$ 523

RT=1.37 min, Method C

Example 42

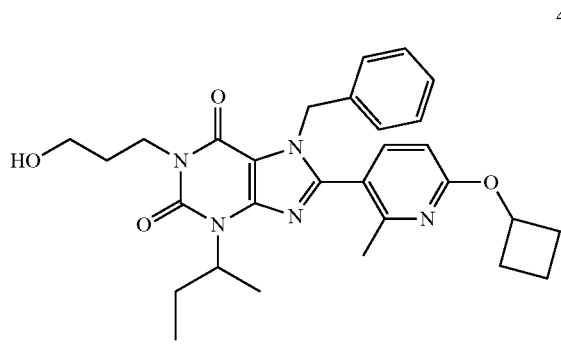

To a mixture of intermediate 7.39 (253 mg, 0.42 mmol) in ACN (1 ml), MeOH (5 ml) and toluene-4-sulfonic acid hydrate (240 mg, 1.26 mmol) were added and the mixture was stirred 30 min at rt. The mixture was purified by chromatography to obtain 181 mg of the product.

MS (ESI$^+$): (M+H)$^+$ 519

RT=0.84 min, Method G

Example 43

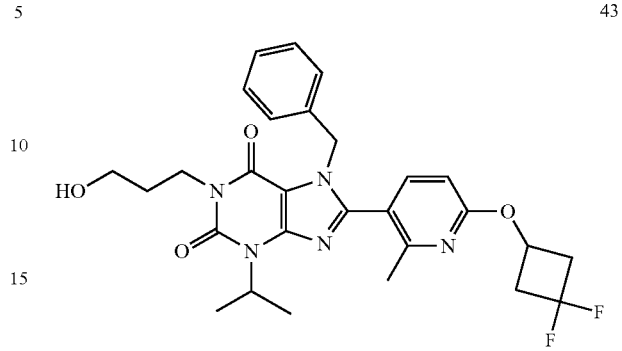

Example 43 was prepared in an analogous manner to example 30 using intermediate 7.40.

MS (ESI$^+$): (M+H)$^+$ 541

RT=1.07 min, Method F

1H NMR (DMSO-d6) δ 7.73 (d, J=8.5 Hz, 1H), 7.21-7.25 (m, 3H), 6.87-6.89 (m, 2H), 6.80 (d, J=8.2 Hz, 1H), 5.41 (s, 2H), 5.05-5.19 (m, 2H), 4.43 (t, J=5.0 Hz, 1H), 3.94-3.98 (m, 2H), 3.43-3.48 (m, 2H), 3.11-3.21 (m, 2H), 2.66-2.80 (m, 2H), 2.06 (s, 3H), 1.69-1.76 (m, 2H), 1.51 (d, J=6.9 Hz, 6H).

Example 44

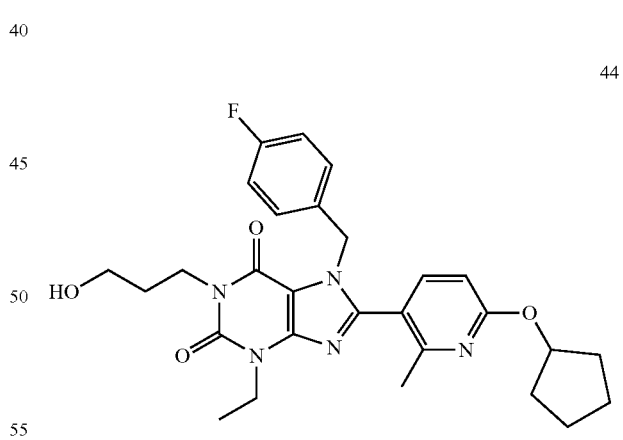

Example 44 was prepared in an analogous manner to example 30 using intermediate 7.41.

MS (ESI$^+$): (M+H)$^+$ 523

RT=0.79 min, Method D

Example 45

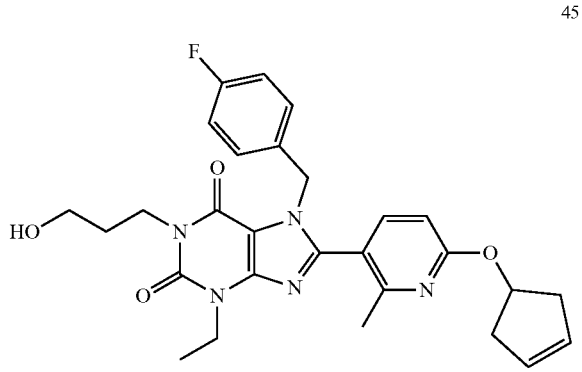 [SMILES: CCn1c(=O)n(CCCO)c(=O)c2c1nc(-c1ccc(OC3CC=CC3)nc1C)n2Cc1ccc(F)cc1]

Example 45 was prepared in an analogous manner to example 29 using intermediate 7.42.

MS (ESI$^+$): (M+H)$^+$ 521

RT=0.74 min, Method D

Example 46

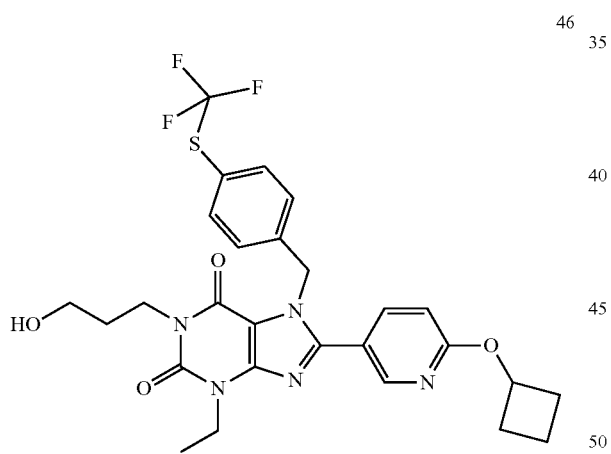

To a mixture of intermediate 22.1 (40 mg, 0.085 mmol) in THF (704 µL) and DMSO (697 µL) DIPEA (16.1 µL, 0.094 mmol) and 4-(trifluormethylthio)benzylchloride (29 mg, 0.128 mmol) were added. The mixture was stirred 1.5 h at 50° C. Additional DIPEA was added and the mixture was stirred 1.5 h at 90° C. Then additional 4-(trifluormethylthio)benzylchloride was added and the mixture was stirred 1 h at 90° C. The mixture was cooled and purified by chromatography to obtain 7.0 mg of the product.

MS (ESI$^+$): (M+H)$^+$ 577

HPLC: RT=0.83 min, Method D

Example 47

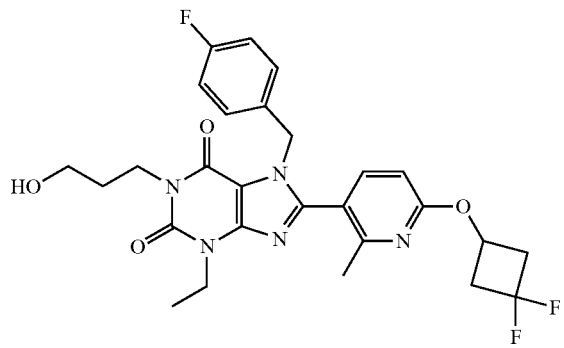

Example 47 was prepared in an analogous manner to example 30 using intermediate 7.43.

MS (ESI$^+$): (M+H)$^+$ 545

RT=0.67 min, Method D

Example 48

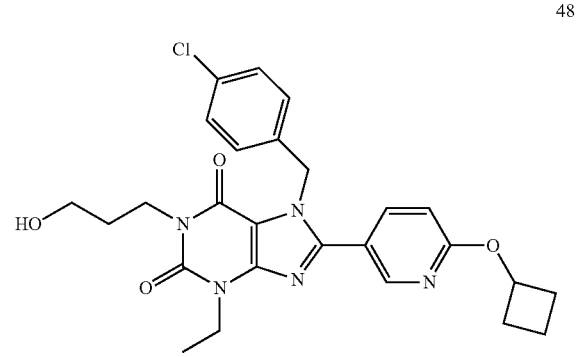 [SMILES: CCn1c(=O)n(CCCO)c(=O)c2c1nc(-c1ccc(OC3CCC3)nc1)n2Cc1ccc(Cl)cc1]

To the crude reaction mixture of intermediate 5.20 (29.7 mg, 0.05 mmol) toluene-4-sulfonic acid hydrate (28.5 mg, 0.15 mmol) and MeOH (0.5 mL) were added. The mixture was stirred overnight at rt. The mixture was purified by chromatography to obtain 18.3 mg of the product.

MS (ESI$^+$): (M+H)$^+$ 511/513 (Cl isotope pattern)

HPLC: RT=0.76 min, Method D

Example 49

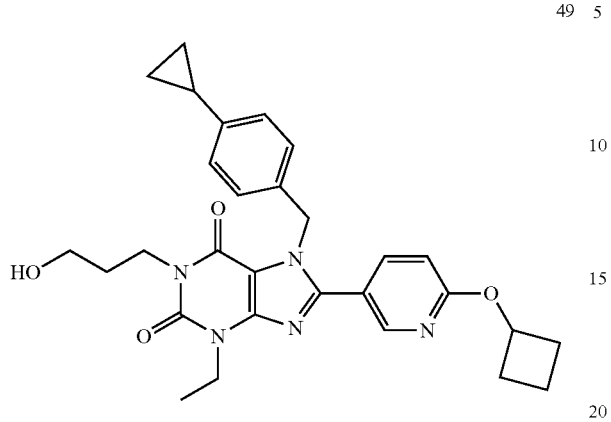

Example 49 was prepared in an analogous manner to example 29 using intermediate 7.45.

MS (ESI+): (M+H)+ 517

RT=1.11 min, Method F

Example 50

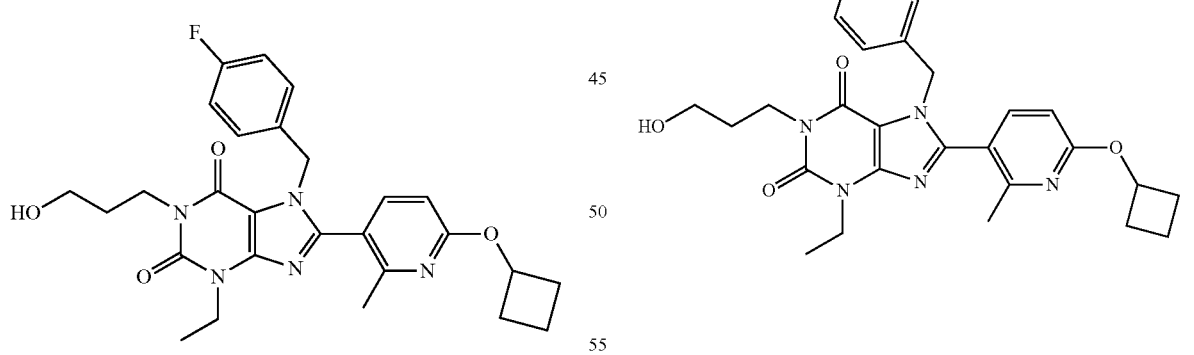

Example 50 was prepared in an analogous manner to example 30 using intermediate 7.47.

MS (ESI+): (M+H)+ 509

RT=0.75 min, Method D

Example 51

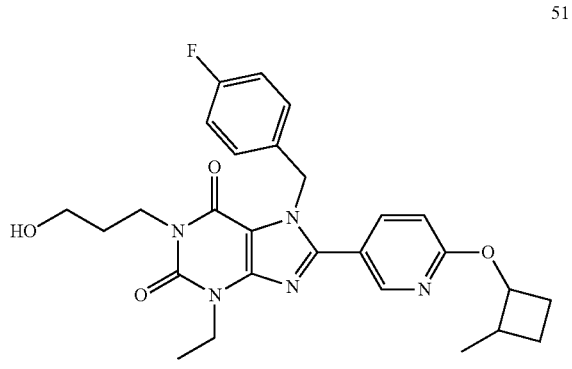 [SMILES: CCn1c(=O)n(CCCO)c(=O)c2c1nc(-c1ccc(OC3CCC3)nc1F)n2Cc1ccc(F)cc1]

Example 51 was prepared in an analogous manner to example 40 using intermediate 6.25.

MS (ESI+): (M+H)+ 509

RT=1.34 min, Method C

Example 52

To a mixture of intermediate 7.49 (88 mg, 0.153 mmol) in MeOH (1 mL) and THF (1 mL) toluene-4-sulfonic acid hydrate (36.5 mg, 0.192 mmol) was added and the mixture was stirred 1 h at rt. The mixture was purified by chromatography to obtain 69.1 mg of the product.

MS (ESI+): (M+H)+ 491

RT=0.74 min, Method D

Example 53

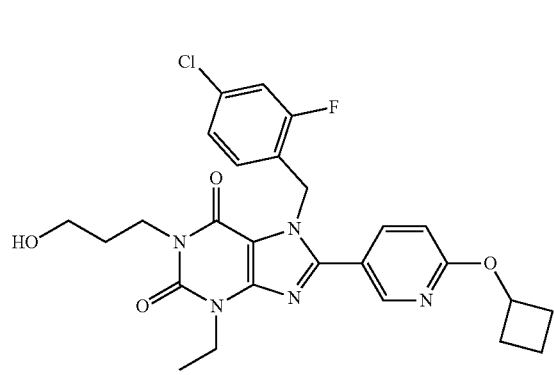

53

To the reaction mixture of intermediate 5.25 toluene-4-sulfonic acid hydrate (171.2 mg, 0.90 mmol) and MeOH (2 mL) were added. The mixture was stirred 1 h at rt. The mixture was purified by chromatography to obtain 41.0 mg of the product.

MS (ESI$^+$): (M+H)$^+$ 529/531 (CI isotope pattern)

HPLC: RT=0.78 min, Method D

Example 54

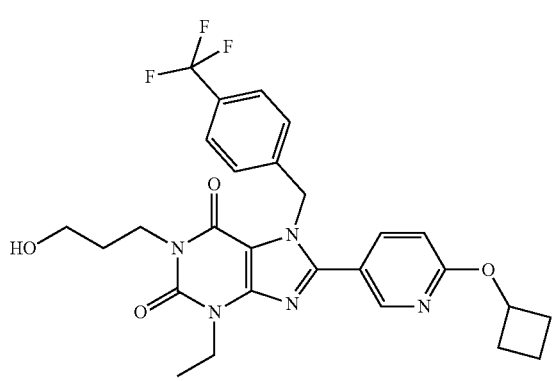

54

Example 54 was prepared in an analogous manner to example 53 using intermediate 5.26.

MS (ESI$^+$): (M+H)$^+$ 545

RT=0.79 min, Method D

Example 55

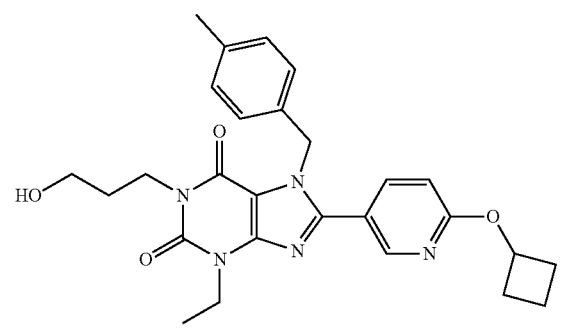

55

Example 55 was prepared in an analogous manner to example 53 using intermediate 5.27.

MS (ESI$^+$): (M+H)$^+$ 491

RT=0.77 min, Method D

Example 56

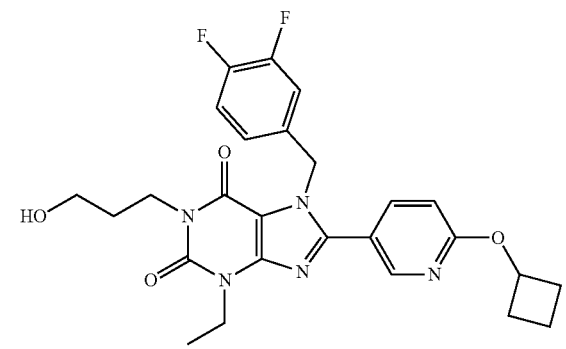

56

Example 56 was prepared in an analogous manner to example 53 using intermediate 5.28.

MS (ESI$^+$): (M+H)$^+$ 513

RT=0.74 min, Method D

Example 57

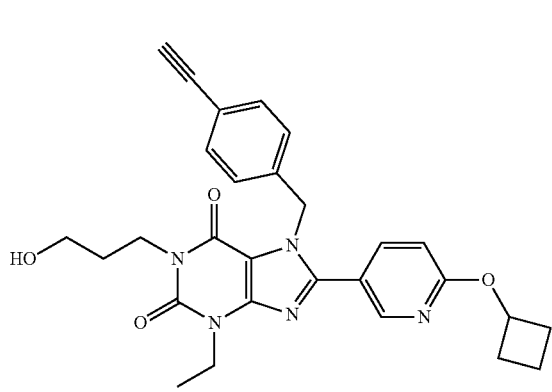

To the crude reaction mixture of intermediate 25.1 toluene-4-sulfonic acid hydrate (11.3 mg, 0.06 mmol) and MeOH (2 mL) were added. The mixture was stirred 1 h at rt. The mixture was purified by chromatography to obtain 5.8 mg of the product.
MS (ESI$^+$): (M+H)$^+$ 501
HPLC: RT=0.70 min, Method A

Example 58

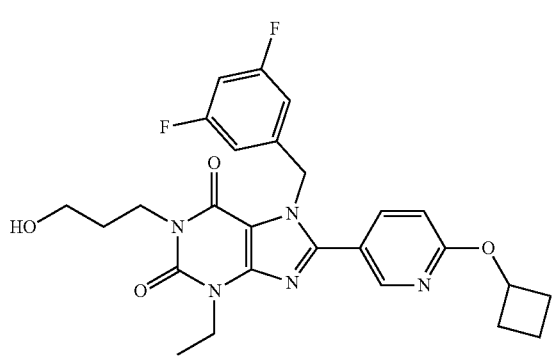

To a mixture of intermediate 22.1 (40 mg, 0.085 mmol) in THF (704 μL) and DMSO (697 μL) DIPEA (16.1 μL, 0.094 mmol) and 1-(bromomethyl)-3,5-difluorobenzene (26.5 mg, 0.128 mmol) were added. The mixture was stirred 1.5 h at 50° C. Additional DIPEA was added and the mixture was stirred 2 h at 90° C. Then additional 1-(bromomethyl)-3,5-difluorobenzene was added and the mixture was stirred 1 h at 90° C. The mixture was cooled and purified by chromatography to obtain 15.0 mg of the product.
MS (ESI$^+$): (M+H)$^+$ 513
HPLC: RT=0.74 min, Method D

Example 59

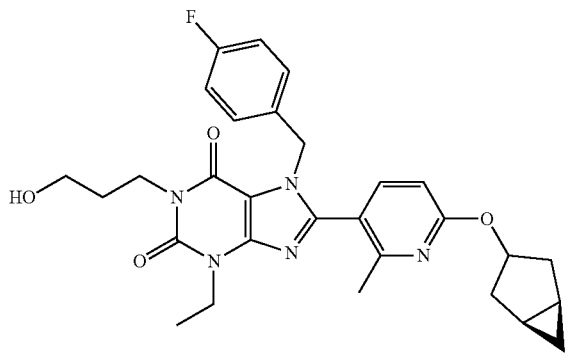

Example 59 was prepared in an analogous manner to example 53 using intermediate 7.50.
MS (ESI$^+$): (M+H)$^+$ 535
RT=1.09 min, Method F

Example 60

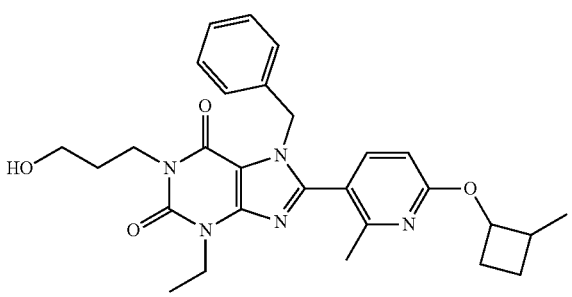

To a mixture of intermediate 7.51 (92 mg, 0.157 mmol) in MeOH (1 mL) and THF (1 mL) toluene-4-sulfonic acid hydrate (37.2 mg, 0.196 mmol) was added and the mixture was stirred 1.5 h at rt. The mixture was purified by chromatography to obtain 43.0 mg of the product.
MS (ESI$^+$): (M+H)$^+$ 505
RT=0.8 min, Method D

Example 61

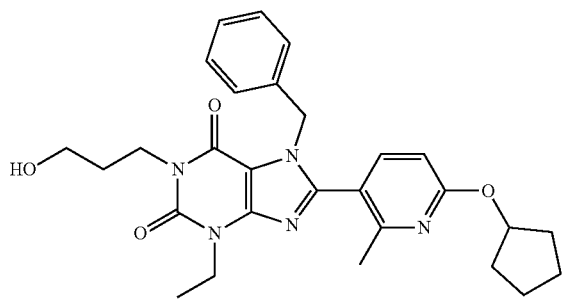

Example 61 was prepared in an analogous manner to example 54 using intermediate 7.52.
MS (ESI⁺): (M+H)⁺ 505
RT=0.78 min, Method D

Example 62

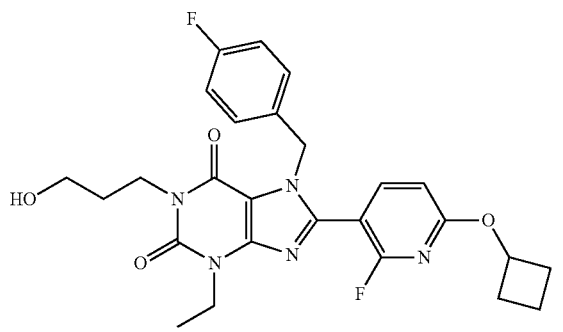

To a mixture of intermediate 12.6.1 (42 mg, 0.071 mmol) in MeOH (1 mL) and THF (1 mL) toluene-4-sulfonic acid hydrate (12.2 mg, 0.071 mmol) was added and the mixture was stirred 1 h at rt. The mixture was purified by chromatography to obtain 13.7 mg of the product.
MS (ESI⁺): (M+H)⁺ 513
RT=0.74 min, Method G

Example 63

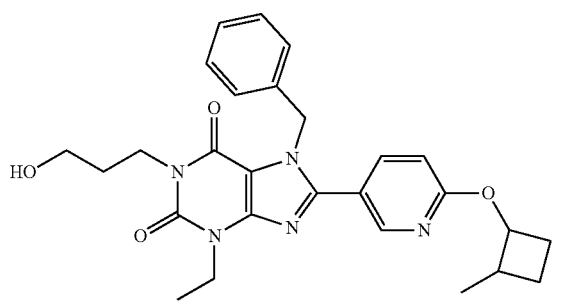

To a mixture of intermediate 7.53 (38 mg, 0.066 mmol) in THF (1 mL) toluene-4-sulfonic acid hydrate (63 mg, 0.331 mmol) was added and the mixture was stirred 1 h at rt. The mixture was purified by chromatography and freeze dried to obtain 27.0 mg of the product.
MS (ESI⁺): (M+H)⁺ 491
RT=1.33 min, Method C

Example 64

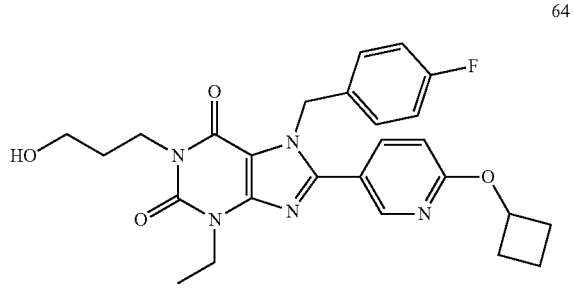 [SMILES: CCn1c(=O)n(CCCO)c(=O)c2c1nc(-c1ccc(OC3CCC3)nc1)n2Cc1ccc(F)cc1]

Example 64 was prepared in an analogous manner to example 53 using intermediate 27.1.
MS (ESI⁺): (M+H)⁺ 495
RT=0.73 min, Method D

The invention claimed is:
1. A compound of formula I:

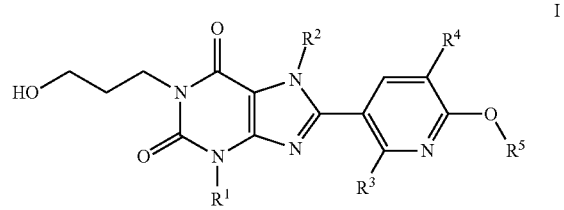

or a pharmaceutically acceptable salt thereof,
wherein:
  $R^1$ represents ethyl, isopropyl, isobutyl, or cyclobutyl;
  $R^2$ represents benzyl, 4-fluorobenzyl, 4-chlorobenzyl, 4-bromobenzyl, 4-methylbenzyl, 4-(trifluoromethyl)benzyl, 4-ethynylbenzyl, 4-cyclopropylbenzyl, 3,4-difluorobenzyl, 3,5-difluorobenzyl, 2-fluoro-4-chlorobenzyl, 3-fluoro-4-chlorobenzyl, 3-fluoro-4-methylbenzyl, 3-fluoro-4-(trifluoromethyl)benzyl, or 4-(trifluoromethylthio)benzyl;
  $R^3$ represents hydrogen, fluoro, or $C_1$-$C_3$ alkyl, wherein the $C_1$-$C_3$ alkyl is optionally substituted with one or more fluoro substituents;
  $R^4$ represents hydrogen or fluoro; and
  $R^5$ represents:

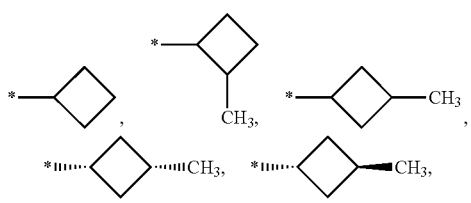

-continued

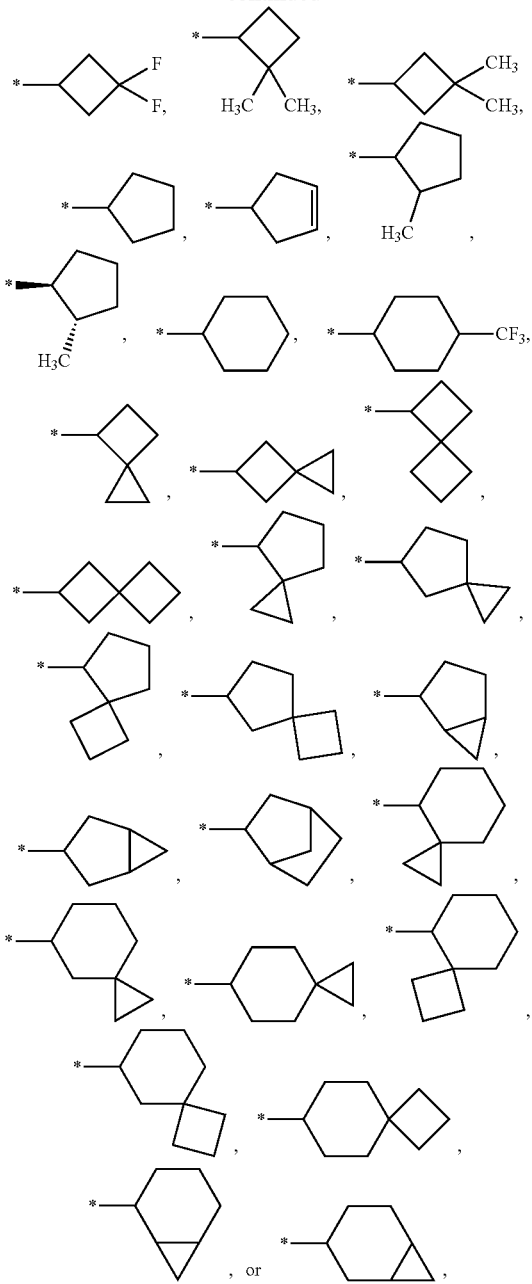

wherein each R⁵ is optionally substituted with one or more substituents independently selected from the group consisting of fluoro and $C_1$-$C_3$ alkyl;
wherein each $C_1$-$C_3$ alkyl substituent is independently substituted with one or more fluoro substituents; and
wherein * represents the point of attachment to the oxygen atom.

2. The compound according to claim 1, wherein the compound is not a pharmaceutically acceptable salt thereof.

3. The compound according to claim 1, or a pharmaceutically acceptable salt thereof, wherein:
R² represents benzyl, 4-fluorobenzyl, 4-chlorobenzyl, 4-bromobenzyl, 4-methylbenzyl, 4-(trifluoromethyl)benzyl, 4-ethynylbenzyl, 4-cyclopropylbenzyl, 3,4-difluorobenzyl, 3,5-difluorobenzyl, 2-fluoro-4-chlorobenzyl, or 4-(trifluoromethylthio)benzyl;

R³ represents hydrogen, fluoro, methyl, trifluoromethyl, or ethyl; and
R⁵ represents:

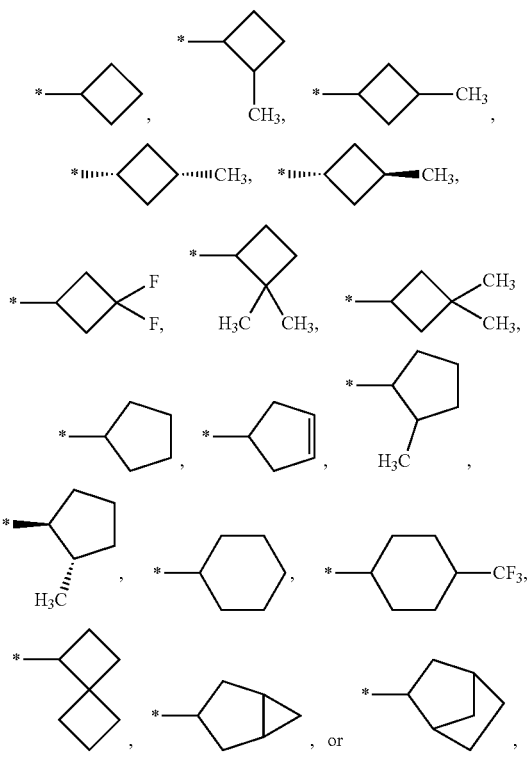

wherein * represents the point of attachment to the oxygen atom.

4. The compound according to claim 3, wherein the compound is not a pharmaceutically acceptable salt thereof.

5. The compound according to claim 1, wherein the compound is selected from the group consisting of:

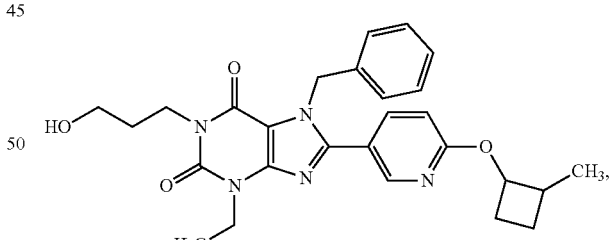

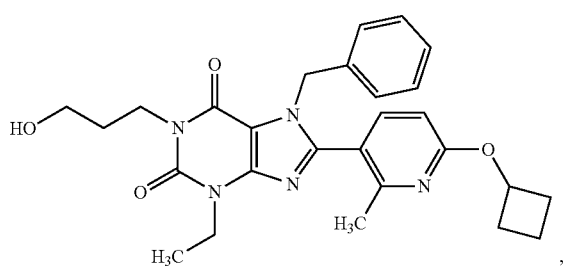

147
-continued
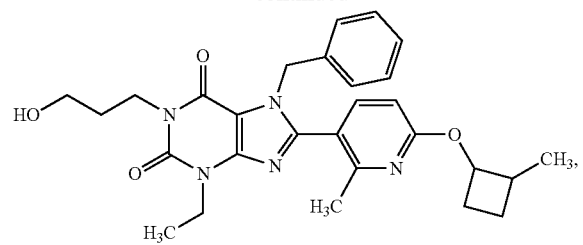
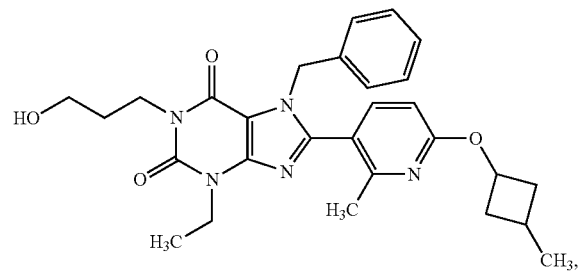
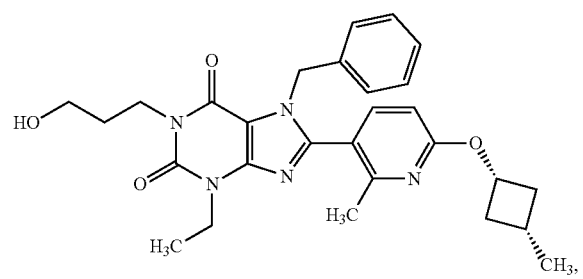
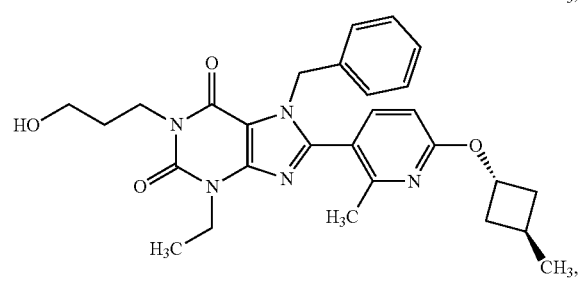
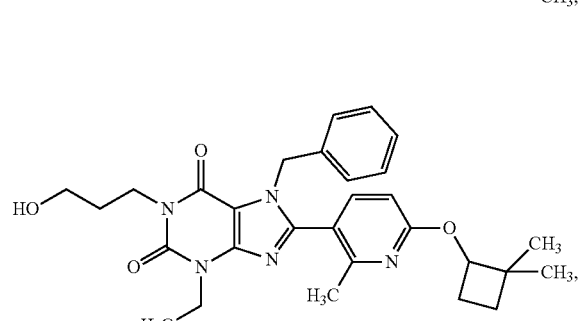
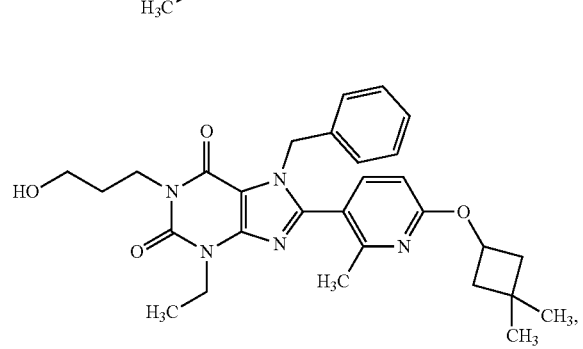
148
-continued
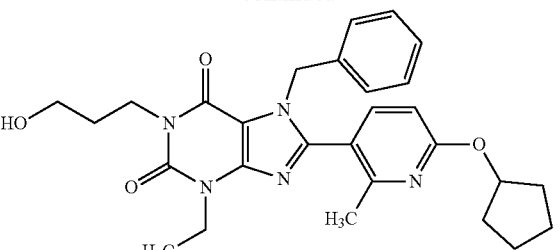
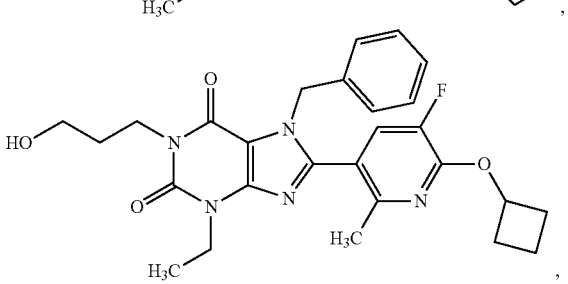
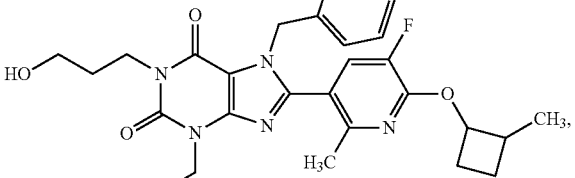
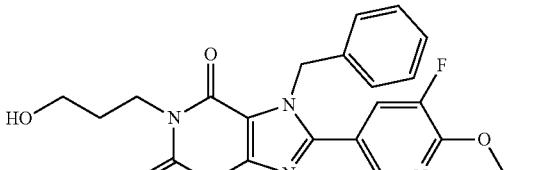
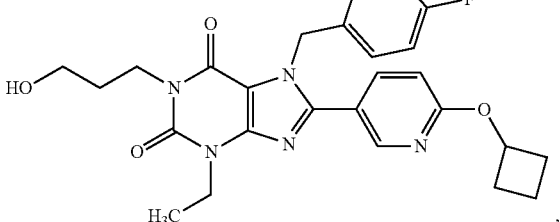
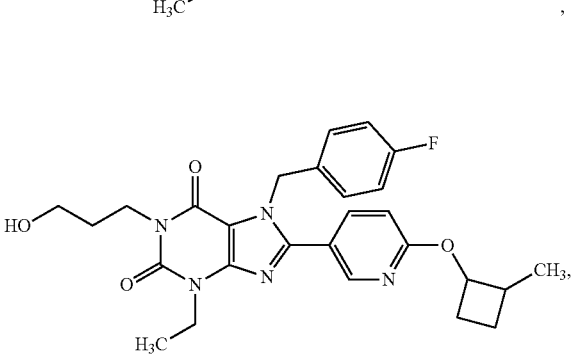

149
-continued
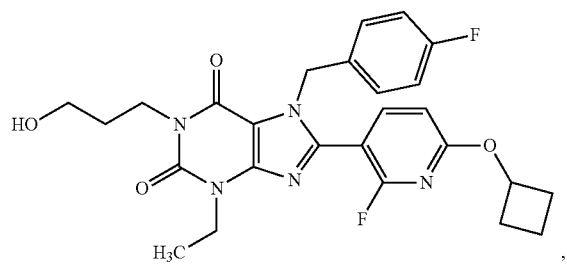
,
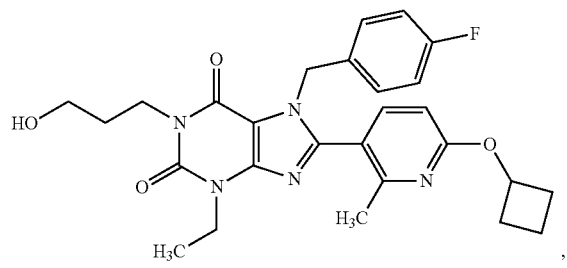
,
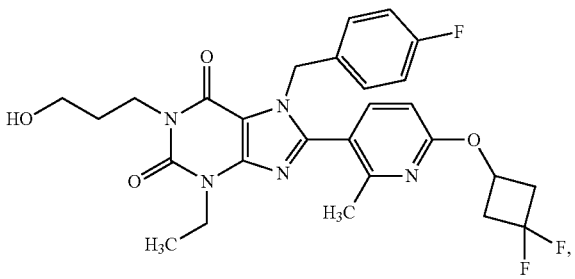
,
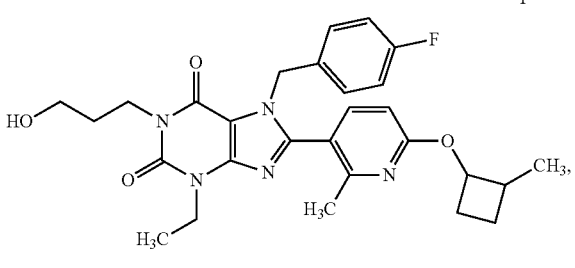
,
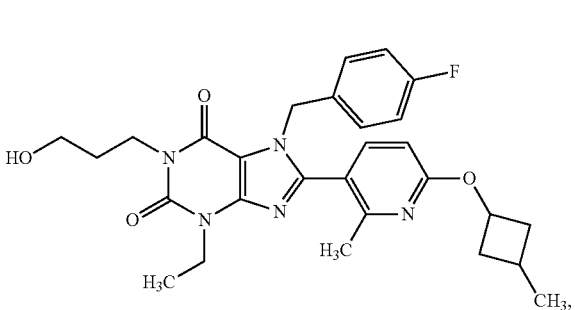
,
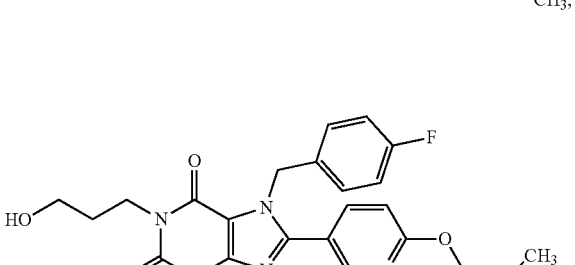
,
150
-continued
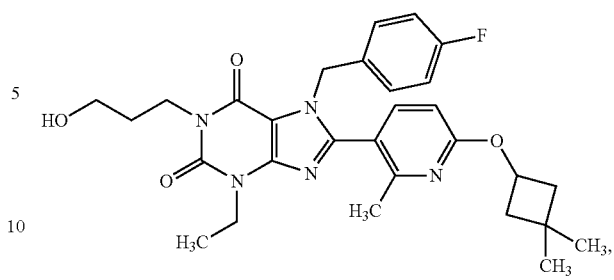
,
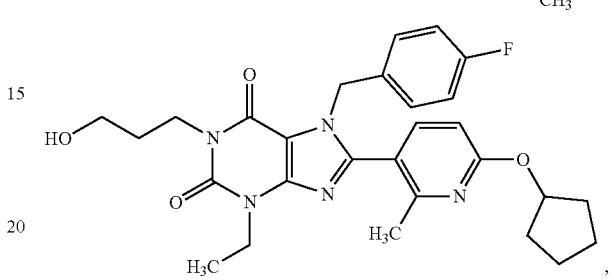
,
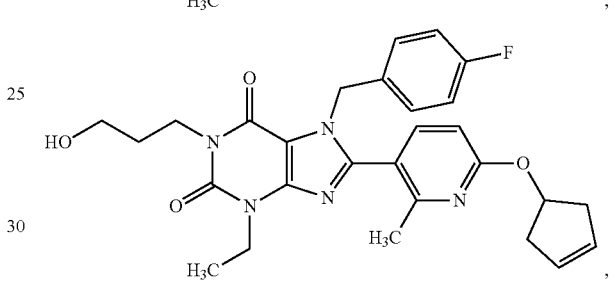
,
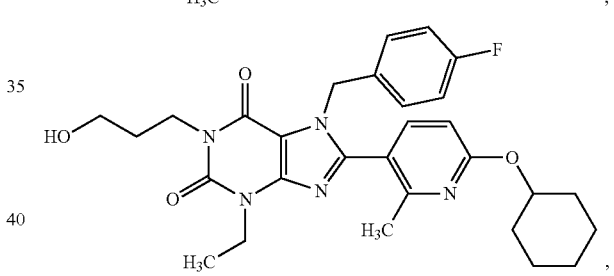
,
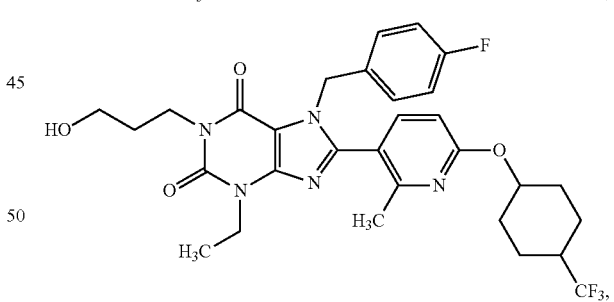
,
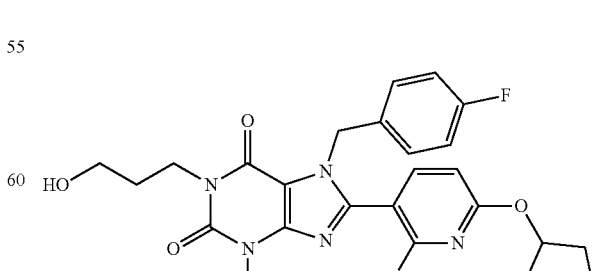
, 151
-continued
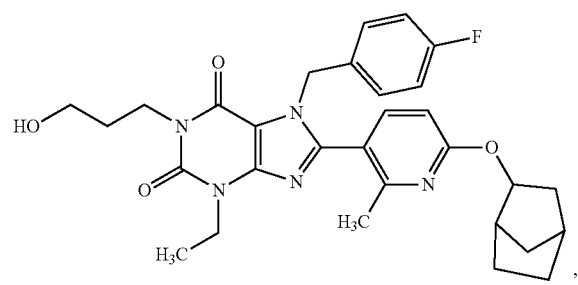
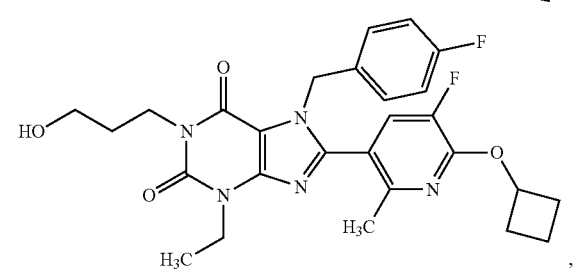
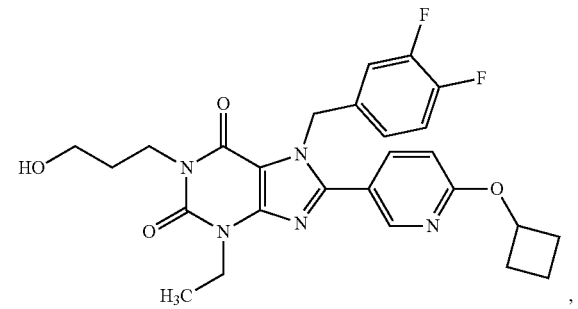
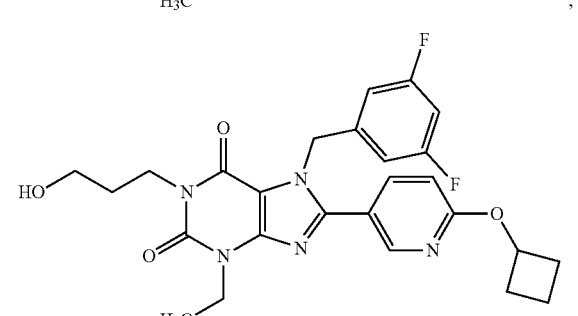
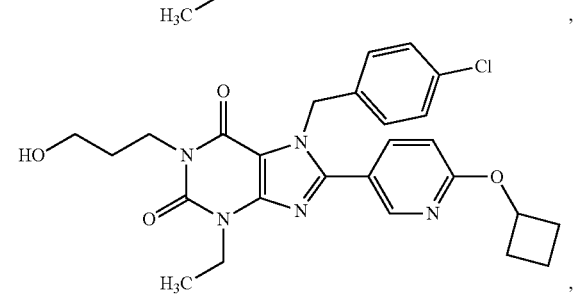
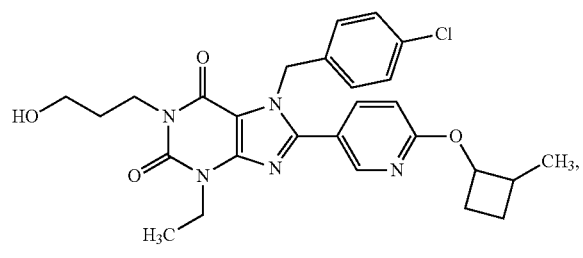
152
-continued
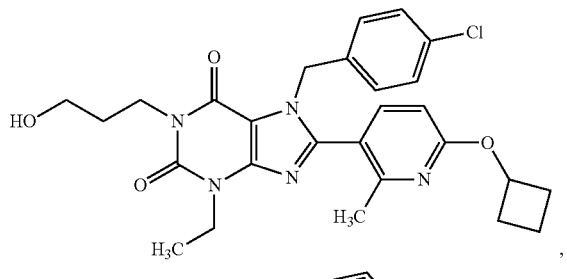
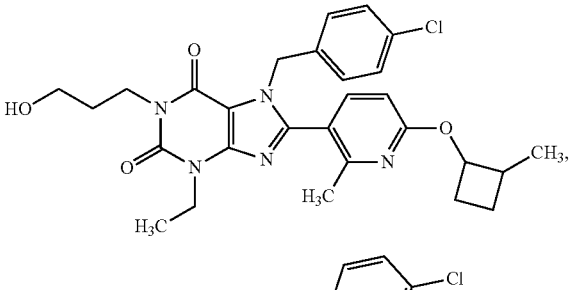
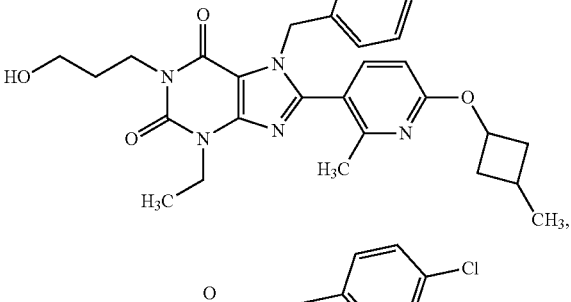
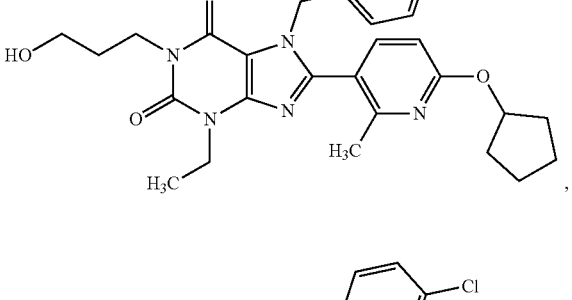
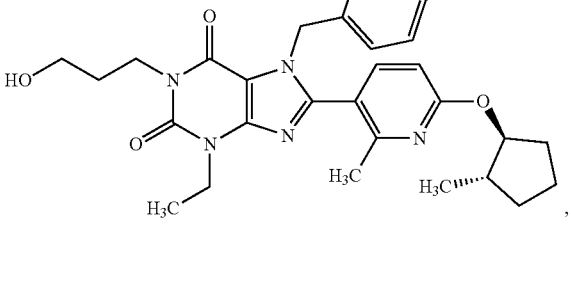
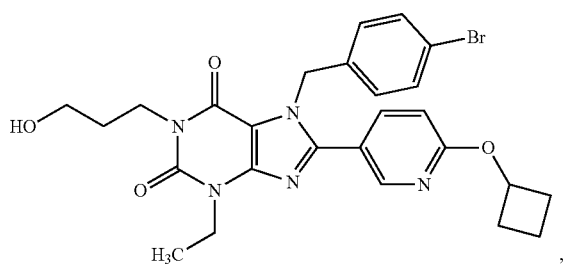

153
-continued
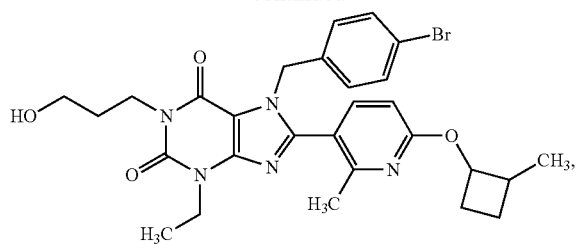
,
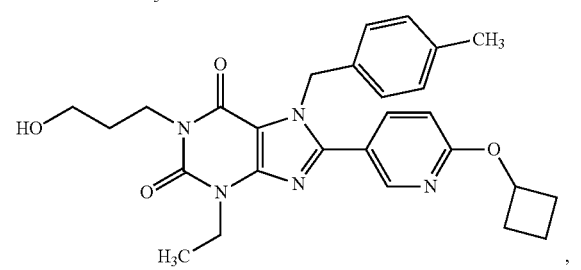
,
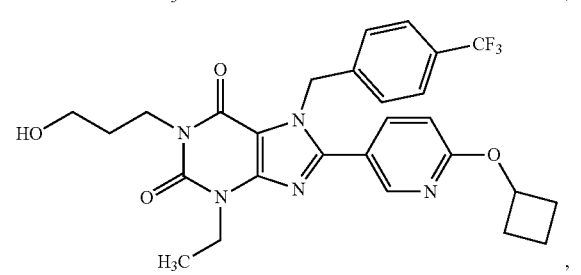
,
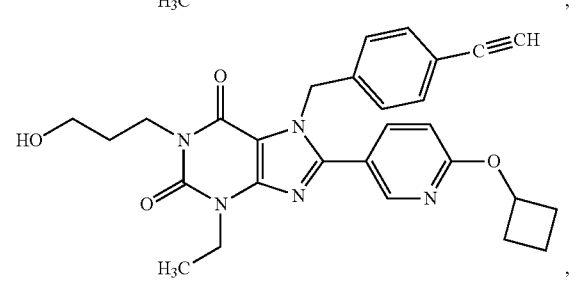
,
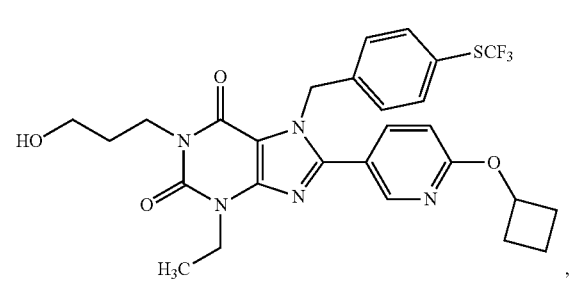
,
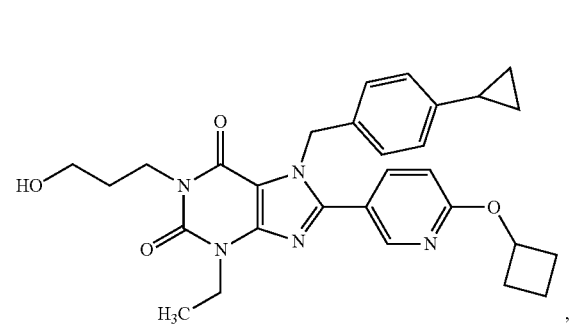
,
154
-continued
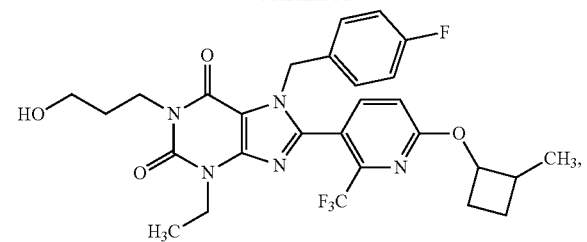
,
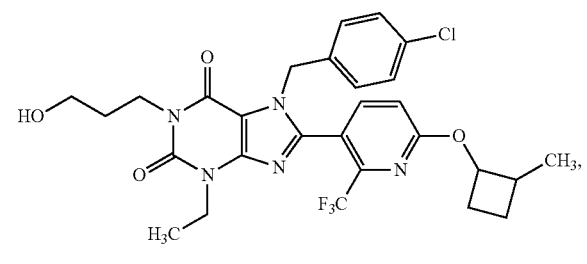
,
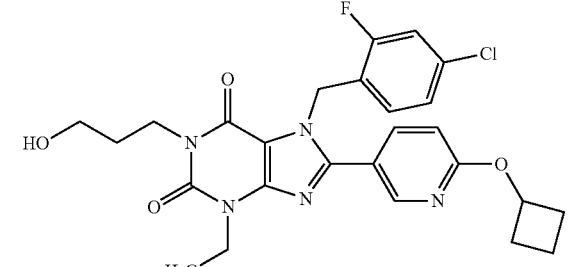
,
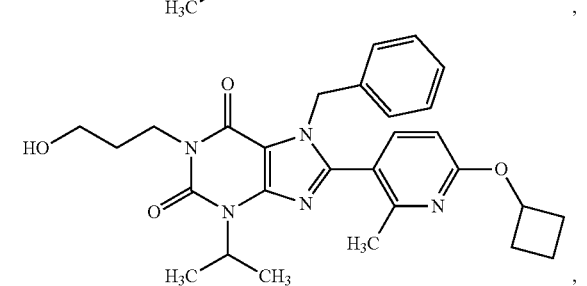
,
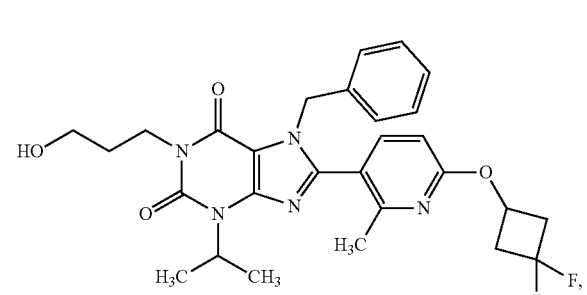
,
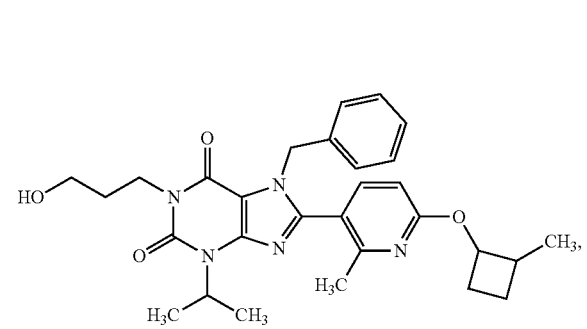

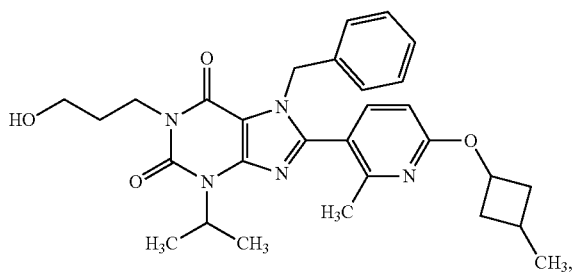
,
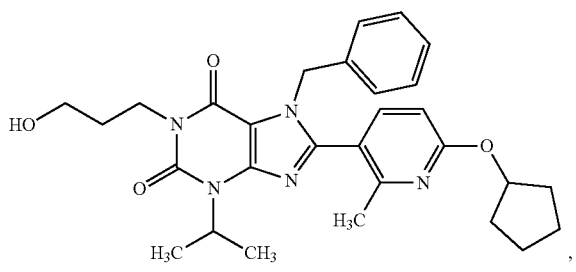
,
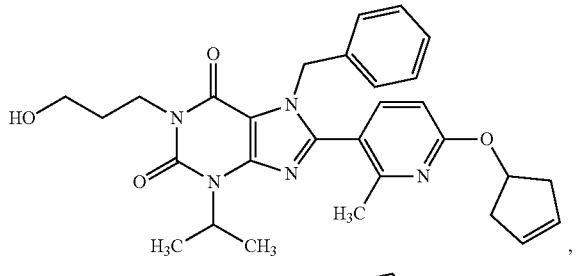
,
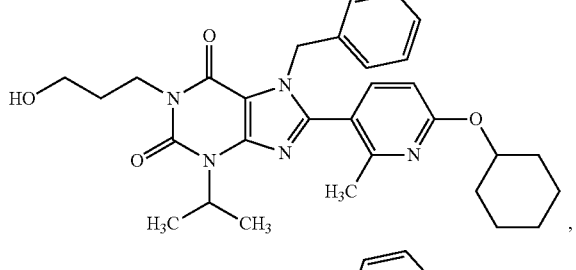
,
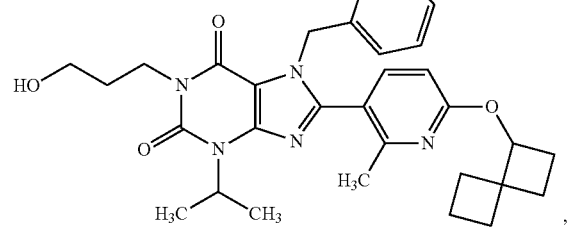
,
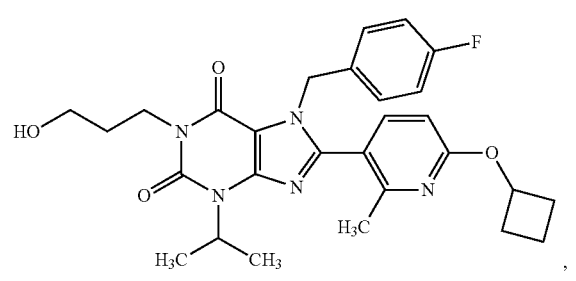
,
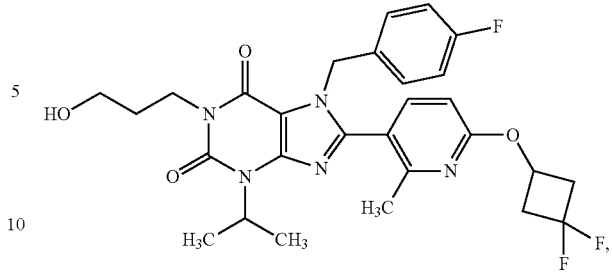
,
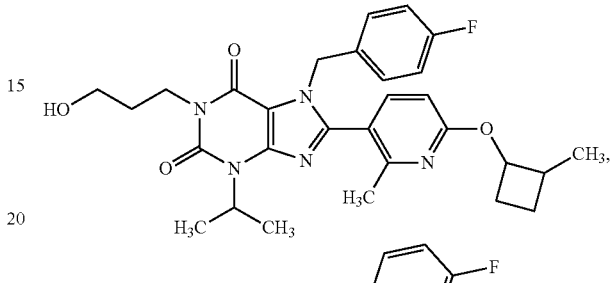
,
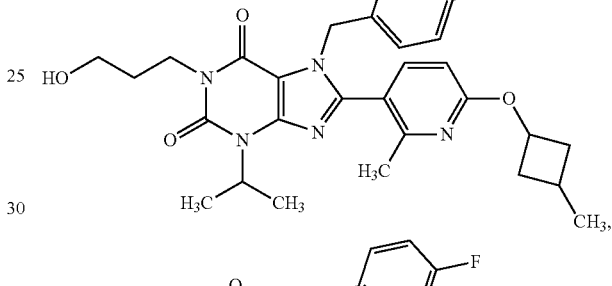
,
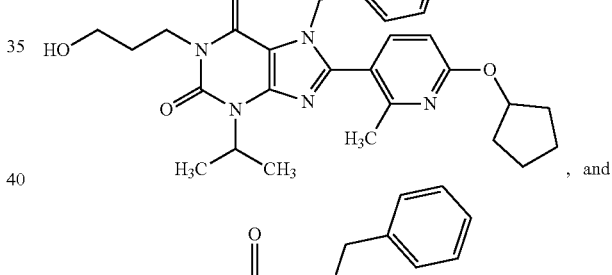
, and
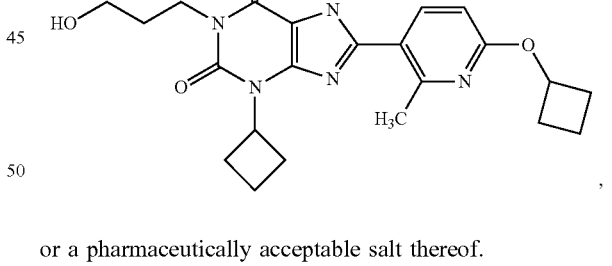
, or a pharmaceutically acceptable salt thereof.

6. The compound according to claim 5, wherein the compound is not a pharmaceutically acceptable salt thereof.

7. A pharmaceutical composition comprising a pharmaceutically acceptable carrier and the compound according to claim 2.

8. A pharmaceutical composition comprising a pharmaceutically acceptable carrier and the compound according to claim 4.

9. A pharmaceutical composition comprising a pharmaceutically acceptable carrier and the compound according to claim 6.

10. A method for inhibiting transient receptor potential cation channel subfamily C, member 5 activity in a subject in need thereof, the method comprising administering to the subject an effective amount of the compound according to claim 1, or a pharmaceutically acceptable salt thereof.

11. The method according to claim 10, wherein the subject has a transient receptor potential cation channel subfamily C, member 5 mediated disorder selected from the group consisting of a neurodegenerative disorder, a neurological disorder, and a psychiatric disorder.

12. The method according to claim 11, wherein the neurodegenerative disorder, neurological disorder, or psychiatric disorder is selected from the group consisting of an addiction, Alzheimer's disease, amyotrophic lateral sclerosis, anxiety, a brain disorder caused by trauma, a disorder associated with dysregulated emotional processing, a disorder associated with impaired impulse control, a fear-related disorder, Huntington's disease, a memory disorder, and Parkinson's disease.

13. The method according to claim 12, wherein the anxiety or fear-related disorder is selected from the group consisting of agoraphobia, generalized anxiety disorder, obsessive compulsive disorder, panic disorder, post-traumatic stress disorder, separation anxiety, social anxiety disorder, and a social phobia.

14. The method according to claim 12, wherein the disorder associated with dysregulated emotional processing is selected from the group consisting of bipolar disorder, borderline personality disorder, and a depressive disorder.

15. The method according to claim 14, wherein the depressive disorder is selected from the group consisting of dysthymia, major depression, major depressive disorder, postpartum depression, and psychiatric depression.

16. The method according to claim 12, wherein the memory disorder is selected from the group consisting of amnesia, aphasia, a brain injury, a brain tumor, chronic fatigue syndrome, Creutzfeldt-Jakob disease, a learning disorder, multiple personality disorder, pain, post-traumatic stress disorder, schizophrenia, a sleeping disorder, a sports injury, stroke, and Wernicke-Korsakoff syndrome.

17. The method according to claim 16, wherein the amnesia is selected from the group consisting of dissociative amnesia and fugue amnesia.

18. A compound selected from the group consisting of:

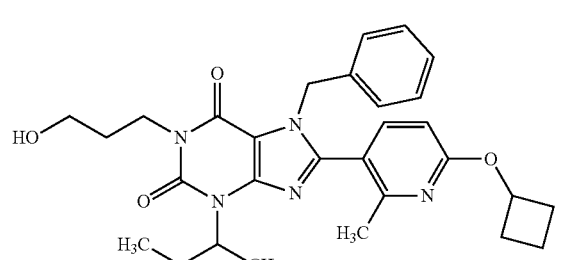

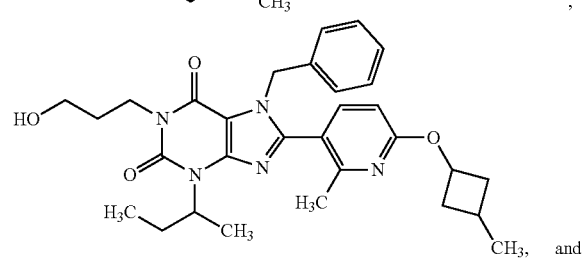

-continued

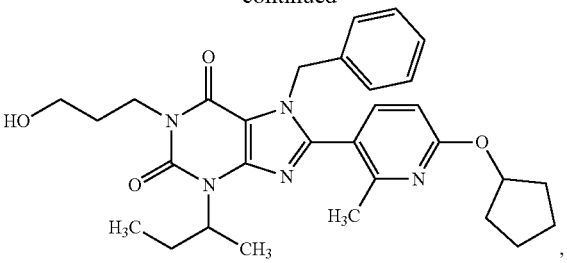

or a pharmaceutically acceptable salt thereof.

19. The compound according to claim 18, wherein the compound is not a pharmaceutically acceptable salt thereof.

20. A pharmaceutical composition comprising a pharmaceutically acceptable carrier and the compound according to claim 19.

21. A compound having the following formula:

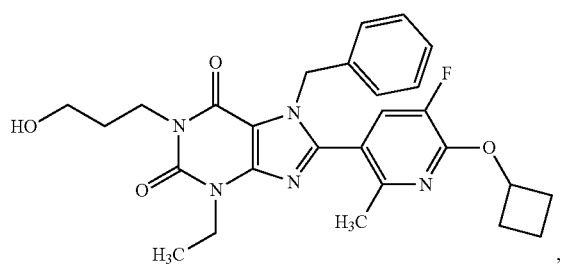 [SMILES: CCn1c(=O)n(CCCO)c(=O)c2c1nc(-c1cc(F)c(OC3CCC3)nc1C)n2Cc1ccccc1]

or a pharmaceutically acceptable salt thereof.

22. A method for inhibiting transient receptor potential cation channel subfamily C, member 5 activity in a subject in need thereof, the method comprising administering to the subject an effective amount of the compound according to claim 21, or a pharmaceutically acceptable salt thereof;
wherein the subject has a transient receptor potential cation channel subfamily C, member 5 mediated disorder selected from the group consisting of borderline personality disorder, major depression, major depressive disorder, and post-traumatic stress disorder.

23. A compound having the following formula:

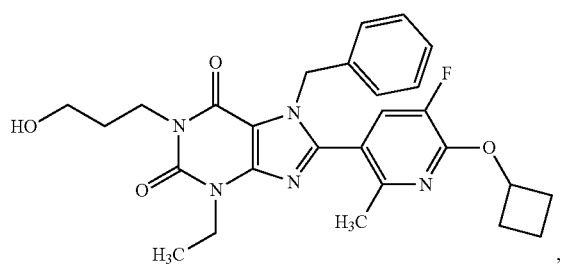 [SMILES: CCn1c(=O)n(CCCO)c(=O)c2c1nc(-c1cc(F)c(OC3CCC3)nc1C)n2Cc1ccccc1]

24. A method for inhibiting transient receptor potential cation channel subfamily C, member 5 activity in a subject in need thereof, the method comprising administering to the subject an effective amount of the compound according to claim 23;
wherein the subject has a transient receptor potential cation channel subfamily C, member 5 mediated disorder selected from the group consisting of borderline personality disorder, major depression, major depressive disorder, and post-traumatic stress disorder.

25. A compound having the following formula:

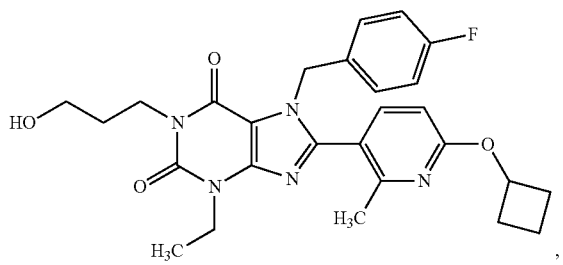 [SMILES: CCn1c(=O)n(CCCO)c(=O)c2c1nc(-c1ccc(OC3CCC3)nc1C)n2Cc1ccc(F)cc1]

or a pharmaceutically acceptable salt thereof.

26. A method for inhibiting transient receptor potential cation channel subfamily C, member 5 activity in a subject in need thereof, the method comprising administering to the subject an effective amount of the compound according to claim 25, or a pharmaceutically acceptable salt thereof;
wherein the subject has a transient receptor potential cation channel subfamily C, member 5 mediated disorder selected from the group consisting of borderline personality disorder, major depression, major depressive disorder, and post-traumatic stress disorder.

27. A compound having the following formula:

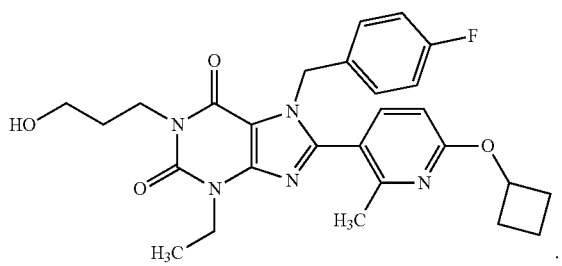 [SMILES: CCn1c(=O)n(CCCO)c(=O)c2c1nc(-c1ccc(OC3CCC3)nc1C)n2Cc1ccc(F)cc1]

28. A method for inhibiting transient receptor potential cation channel subfamily C, member 5 activity in a subject in need thereof, the method comprising administering to the subject an effective amount of the compound according to claim 27;
wherein the subject has a transient receptor potential cation channel subfamily C, member 5 mediated disorder selected from the group consisting of borderline personality disorder, major depression, major depressive disorder, and post-traumatic stress disorder.

29. A compound having the following formula:

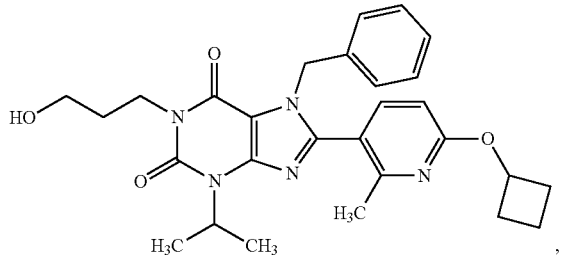 [SMILES: Cc1nc(OC2CCC2)ccc1-c1nc2c(c(=O)n(CCCO)c(=O)n2C(C)C)n1Cc1ccccc1]

or a pharmaceutically acceptable salt thereof.

30. A method for inhibiting transient receptor potential cation channel subfamily C, member 5 activity in a subject in need thereof, the method comprising administering to the subject an effective amount of the compound according to claim 29, or a pharmaceutically acceptable salt thereof;
wherein the subject has a transient receptor potential cation channel subfamily C, member 5 mediated disorder selected from the group consisting of borderline personality disorder, major depression, major depressive disorder, and post-traumatic stress disorder.

31. A compound having the following formula:

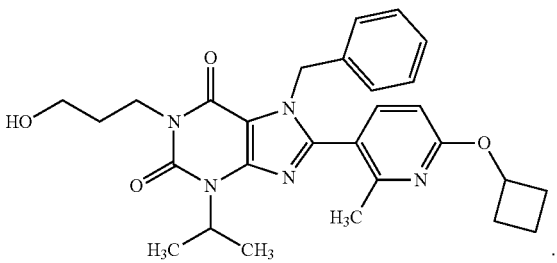 [SMILES: Cc1nc(OC2CCC2)ccc1-c1nc2c(c(=O)n(CCCO)c(=O)n2C(C)C)n1Cc1ccccc1]

32. A method for inhibiting transient receptor potential cation channel subfamily C, member 5 activity in a subject in need thereof, the method comprising administering to the subject an effective amount of the compound according to claim 31;
wherein the subject has a transient receptor potential cation channel subfamily C, member 5 mediated disorder selected from the group consisting of borderline personality disorder, major depression, major depressive disorder, and post-traumatic stress disorder.

33. A compound having the following formula:

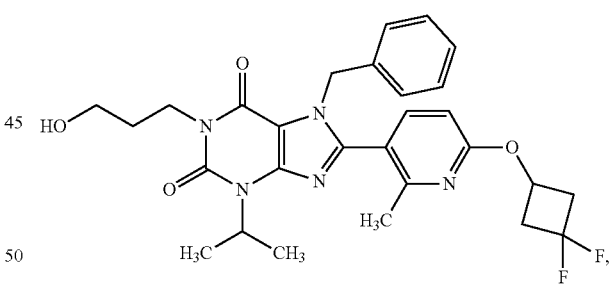

or a pharmaceutically acceptable salt thereof.

34. A method for inhibiting transient receptor potential cation channel subfamily C, member 5 activity in a subject in need thereof, the method comprising administering to the subject an effective amount of the compound according to claim 33, or a pharmaceutically acceptable salt thereof;
wherein the subject has a transient receptor potential cation channel subfamily C, member 5 mediated disorder selected from the group consisting of borderline personality disorder, major depression, major depressive disorder, and post-traumatic stress disorder.

35. A compound having the following formula:

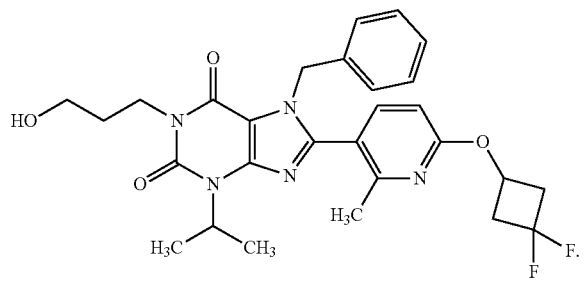 [SMILES: Cc1nc(OC2CC(F)(F)C2)ccc1-c1nc2c(c(=O)n(CCCO)c(=O)n2C(C)C)n1Cc1ccccc1]

36. A method for inhibiting transient receptor potential cation channel subfamily C, member 5 activity in a subject in need thereof, the method comprising administering to the subject an effective amount of the compound according to claim 35;
wherein the subject has a transient receptor potential cation channel subfamily C, member 5 mediated disorder selected from the group consisting of borderline personality disorder, major depression, major depressive disorder, and post-traumatic stress disorder.

37. A compound having the following formula:

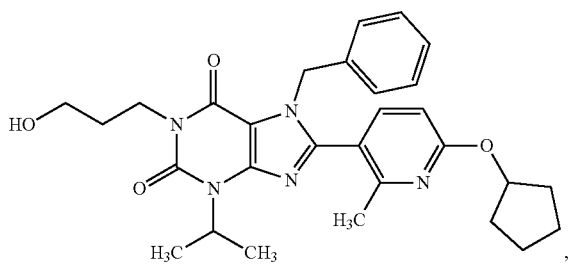 [SMILES: Cc1nc(OC2CCCC2)ccc1-c1nc2c(c(=O)n(CCCO)c(=O)n2C(C)C)n1Cc1ccccc1]

or a pharmaceutically acceptable salt thereof.

38. A method for inhibiting transient receptor potential cation channel subfamily C, member 5 activity in a subject in need thereof, the method comprising administering to the subject an effective amount of the compound according to claim 37, or a pharmaceutically acceptable salt thereof;
wherein the subject has a transient receptor potential cation channel subfamily C, member 5 mediated disorder selected from the group consisting of borderline personality disorder, major depression, major depressive disorder, and post-traumatic stress disorder.

39. A compound having the following formula:

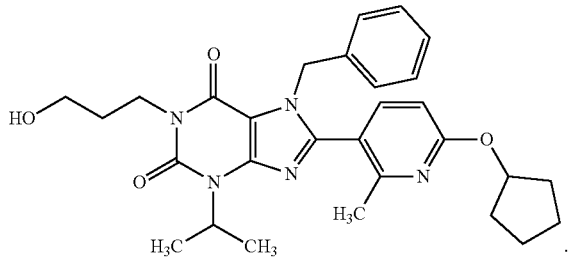 [SMILES: Cc1nc(OC2CCCC2)ccc1-c1nc2c(c(=O)n(CCCO)c(=O)n2C(C)C)n1Cc1ccccc1]

40. A method for inhibiting transient receptor potential cation channel subfamily C, member 5 activity in a subject in need thereof, the method comprising administering to the subject an effective amount of the compound according to claim 39;
wherein the subject has a transient receptor potential cation channel subfamily C, member 5 mediated disorder selected from the group consisting of borderline personality disorder, major depression, major depressive disorder, and post-traumatic stress disorder.

41. A compound having the following formula:

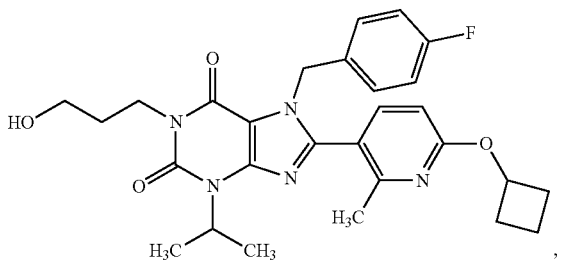 [SMILES: Cc1nc(OC2CCC2)ccc1-c1nc2c(c(=O)n(CCCO)c(=O)n2C(C)C)n1Cc1ccc(F)cc1]

or a pharmaceutically acceptable salt thereof.

42. A method for inhibiting transient receptor potential cation channel subfamily C, member 5 activity in a subject in need thereof, the method comprising administering to the subject an effective amount of the compound according to claim 41, or a pharmaceutically acceptable salt thereof;
wherein the subject has a transient receptor potential cation channel subfamily C, member 5 mediated disorder selected from the group consisting of borderline personality disorder, major depression, major depressive disorder, and post-traumatic stress disorder.

43. A compound having the following formula:

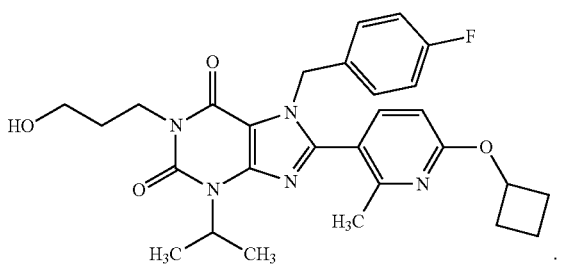 [SMILES: Cc1nc(OC2CCC2)ccc1-c1nc2c(c(=O)n(CCCO)c(=O)n2C(C)C)n1Cc1ccc(F)cc1]

44. A method for inhibiting transient receptor potential cation channel subfamily C, member 5 activity in a subject in need thereof, the method comprising administering to the subject an effective amount of the compound according to claim 43;
wherein the subject has a transient receptor potential cation channel subfamily C, member 5 mediated disorder selected from the group consisting of borderline personality disorder, major depression, major depressive disorder, and post-traumatic stress disorder.

45. A compound having the following formula:

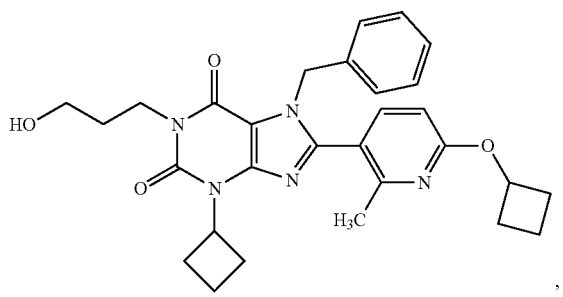 [SMILES: Cc1nc(OC2CCC2)ccc1-c1nc2c(c(=O)n(CCCO)c(=O)n2C2CCC2)n1Cc1ccccc1]

, or a pharmaceutically acceptable salt thereof.

46. A method for inhibiting transient receptor potential cation channel subfamily C, member 5 activity in a subject in need thereof, the method comprising administering to the subject an effective amount of the compound according to claim 45, or a pharmaceutically acceptable salt thereof;
 wherein the subject has a transient receptor potential cation channel subfamily C, member 5 mediated disorder selected from the group consisting of borderline personality disorder, major depression, major depressive disorder, and post-traumatic stress disorder.

47. A compound having the following formula:

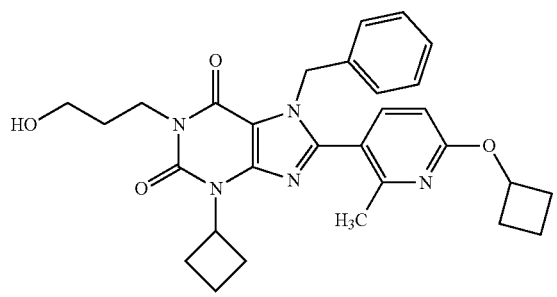

.

48. A method for inhibiting transient receptor potential cation channel subfamily C, member 5 activity in a subject in need thereof, the method comprising administering to the subject an effective amount of the compound according to claim 47;
 wherein the subject has a transient receptor potential cation channel subfamily C, member 5 mediated disorder selected from the group consisting of borderline personality disorder, major depression, major depressive disorder, and post-traumatic stress disorder.

* * * * *

UNITED STATES PATENT AND TRADEMARK OFFICE
CERTIFICATE OF CORRECTION

PATENT NO. : 11,198,696 B2  
APPLICATION NO. : 16/710887  
DATED : December 14, 2021  
INVENTOR(S) : Kai Gerlach Page 1 of 2

It is certified that error appears in the above-identified patent and that said Letters Patent is hereby corrected as shown below:

In the Claims

In Claim 5, at Column 148, Lines 22-41, the following formula:

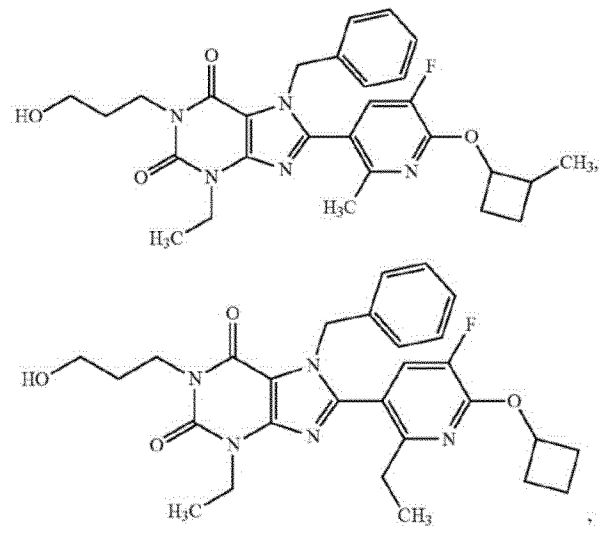

Should be replace with the following:

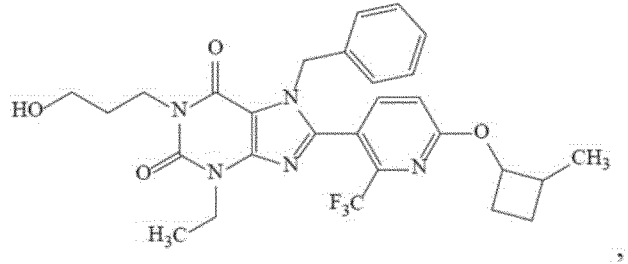

Signed and Sealed this  
Fourteenth Day of June, 2022

Katherine Kelly Vidal  
*Director of the United States Patent and Trademark Office*

CERTIFICATE OF CORRECTION (continued)
U.S. Pat. No. 11,198,696 B2

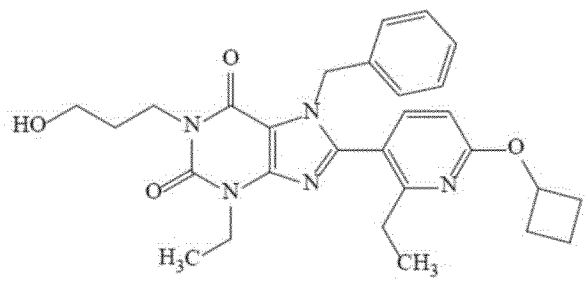

In Claim 5, at Column 152, Lines 43-54, the following formula:

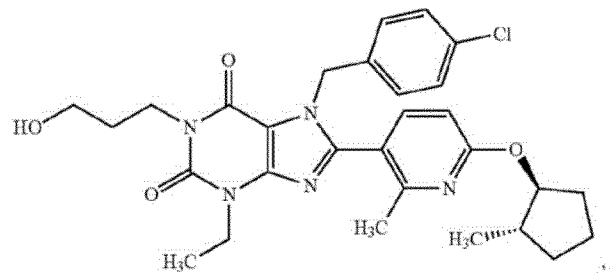

Should be replaced with the following:

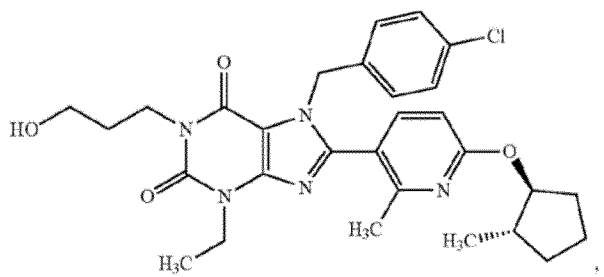

racemic trans-mixture